US010576468B2

(12) United States Patent
Biadillah et al.

(10) Patent No.: US 10,576,468 B2
(45) Date of Patent: Mar. 3, 2020

(54) DEVICES, SOLUTIONS AND METHODS FOR SAMPLE COLLECTION

(71) Applicant: ABOGEN, INC., Portland, ME (US)

(72) Inventors: Youssef Biadillah, Geneva (CH); Stephen Andrews, Falmouth, ME (US); Bryce G. Rutter, St. Louis, MO (US); Melvin J. Leedle, St. Louis, MO (US); Jonathan Sundy, Columbia, MO (US); Benjamin Cooper Priess, St. Charles, MO (US); Chris Briden, Coventry, RI (US)

(73) Assignee: ABOGEN, INC., Portland, ME (US)

( * ) Notice: Subject to any disclaimer, the term of this patent is extended or adjusted under 35 U.S.C. 154(b) by 62 days.

(21) Appl. No.: 15/112,677

(22) PCT Filed: Jan. 20, 2015

(86) PCT No.: PCT/US2015/012038
§ 371 (c)(1),
(2) Date: Jul. 19, 2016

(87) PCT Pub. No.: WO2015/112496
PCT Pub. Date: Jul. 30, 2015

(65) Prior Publication Data
US 2017/0001191 A1    Jan. 5, 2017

(30) Foreign Application Priority Data

Jan. 20, 2014 (EP) ...................................... 14151801
Jan. 20, 2014 (EP) ...................................... 14151830
(Continued)

(51) Int. Cl.
*B01L 3/00* (2006.01)
*B65D 51/28* (2006.01)
(Continued)

(52) U.S. Cl.
CPC ............ *B01L 3/502* (2013.01); *A61B 10/007* (2013.01); *A61B 10/0051* (2013.01);
(Continued)

(58) Field of Classification Search
CPC ............ B65D 51/2871; B65D 41/3447; B01L 2200/085; B01L 2200/141; B01L 2300/046
See application file for complete search history.

(56) References Cited

U.S. PATENT DOCUMENTS 6,149,866 A   11/2000 Luotola et al.
7,300,632 B2  11/2007 Sugiyama et al.
(Continued)

FOREIGN PATENT DOCUMENTS

JP   2000-501191 A   2/2000
JP   2003-344232 A   12/2003
(Continued)

OTHER PUBLICATIONS

International Search Report and Written Opinion, dated Sep. 14, 2015, for International Application No. PCT/US2015/012038.
(Continued)

*Primary Examiner* — Sally A Merkling
(74) *Attorney, Agent, or Firm* — Cooley LLP

(57) ABSTRACT

Some embodiments are directed to a bodily fluid sample collection device for the collection of naturally expressed bodily fluids and include a cap engageable with a tube to close a mouth of the tube. The cap includes a chamber for containing a reagent. The tube defines at least partly a sample collection space for receiving the naturally expressed bodily fluid. The cap comprises first and second cap portions relatively movable with respect to each other. The first and second cap portions are configured such that, responsive to engagement of the cap on the tube, one of the cap portions
(Continued)

is caused to move integrally relative to the other cap portion to open the chamber and permit fluid communication between the chamber and the sample collection space. The reagent in the chamber is thereby permitted to mix with the bodily fluid in the sample collection space. A method of organizing and processing samples is also described.

20 Claims, 21 Drawing Sheets

(30) Foreign Application Priority Data

| | | | |
|---|---|---|---|
| Mar. 17, 2014 | (EP) | ...................................... | 14160215 |
| Jun. 23, 2014 | (EP) | ...................................... | 14173372 |
| Sep. 29, 2014 | (EP) | ...................................... | 14186782 |
| Nov. 10, 2014 | (EP) | ...................................... | 14192586 |
| Nov. 11, 2014 | (EP) | ...................................... | 14192740 |
| Jan. 12, 2015 | (EP) | ...................................... | 15150866 |

(51) Int. Cl.
  *A61B 10/00*    (2006.01)
  *B65D 25/56*    (2006.01)
  *B65D 41/04*    (2006.01)
  *B65D 55/02*    (2006.01)

(52) U.S. Cl.
  CPC .......... *A61B 10/0096* (2013.01); *B65D 25/56* (2013.01); *B65D 41/04* (2013.01); *B65D 51/2835* (2013.01); *B65D 51/2871* (2013.01); *B65D 51/2878* (2013.01); *B65D 51/2892* (2013.01); *B65D 55/02* (2013.01); *B01L 2300/042* (2013.01); *B01L 2300/047* (2013.01); *B01L 2300/0672* (2013.01); *B01L 2400/043* (2013.01); *B01L 2400/0683* (2013.01)

(56) References Cited

U.S. PATENT DOCUMENTS

| | | | |
|---|---|---|---|
| 9,442,046 B2 * | 9/2016 | Biadillah | ........... A61B 10/0051 |
| 2004/0226835 A1 * | 11/2004 | Takahashi | .......... B65D 41/3447 |
| | | | 206/219 |
| 2009/0205506 A1 | 8/2009 | Lin | |

FOREIGN PATENT DOCUMENTS

| | | |
|---|---|---|
| JP | 2010-213660 A | 9/2010 |
| WO | WO 97/48492 A1 | 12/1997 |
| WO | WO 2012/177656 A2 | 12/2012 |

OTHER PUBLICATIONS

Notice of Reasons for Rejection dated Nov. 2, 2018 for Japanese Patent Application No. 2016-546928, with its English language translation, 13 pages.

\* cited by examiner

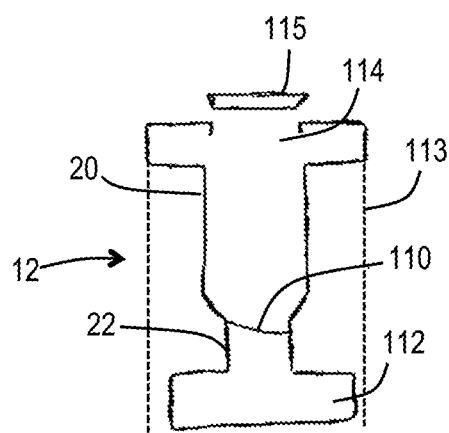
FIG. 20
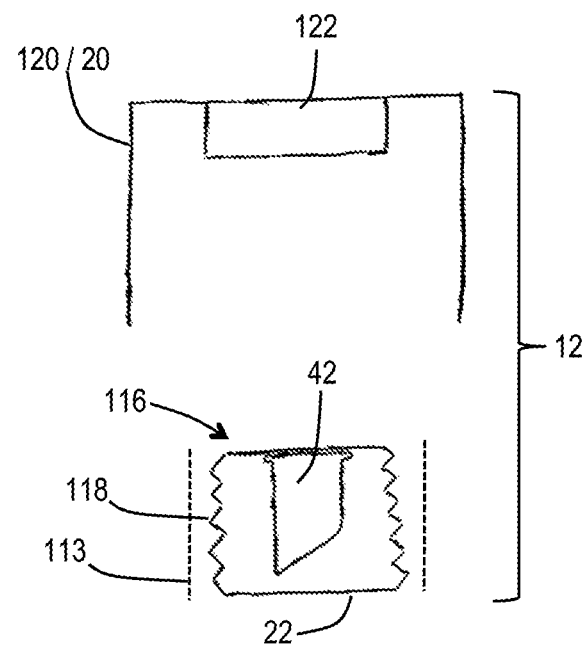
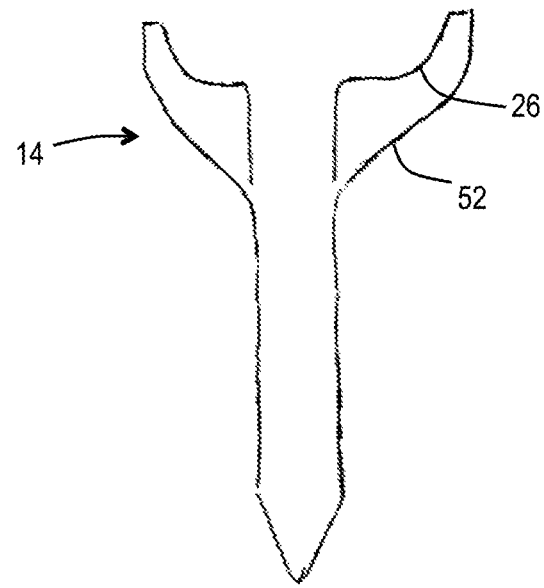
FIG. 21
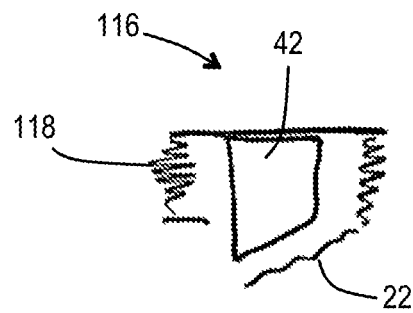
FIG. 22

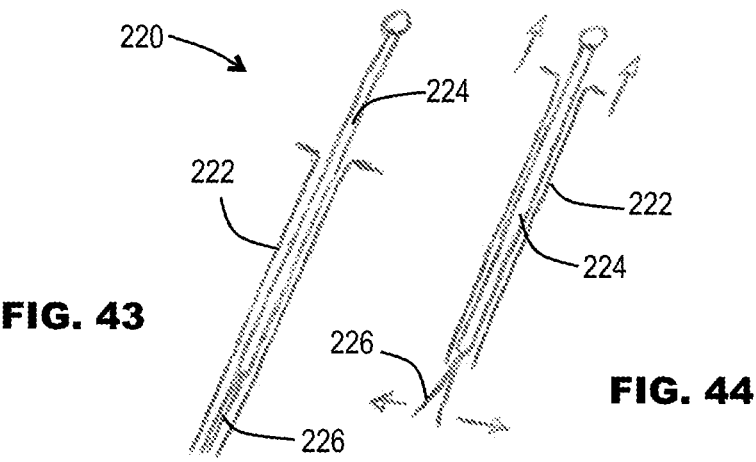
FIG. 43   FIG. 44
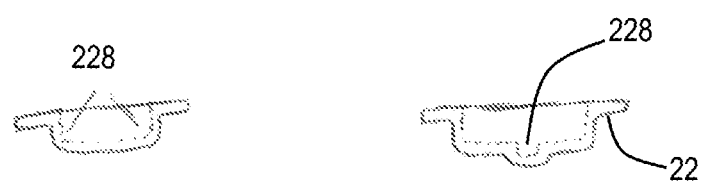
FIG. 45   FIG. 46
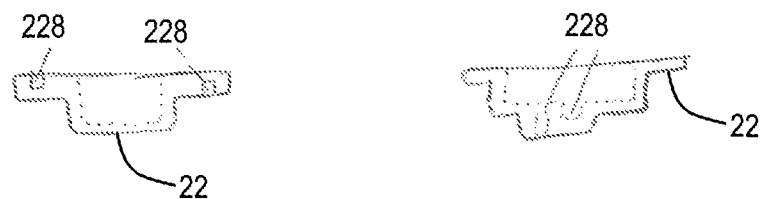
FIG. 47   FIG. 48

DEVICES, SOLUTIONS AND METHODS FOR SAMPLE COLLECTION

RELATED APPLICATIONS

This application is a 35 U.S.C. & 371 national stage entry of PCT/US2015/012038, filed Jan. 20, 2015, which claims priority under 35 U.S.C. § 119 to European Patent Application No. 14 151 801.9, filed Jan. 20, 2014 and entitled "DEVICES, SOLUTIONS AND METHODS FOR SAMPLE COLLECTION"; European Patent Application No. 14 151 830.8, filed Jan. 20, 2014 and entitled "DEVICES, SOLUTIONS AND METHODS FOR SAMPLE COLLECTION"; European Patent Application No. 14 160 215.1, filed Mar. 17, 2014 and entitled "DEVICES, SOLUTIONS AND METHODS FOR SAMPLE COLLECTION"; European Patent Application No. 14 173 372.5, filed Jun. 23, 2014 and entitled "DEVICES, SOLUTIONS AND METHODS FOR SAMPLE COLLECTION"; European Patent Application No. 14 186 782.0, filed Sep. 29, 2014 and entitled "DEVICES, SOLUTIONS AND METHODS FOR SAMPLE COLLECTION"; European Patent Application No. 14 192 586.7, filed Nov. 10, 2014 and entitled "DEVICES, SOLUTIONS AND METHODS FOR SAMPLE COLLECTION"; European Patent Application No. 14 192 740.0, filed Nov. 11, 2014 and entitled "DEVICES, SOLUTIONS AND METHODS FOR SAMPLE COLLECTION"; European Patent Application No. 15 150 866.0, filed Jan. 12, 2015 and entitled "DEVICES, SOLUTIONS AND METHODS FOR SAMPLE COLLECTION"; each of which in turn claims priority to International Application Publication No. WO/2012/177656, filed Jun. 19, 2012 and entitled "DEVICES, SOLUTIONS AND METHODS FOR SAMPLE COLLECTION." The entire contents of the aforementioned applications are herein expressly incorporated by reference.

FIELD OF THE DISCLOSURE

The disclosure relates to devices, solutions and methods for collecting samples of bodily fluids or other substances, including hazardous and/or toxic substances, and in some cases, a naturally expressed bodily fluid (e.g., saliva, urine). Additionally or alternatively, the disclosure relates generally to functional genomics and/or to the isolation and preservation of cells from such bodily fluids, for studies in any of: diagnosis, genetics, functional genomic, epigenetic studies, and biomarker discovery (for example). Additionally or alternatively, the disclosure relates generally to collecting a bodily fluid sample for DNA analysis.

BACKGROUND

Personalized medicine is the customization of treatment to an individual as opposed to the one treatment-for-all model. Personalized medicine involves categorizing a patient based on his or her physical condition and designing an optimal healthcare solution exclusively for that category. The progression of personalized medicine is dependent on the discovery, validation, and commercialization of biomarkers to stratify populations for treatment and for the development of diagnostics for screening and early detection.

Epigenetic research has come to the forefront of medical research and is implicated in the etiology of a number of physical and mental illnesses including: cancer, obesity, diabetes, schizophrenia, and Alzheimer's disease. In addition, Epigenetics may hold particular promise in the many scientific and medical areas including but not limited to: cancer, diabetes, drug integrations, drug effectiveness, childhood aggression, suicidal behaviors, aging, inflammation, pain, obesity, schizophrenia, and other mental illnesses.

SUMMARY OF THE DISCLOSURE

Some embodiments of the disclosure may provide safer and/or easy to use sample collection devices for fluids (for example, naturally expressed bodily fluids), as well as solutions and methods for preserving cells of samples collected, and additionally, methods for isolating specific cells either collected and/or preserved. Such isolated cells (and even non-isolated collected cells), can then be analyzed for studies including but not limited to: functional genomic and epigenetic studies, and biomarker discovery.

The sample collection devices according to the present disclosure can provide several advantages over currently available sample collection devices. For example, in some embodiments, the sample collection devices can use a minimum amount of parts and may not require removal or exchange of a piece or an object thereof. In some embodiments, the sample collection devices may not require any additional manipulation by the sample donor apart from depositing the sample in the sample collection device and closing the sample collection device. In some embodiments, use of the sample collection devices can provide improved safety for both the sample donor and the end user, since, for example, exposed sharp objects are not included and there is limited to no risk of exposure to toxic solutions (e.g., sample preservative solutions). Additionally or alternatively, in some embodiments, the sample collection devices can at least partly separate functionally a fastening of a cap, and release of a reagent into the collected sample. Additionally or alternatively, in some embodiments, the sample collection devices can avoid accidental premature release of a reagent before a cap is fully sealed closed.

In some embodiments of the sample collection device, the sample collection device can have two main mating bodies, a cap and a tube. The cap can include a closed chamber holding a reagent for acting on the collected sample. The cap can mate with the tube to constitute the closed sample collection device. The tube can be configured to receive the donor specimen. The cap and tube are configured so that when the donor deposits the specimen and closes the tube with the cap, the chamber holding the reagent may be opened to release the reagent and allow it to mix with the donor specimen.

As used herein, the term "reagent" may refer to any kind of substance for acting on the collected sample to achieve a desired effect. In some embodiments, the reagent can be a chemical preservative for preserving at least a component of the sample. For purposes of the disclosure, "preserving cells" refers to preventing the cells from having their antigens degraded, such that they can be purified or enriched based on their antigens, and preventing alterations in the cellular epigenome. The "epigenome" refers to the state or pattern of alteration of genomic DNA by covalent modification of the DNA or of proteins bound to the DNA. Examples of such alteration can include methylation at the 5 position of cytosine in a CpG dinucleotide, acetylation of lysine residues of histones, the binding of proteins to the DNA to initiate transcription (for example, transcription factors) and other heritable or non-heritable changes that do not result from changes in the underlying DNA sequence. In other forms, the reagent may be configured to preserve DNA, RNA, or protein components of the sample, suitable for DNA, RNA, or proteomic analysis.

The reagent may be any suitable form, for example, a fluid (e.g. liquid, solution, or gas) or a solid (e.g. powder). In some embodiments, the reagent may be toxic. In such case, it may be desirable to avoid, to the extent possible, any exposure of the reagent to the donor donating the sample to the collection device.

In some embodiments, a bodily fluid sample collection device for the collection of naturally expressed bodily fluids is can be provided, and can include a cap engageable with a tube to close a mouth of the tube. The cap includes a chamber for containing a reagent. The tube can define at least partly a sample collection space for receiving the naturally expressed bodily fluid. The cap comprises first and second cap portions that are (i) relatively movable with respect to each other, and/or (ii) in use moved one relative to the other. The first and second cap portions can be configured such that, responsive to engagement of the cap on the tube, one of the cap portions can move (e.g. integrally) relative to the other cap portion to open the chamber and permit fluid communication between the chamber and the sample collection space. The reagent in the chamber is thereby permitted to mix with the bodily fluid in the sample collection space.

In some embodiments, relative movement between the first and second cap portions may be caused or controlled by a coupling between the cap portions. In other embodiments, the first and second cap portions may be freely movable with respect to each other (such as within a predetermined range of operative movement, and/or notwithstanding friction between the first and second cap portions), and the relative movement between the cap portions may be caused by respective different engagement between each cap portion and the tube.

In some embodiments, the first and second cap portions can be rotatably movable with respect to each other. As used herein, the terms "rotatable" or "rotatably" or "rotate" are used to mean that one cap portion is able to move at least partly angularly about an axis with respect to the other portion, whether or not the angular movement corresponds to a partial turn about the axis, or a fill turn, or more than one full turn, and/or whether or not the relative movement includes an axial component.

In some embodiments, the first and second cap portions can be threadedly coupled together. As used herein, the terms "thread" or "threaded" are used to mean a coupling that defines an at least partly helical movement, whether or not the movement includes a full turn. Relative rotation of one (e.g. cap) portion can cause relative translation between the portions in a direction parallel to the axis.

In some embodiments, the first and second cap portions are coupled together by a bayonet coupling. As used herein, the term "bayonet" refers to a type of coupling movement involving first and second phases, one of which is predominantly rotational, and the other of which is predominantly axial. An example bayonet coupling may be formed by a pin slideable in a slot or track. The slot or track may define an "L" shape, for example, in a circumferential direction.

In some embodiments, the first and second cap portions are relatively movable in a substantially non-rotating manner. For example, the first and second cap portions may be pushed one towards the other, or pulled one away from the other, substantially without rotation.

In some embodiments, the first and second portions may be integrally coupled together, for example, by a captive connection or by a frangible wall portion that breaks in use in response to the relative movement between the first and second portions. Breakage of a frangible wall portion may create or open an aperture or other exit path for releasing the agent from the chamber.

Whether or not the first and second cap portions are rotatably movable with respect to each other, in some embodiments, the cap is rotatably engageable on the tube, for example, threadedly engageable or by a bayonet connection. The type of coupling (e.g. threaded; bayonet) between the cap and tube may be same as, or different from, the type of coupling (e.g. threaded, bayonet) between the first and second cap portions.

In some embodiments, the tube comprises a first engager for engagement by the first cap portion, and a second engager for engagement by the second cap portion. During fitting of the cap to the tube, the engagement between each respective cap portion and engager causes collectively relative movement between the cap portions optionally in combination with a coupling (e.g. active coupling) between the cap portions. For example, in some embodiments, the second engager restrains the second cap portion against substantial rotational movement while the first cap portion is being screwed on to the first engager. This generates relative rotational movement between the cap portions to open the cavity. However, other relative movements are also possible. For example, the second engager may actively generate movement of the second cap portion with respect to the tube, in a different manner from movement of the first cap portion with respect to the tube.

In some embodiments, the first and second engagers may be configured to engage the respective cap portions generally simultaneously, such that attachment of the cap to the tube proceeds generally simultaneously with opening of the chamber. In other embodiments, the first and second engagers may be configured such that one of the engagers may engage its respective cap portion before the other engager engages its respective cap portion. The other engager may engage its respective cap portion after relative movement between the cap and the tube.

For example, in some embodiments, second engager may be configured to be keyed to engage the second cap portion before engagement between the first engager and the first cap portion. Alternatively, the second engager may be configured to engage the second cap portion after the first cap portion has been fitted to engage the first engager.

The nature of the first and second engagers may vary according to the type of relative movement intended between first and second cap portions. At least one of the first and second engagers may comprise at least one selected from: a screw thread; a non-threaded element engageable with a screw thread; a bayonet connection track; an element engageable with a bayonet connection track; a rotation stop; a stop; an abutment; a post; a projection.

The first and second cap portions may be integral with each other, or they may be discrete components.

Whether or not separate components, in some embodiments, the first and second cap components may be at least partly separable to open the chamber. The cap portions may be completely separable or at least a portion of one cap portion may remain non-separated (e.g. coupled or joined) to the other.

Whether or not at least partly separable, and whether or not separate components, the first and second cap portions may, in some embodiments, remain coupled together when the chamber is open, for example, coupled by a captive coupling. Examples of (e.g. captive) coupling may include: a captive or integral tether; a captive or integral cage; a captive or integral hinge; a disengagement stop integrated as part of the coupling; a threaded or bayonet coupling have a range of movement while still in engaged such that disengagement of the cap from the tube does not disengage the threaded or bayonet coupling of the first and second cap portions.

In some embodiments, the tube may comprise a support element for supporting at least a portion of the second cap portion if at least partly disengaged from the first cap portion. The support element may be configured to cooperate with the first and/or second cap portion to prevent the second cap portion from dropping (e.g. entirely) into the sample collection space.

In some embodiments, the first cap portion comprises an outer wall of the cap, and an inner wall defining at least partly the chamber. The second cap portion comprises a closure engageable at and/or over a mouth or aperture of the chamber. For example, the closure may be in the form of a second cap or plug, for example, positioned in an inverted state at and/or over a downwardly opening mouth of the chamber. For example, the chamber may have an open bottom end defining the mouth. The inner wall may depend from an upper or top wall of the cap.

In some embodiments, the second cap (portion) may be relatively short in axial length compared to the inner wall of the first cap portion so that, for example, the majority of the chamber may be defined by the inner wall. Alternatively, in some embodiments, the second cap (portion) may be relatively long axially (or tall) compared to the inner wall of the first cap portion so that, for example, the majority of the chamber may be defined by the second cap (portion). The second cap portion may have the form of a cup suspended from the first cap portion.

In some embodiments, the second cap portion is releasably engageable from the first cap portion to open the chamber. At least partial separation of the second cap portion from the first cap portion, and/or movement of at least a portion of the second cap portion away from the first cap portion may provide a signal to a user in the form of a visual indication that the chamber has been opened and/or that the reagent has been successfully dispensed into the collected bodily fluid sample. In some embodiments, even after the at least partial separation and/or movement away, the first and second cap portions may remain coupled, for example, by a captive or hinged connection. Such a connection may optionally be an integral joint between the first and second cap portions, or it may be a non-integral captive connection or joint.

In some embodiments, the relative movement between the first and second cap portions causes the second cap portion to translate progressively in a direction towards the sample collection space. This may be achieved, for example, by using a screw threaded coupling (between the first and second cap portions), having a thread angle that is opposite in sense (or direction) to the screw threaded coupling between the cap and the tube. The thread angles may be the same or different in magnitude, yet opposite in sense (or direction).

Additionally or alternatively, in some embodiments, the engagement between the second cap portion and the tube (e.g. second engager) is configured to cause the second cap portion to translate progressively, relative to the first cap portion, in a direction towards the sample collection space.

Additionally or alternatively to any of the above, in some embodiments, the collection device may be configured to provide to the user a first signal indicative of the chamber having been opened, and a second signal indicative of the cap having reached a closed and/or locked position.

In some embodiments, the first signal may be or comprise any one or a combination of two or more of: a visual signal, an audible signal, a tactile signal. Additionally or alternatively, the second signal may be or comprise any one or a combination of two or more of: a visual signal, an audible signal, a tactile signal. In some embodiments, the first and second signals may be of the same type as each other, or include one or more signal components or types (e.g. visual and/or audible and/or tactile) in common, or be wholly different.

In some embodiments, the first signal may be provided by movement or displacement or dropping down of at least a portion (for example, substantially all) of the second cap portion towards or into the tube. If the tube is transparent, the movement/displacement of the second cap portion may provide a visual signal to the user. The second cap portion may be colored to enhance visibility (for example, a color different from other colors, for example, of at least the majority (and optionally substantially all) of the first cap portion and/or the tube). Additionally or alternatively, the user may hear and/or feel (tactile) the dropping down of the second cap portion towards or into the tube.

In some embodiments, the second signal may be provided by a lock device that operates or engages upon the cap reaching a predetermined closed condition on the tube. The lock device may, for example, comprise a ratchet or a resilient latch. As used herein, the term ratchet is used to mean any device or mechanism that permits relative movement in a first direction while stopping (or at least obstructing) movement in a second opposite direction. The ratchet or latch may, for example, comprise at least one projection or formation that has a ramp surface for permitting a second component to pass over the formation by riding over the ramp surface in the first direction, and an abutment surface for blocking (or at least obstructing) movement in the second direction. Additionally or alternatively, the ratchet or latch may, for example, comprise a cantilever and/or articulated member configured such that, in use, the member is (i) able to be displaced by a second component for permitting the second component to pass the cantilever/articulated member in the first direction, and (ii) not displaced by the second component when contacted in the second movement direction.

With a lock device, the second signal may include audible and/or tactile signal components generated by the operation of the, for example, ratchet or latch. For example, the user may feel a physical "click" upon the lock operating, and/or hear a "click" sound.

In some embodiments, the first and second movement directions may, for example, be generally axial or they may, for example, be generally circumferential.

Additionally or alternatively to any of the above, in some embodiments, the second cap portion is configured, upon relative movement with respect to the first cap portion, to break the integrity of a frangible wall portion of the chamber, to open the chamber. The frangible wall portion may be a part of the first cap portion and/or a part of the second cap portion and/or a portion joining the first and second cap portions, or it may be a further component of the cap.

In some embodiments, the frangible wall portion is a membrane that at least partly defines a wall of the chamber. For example, the membrane may be of plastics (e.g. plastics film), or a thin metallic sheet (e.g. a foil), or a plastics/ metallic laminate. The frangible wall portion may be fastened to the first cap portion (for example), by adhesive or welding.

In some embodiments, the second cap portion may comprise a metal foil that is welded or glued to the first cap portion. In use, the chamber is opened in response to relative movement, e.g. rotation, between the first and second cap portions. The second cap portion may be disengaged by the weld breaking in response to the relative movement, and/or the foil may be configured to tear or rupture as a result of the relative movement. In some embodiments, such an arrangement may enable the foil to be opened without the need for a cutting or piercing element.

Additionally or alternatively to any of the above, the chamber may be defined by a self-contained chamber module that is fixed to the cap at least prior to attachment of the cap to the tube, in use. In some embodiments, the chamber module may be fixed to the cap as part of manufacture or production, to be supplied to the user in ready-assembled form. In other embodiments, the chamber module could be provided separately for a user to assemble to the cap.

Production of the chamber as a self-contained module may provide advantages in some embodiments. For example, the chamber module may be filled with agent separately from the remainder of production of the cap. The filling with agent could be performed at a different site from the cap molding or production site. Additionally or alternatively, it may allow easier molding of parts, or a greater variety of possible designs of parts, than incorporating the chamber at least party by an integral molding.

Additionally or alternatively, some embodiments of the present disclosure may provide a tube of a sample collection device having a sample collection portion having a smaller interior cross-sectional area than at a mouth for receiving a cap for closing the device. Providing a small cross-sectional area enables a finely graduated fill scale and/or fill line to be provided that may be easily read and judged for collecting small amounts of bodily fluid. Providing a small cross-sectional area may also provide a region in which the second cap portion may be prevented from entering when the second cap portion (in some embodiments) drops downwardly from the first cap portion, thereby keeping the second cap portion at least partly away from the sample collection space.

Additionally or alternatively to any of the above, in some embodiments, the cap may comprise first and second chambers, for containing first and second reagents or first and second reagent components. Plural chambers may enable plural different reagents to be stored separately, and/or plural reagent components to be stored separately. For example, certain reagents or components may have a longer shelf-life when stored separately than when mixed together, and/or may be less sensitive to external influence such as temperature when stored separately, and/or may form an active reagent that is only active for a limited period of time once mixed together.

The first and second chambers may be configured to be opened to release their contents substantially simultaneously, or one before the other. Sequential release of one before the other may be suitable if, for example, it is desirable to have a first of the reagents or reagent components contact the collected sample before the other.

In some embodiments, the cap may comprise respective cap portions that are movable to open the respective chambers. For example, a first cap portion may define at least partly one or both of the first and second chambers; a second cap portion may be movable with respect to the first cap portion to cause opening of the first chamber; a third cap portion may be movable with respect to the first cap portion to cause opening of the second chamber.

Alternatively, the same cap portion may be configured to cause opening of both the first and second chambers, either substantially simultaneously, or one before the other.

In some embodiments, the mechanism for opening the first chamber may be the same as that for the other. In other embodiments, the mechanisms may be different. For example, at least one of the mechanisms may use relative rotation, for example, screw threaded rotation. For example, at least one of the mechanisms may use a frangible wall portion.

In some embodiments, a bodily fluid sample collection device for the collection of naturally expressed bodily fluids is provided and includes a cap engageable with a tube to close a mouth of the tube. The tube defines at least partly a sample collection space for receiving the naturally expressed body fluid. The device (optionally the cap, or optionally the tube) comprises a chamber for containing a reagent for mixing with a collected sample. The cap comprises a first body by which a user manipulates the cap, and a second body that is rotatably mateable with the tube for securing the cap to the tube. A coupling between the first and second bodies may be configured for (i) transmitting torque from the first body to the second body for permitting rotation of the second body to secure the second body to the tube, and (ii) permitting slippage between the bodies after the second body has reached a fully secured position. A mechanism is operable to cause the chamber to be opened in response to manual rotation of the first body at least after the second body has reached the fully secured position.

The mechanism may be operable to begin to cause the chamber to be opened only after the second body has reached the fully secured position, or the mechanism may be operable partly before the second body has reached the fully secured position. In either case, the second body may reach the fully secured position before the chamber has been fully opened. Further manual rotation of the first body after the second body has reached the fully secured position, may open or complete the opening of the chamber.

The second body may be threadedly mateable with the tube, but other rotatably mateable couplings, such a bayonet coupling, may be used as desired. As used herein, the terms "rotatable" or "rotatably" or "rotate" are used to mean that one body or portion is able to move at least partly angularly about an axis with respect to another body or portion, whether or not the angular movement corresponds to a partial turn about the axis, or a full turn or more than one full turn, and/or whether or not the relative movement includes an axial component.

In some embodiments, the coupling may be a torque-responsive coupling. In some embodiments, the coupling may be a torque-limiting coupling that limits the amount of torque transmissible from the first body to the second body, and permits relative slippage between the two bodies when the torque exceeds a threshold. For example, during initial fitting (e.g. screwing) of the cap, the second body may rotate relatively freely as it mates with the tube, and the applied torque may be small. Once the second body reaches a fully secured position, it can no longer rotate relative to the tube, and the applied torque will therefore increase. The coupling may be responsive to applied torque to permit the first body to slip with respect to the second body, thereby permitting continued rotation of the first body despite the second body no longer being able to rotate.

In some embodiments, the coupling may be responsive to the direction of rotation, so as not to transmit significant torque in a direction for releasing the second body.

In some embodiments, the coupling may comprise a ratchet and/or a clutch.

In some embodiments, the second body may be substantially shrouded by the first body, at least during fitting of the cap on the tube.

In some embodiments, the mechanism for causing opening of the chamber may be responsive to relative rotation between the tube and the first cap portion. Alternatively, the mechanism for causing opening of the chamber may be responsive to rotation between the first and second bodies.

Various mechanisms are envisaged. In one form, the chamber may comprise an aperture closed by a closure. The closure may be a third body distinct from the first body, or it may be integral with the first body. The closure may be rotatable relative to the chamber to open the chamber. For example, the closure may be threadedly coupled to the chamber. In some embodiments, the chamber may be rotatable with the first member. The mechanism may operate restrain the closure against rotation with respect to the tube and/or the second body. Rotation of the first body may rotate the chamber, thereby generating relative rotation between the chamber and the closure, to move the closure to an open condition with respect to the chamber aperture.

Other types of mechanisms for opening the chamber may also be used, for example a piercing element that ruptures a frangible film or wall of the chamber.

In another aspect, in some embodiments, a bodily fluid sample collection device for the collection of naturally expressed bodily fluids is provided and includes a cap engageable with a tube to close a mouth of the tube. The tube defines at least partly a sample collection space for receiving the naturally expressed body fluid. The device (optionally the cap, or optionally the tube) comprises a chamber for containing a reagent for mixing with a collected sample. The device (optionally the cap, or optionally the tube) may further comprise a manually operable actuator operable from outside the device at least once the cap has been secured to the tube, for causing the chamber to be opened in response to manual actuation of the actuator.

In some embodiments, the device may optionally comprise a lockout mechanism for preventing actuation of the actuator before the cap has been placed in a fully secured position.

In some embodiments, the actuator may be rotatable and/or pressable and/or depressable.

In some embodiments, the device may be provided as part of a kit containing packaging in which the device is intended to be placed for sending (e.g. by post) to a processing institution for processing, analysis or research. The packaging may be configured to accept the device only in a condition in which the actuator has been actuated to cause the chamber to be opened. For example, packaging may include a predetermined space (e.g. a well) that is dimensioned to receive the device only in such a condition. The actuator may, for example, be depressable, whereby an exterior dimension of the cap or tube becomes smaller. Prior to depression, the device may be too large to fit in the predetermined space of the packaging. The device may only fit once the actuator has been fully depressed. Such an arrangement can ensure that the user does not accidentally forget to operate the actuator.

In another aspect, in some embodiments, a bodily fluid sample collection device comprises a tube, and a cap securable to a mouth portion of the tube. The cap may be a separate body from the mouth portion, and securable thereto to close the mouth portion. The tube defines at least partly a sample collection space for receiving the naturally expressed body fluid. The device (optionally the cap, or optionally the tube) comprises a chamber for containing a reagent for mixing with a collected sample.

In some embodiments, the mouth portion may be separable from a collection portion of the tube, to facilitate opening of the device after the cap has been secured. For example, the mouth portion may be coupled to the collection portion by a threaded connection, or some other mechanical connection, or by a frangible integral connection.

The mouth portion may flare towards an open end defining a mouth of the tube, and/or narrow towards the collection portion.

In some embodiments, the cap and the mouth portion together comprise a mechanical or adhesive lock tier locking the cap in its fully secured condition once the cap has been closed. With such an arrangement, the ability to separate the mouth portion from the collection portion of the tube may facilitate ease of access to the sample contents when the device is received at a processing installation, while still obstructing accidental opening of the cap by the user having deposited a sample.

Additionally or alternatively, in some embodiments, the cap may comprise a closure for a chamber for containing reagent. The closure may be configured to be opened when, or after, the cap may be secured to the mouth portion, the closure dropping down into the mouth portion when the closure is opened. The mouth portion may prevent the closure from dropping into the collection portion of the tube. With such an arrangement, the ability to separate the mouth portion from the collection portion of the tube may facilitate easy access to the sample contents, without having to manually retrieve the closure from the mouth portion. Instead, by removing the mouth portion itself, the closure is removed with the mouth portion.

Additionally or alternatively, in some embodiments, the ability to separate the mouth portion from the collection portion may enable the sample to be handled, processed or stored in a generally more compact form of the collection portion without a flared or funnel shaped mouth portion.

Devices disclosed herein may optionally be used as part of a kit, that may optionally be provided to a user for collection of a bodily fluid sample at home or in another non-medical environment.

Devices disclosed herein may optionally be used to collect a sample of naturally expressed bodily fluid, for example, saliva or urine.

Devices disclosed herein may optionally be used to collect a bodily fluid sample, for preservation of cells and/or cellular components, such as DNA. The collected sample may be subjected to analysis for the purposes of genetics, epigenetics, diagnostics, or other purposes.

In some embodiments, the solution is able to preserve cells in a naturally expressed bodily fluid sample (for example, saliva or urine), at least to a predetermined efficacy, for a period of at least one week, optionally at least two weeks, optionally at least three weeks, optionally at least a month, optionally at least two months, optionally at least three months.

For purposes of the disclosure, "preserving cells" means preventing the cells from having their antigens degraded, such that they can be purified or enriched based on their antigens, and preventing alterations in the cellular epigenome. The "epigenome" means the state or pattern of alteration of genomic DNA by covalent modification of the DNA or of proteins bound to the DNA. Examples of such alteration include methylation at the 5 position of cytosine in a CpG dinucleotide, acetylation of lysine residues of histones, and other heritable or non-heritable changes that do not result from changes in the underlying DNA sequence As used herein the term "efficacy" may mean that at least a predetermined percentage of the cells in the original bodily fluid sample are preserved. The predetermined percentage may optionally be at least 50%, at least 55%, at least 60%, at least 65%, at least 70%, optionally at least 75%, optionally at least 80%, optionally at least 85%, optionally at least 90%, optionally at least 95%. (The cell concentration per unit volume may be reduced compared to the original body fluid sample, because the mixing of the original sample with the preservation solution increases the net volume of the mixture, thereby diluting the cell concentration.)

Additionally or alternatively, the efficacy may refer to the number of cells (e.g. of a certain type, e.g. T-cells) per unit volume. For example, the number of (e.g. such) cells may be at least about 5000 per ml, optionally at least about 10000 per ml, optionally at least about 12000 per ml.

Additionally or alternatively, in some embodiments, the solution may have a shelf life at room temperature of at least 1 month, optionally at least two months, optionally at least three months, optionally at least four months.

For example, in some embodiments, a solution for preserving cells in bodily fluids, such as saliva and urine, is provided for further separation into cell types and downstream analysis that allows for the cells in saliva to retain their antigenicity and cellular architecture during storage. The solution can contain at least one chemical fixing agent, such as but not limited to paraformaldehyde, and at least one protease inhibitor. In some embodiments, the solution may further contain, for example, one or more of: at least one antimicrobial agent, serum proteins from human and/or other animal species. The solution may be buffered at a pH between about 6.4 to about 8.4, and in some embodiments, between about 7.2 to about 7.6.

In some embodiments, a method for preserving cells in one or more bodily fluids includes contacting collected cells with a solution according to one and/or another embodiment of the present disclosure, which allows the cells to retain their antigenicity and epigenome, for example.

In some embodiments, a method for isolating cells from chemically fixed cells collected from a bodily fluid, e.g., saliva or urine, and includes centrifuging the cells to separate, for example, DNA and/or other soluble material from a pellet of cells, bacteria, and debris, enriching white blood cells from other contents of the pellet, and isolating specific cells (e.g., white blood cells) using antibodies conjugated to magnetic beads targeted to cell specific markers.

In some embodiments, methods for isolating a particular type of cell, for example, a type of white blood cell (e.g., lymphocytes), from one or more bodily fluids (e.g., saliva and/or urine), and includes one or more of the following steps (and, depending upon the embodiment, several or all of the following steps): providing a sample of bodily fluid comprising chemically fixed cells, optionally centrifuging the bodily fluid sample to obtain a pellet comprising cells, optionally re-suspending the pellet in a buffer, subjecting the re-suspended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents may be magnetic beads coupled to antibodies specific to an epitope found on a particular type of white blood cell, and in the separation step may then comprise, for example, magnetically separating the particular type of white blood cell (including lymphocytes) from the mixture of white blood cell types (though other cell separation techniques are within the scope of the disclosure).

In some embodiments, the bodily fluid (e.g., saliva, urine) can be mixed with a chemical fixative solution and the mixture can be removed from the pellet. The pellet can then be re-suspended in a buffer. The re-suspended pellet may optionally be centrifuged and washed one or more times in the buffer. The washed pellet may then be applied to a hydrophilic polysaccharide mixture to form a gradient. This gradient may be different than that used for blood because the density of the cells in other bodily fluids (e.g., saliva, urine) after chemical fixation for preservation can be different due to the different density of the preserved cells requiring an alteration in the time, temperature, and/or density of the gradient for the cells to be processed through this density gradient.

Additionally, in some embodiments, the white blood cells can form a layer in the gradient. The white blood cell layer can be extracted from the gradient and placed in another centrifuge tube where it may be washed in a buffer and re-pelleted to remove the remaining gradient mixture. The pellet may then be re-suspended and incubated in a buffer containing antibodies that are conjugated to magnetic beads and specific to antigens that are specific for a cell type to be isolated. In some embodiments, the cell type to be isolated is T-cells and the antigen is a T-cell-specific antigen. In some embodiments, the antigen is CD4. The re-suspended cells in the buffer can be bound by the antibody and subjected to a magnetic field that magnetically attracts the cells bound to the antibody-conjugated magnetic beads to the side of the tube. Remaining liquid may then be removed from the tube and the tube is washed in buffer. Isolated T-cells then remain attracted to the side of the tube and are ready for further processing, such as freezing for later downstream experimentation (for example).

In some embodiments, a method for preserving cells in a naturally expressed bodily fluid comprises contacting the bodily fluid with the preservation solution according to any of the disclosed embodiments.

The devices, solutions and methods of sample collection, preservation, isolation and analysis will be better understood in light of the following drawings, detailed description and claims. Like reference symbols in the various drawings indicate like elements.

It is worth noting that while some embodiments of the sample collection devices disclosed herein are set forth for use with the collection of bodily fluids, the same also has particular use with the collection of any other substance, including hazardous and/or toxic fluids.

While certain features and aspects of the embodiments have been highlighted above and in the appended claims, protection is claimed for any novel feature or idea described herein and/or illustrated in the drawings whether or not emphasis has been placed thereon.

BRIEF DESCRIPTION OF THE DRAWINGS

FIG. 20 is a schematic section showing a cap in which first and second cap portions are integrally formed, according to some embodiments.

FIG. 21 is an exploded sectional view showing a sample collection device including a variable volume and/or shape chamber unit, according to some embodiments.

FIG. 22 is a schematic section showing the principle of opening the variable volume and/or shape chamber unit of FIG. 21, according to some embodiments.

FIG. 43 is a schematic section view of an alternative example of mechanical retrieval tool, shown in a non-deployed state.

FIG. 44 is a schematic section view of the mechanical retrieval tool of FIG. 43, but shown in a deployed state, according to some embodiments.

FIG. 45 is a schematic section view of a second cap portion showing a first example of engagement surface for mechanical retrieval using the tool of FIGS. 43 and 44, according to some embodiments.

FIG. 46 is a schematic section view of a second cap portion showing a second example of engagement surface for mechanical retrieval using the tool of FIGS. 43 and 44, according to some embodiments.

FIG. 47 is a schematic section view of a second cap portion showing a third example of engagement surface for mechanical retrieval using the tool of FIGS. 43 and 44, according to some embodiments.

FIG. 48 is a schematic section view of a second cap portion showing a fourth example of engagement surface for mechanical retrieval using the tool of FIGS. 43 and 44, according to some embodiments.

DETAILED DESCRIPTION OF THE EMBODIMENTS

Figure 1:
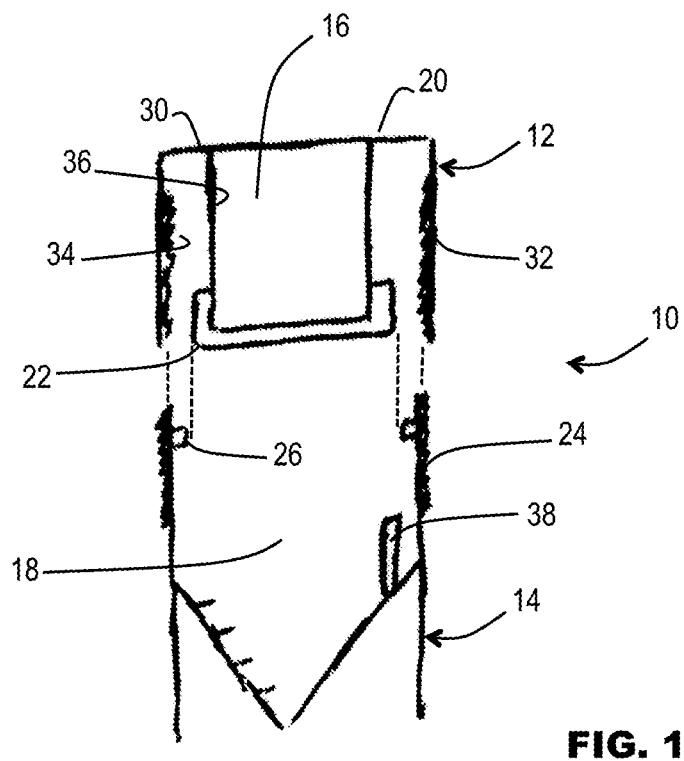
FIG. 1 is a schematic section though a sample collection device comprising a cap and a tube, shown with the cap separated from the tube, according to some embodiments.

Embodiments of the present disclosure include devices, solutions and methods for the collection of samples, such as bodily fluids, as well as methods for isolating one or more cell types from collected cells (chemically fixed or otherwise). For example, in some embodiments, the sample collection devices provide several advantages over currently available sample collection devices, and in addition, the sample collection devices according to some embodiments use a minimum amount of parts and the devices do not require removal or exchange of a piece or an object. Furthermore, in some embodiments, the sample collection devices may generally not require additional manipulation by the sample donor apart from depositing the sample and closing the collection device. The sample collection devices according to some embodiments include improved safety of use for both sample donors and end users due, at least in part, to the elimination of exposed sharp objects and limited risk of exposure to toxic solutions, as will be described in greater detail below.

The same reference numerals are used to denote equivalent or similar features amongst the different embodiments. Where further construction detail is needed, or detail of a reagent, or of how the device may be used, reference may be made to the aforementioned WO 2012/177656 already incorporated herein by reference in its entirety.

Referring to the drawings, some embodiments of the sample collection device 10 may include two mating bodies, such as a cap 12 and a tube 14. In some embodiments, the cap 12 may include a closed chamber 16, such as an interior or in-cap space, for holding a reagent (which may be toxic). The cap 12 may be configured for mating with the tube 14 to constitute a closed sample collection device. The tube 14 may be configured to receive a donor specimen, such as one or more bodily fluids (e.g., saliva, urine) in a collection space 18. In some embodiments, the cap 12 and/or tube 14 may be configured so that when the donor deposits the specimen and closes the tube 14 with the cap 12, the chamber 16 in the cap, which may be holding the reagent, can be opened to release the reagent and allow it to mix with the donor specimen.

In the following description, the reagent is described in the form of a preservative solution for preserving at least a component of the collected sample for further analysis. In some embodiments, the preservative solution is a non-lysing preservative effective to preserve (e.g. chemically fix) entire cells for epigenetic analysis. However, the principles of the disclosure encompass other types of reagent, without prejudice to the preferred preservative solution described. If a different reagent is to be used, all references to preservative solution are to be interpreted as applying to that different reagent. Some embodiments may optionally use a reagent as described later below with respect to FIG. 58.

One of skill in the art will appreciate that with respect to some embodiments of the collection device described herein, such may be used in combination with accessories that ease specimen deposit within the collection device, including, for example, mouth adapters for saliva collection, funnels and hoses for urine collection, and the like.

In some embodiments, the sample collection device 10 may comprise a cap 12 engageable with a tube 14 to close a mouth of the tube 14. The cap 12 may include a chamber 16 for containing a preservation fluid. The tube 14 may define at least partly a sample collection space 18 for receiving naturally expressed bodily fluid. The cap 12 may comprise first and second cap portions 20 and 22 relatively movable with respect to each other. The first and second cap portions 20 and 22 may be configured such that, responsive to engagement of the cap 12 on the tube 14, one of the cap portions (e.g. the first cap portion 20) is caused to move (e.g. integrally) relative to the other cap portion (e.g. second cap portion 22) to open the chamber 16 and permit fluid communication between the chamber 16 and the sample collection space 18. The preservative fluid in the chamber 16 may thereby be permitted to mix with the bodily fluid in the sample collection space 18.

In some embodiments, the first cap portion 20 and/or the second cap portion 22 may be a single part, for example, an integral plastics molding. Additionally or alternatively, the first cap portion 20 and/or the second cap portion 22 may comprise multiple parts assembled together. Illustration of the cap portions 20 and 22 as single parts in one or more of the drawings is merely schematic, and does not limit the scope of the embodiments.

Figure 2:
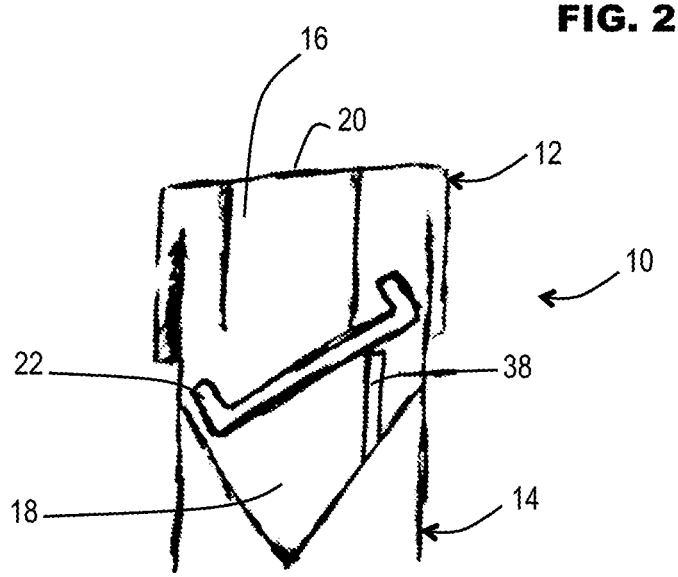
FIG. 2 is a schematic section similar to FIG. 1, showing the cap engaged on the tube, according to some embodiments.
Figure 3:
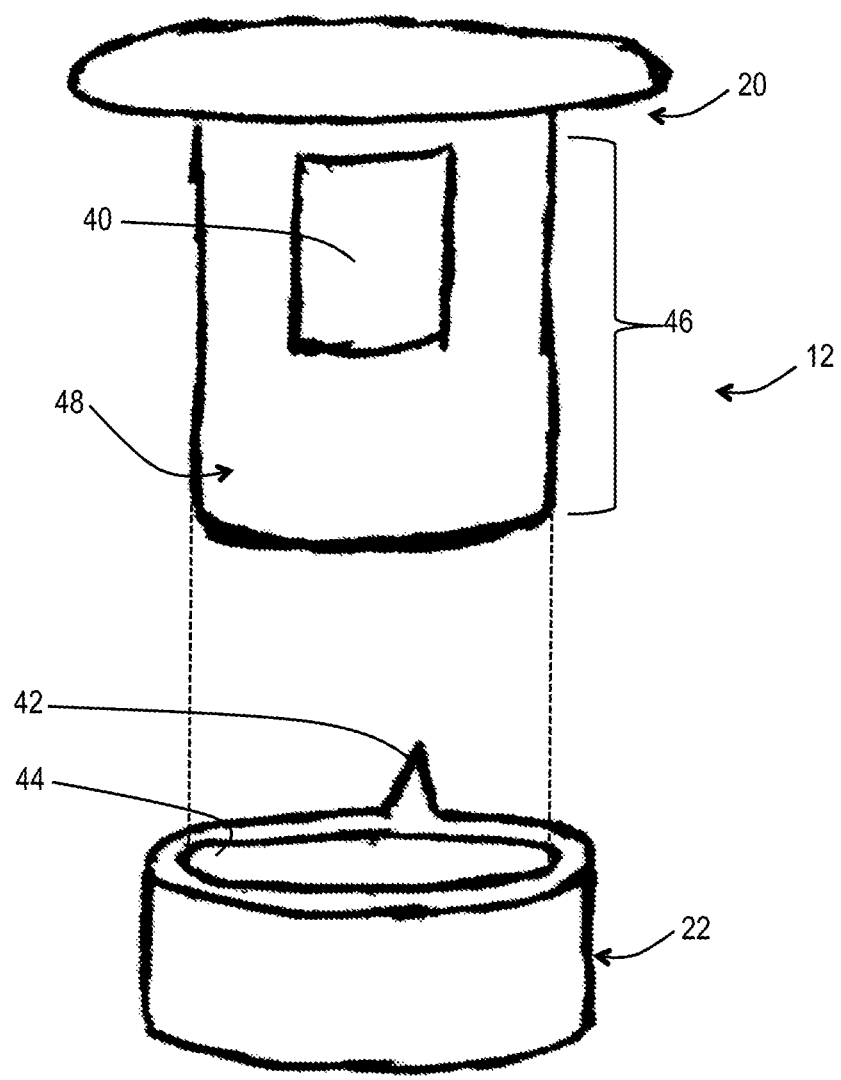
FIG. 3 is a schematic section through a cap of a second example of sample collection device, according to some embodiments.

In some embodiments, relative movement between the first and second cap portions 20 and 22 may be caused or controlled by a coupling between the cap portions. Such a coupling may be referred to herein as an "active" coupling that influences the relative movement. For example, FIGS. 1-3 illustrate such an "active" coupling in the form of a screw thread, and FIGS. 4-7 illustrate an "active" coupling in the form of a bayonet coupling. In other embodiments, the first and second cap portions may be freely movable with respect to each other (at least within a predetermined range of operative movement, and/or notwithstanding friction between the first and second cap portions), and the relative movement between the cap portions may be caused by respectively different engagements between each cap portion and the tube. Such a coupling between the cap portions may be referred to as a "passive" coupling, that does not influence the relative movement (for example see FIGS. 8 and 9).

In some embodiments, the first and second cap portions 20 and 22 are rotatably movable with respect to each other. In some embodiments, the first and second cap 20 and 22 portions may be threadedly coupled together. Relative rotation of one cap portion causes relative translation between the portions in a direction parallel to the axis. However, in other embodiments, the first and second cap portions 20 and 22 may be coupled by a bayonet coupling (FIGS. 4-7)

Whether or not the first and second cap portions 20 and 22 are rotatably movable with respect to each other, in some embodiments, the cap 12 is rotatably engageable on the tube 14, for example, threadedly engageable or by a bayonet connection. The type of coupling (e.g. threaded; bayonet) between the cap 12 and tube 14 may be same as, or different from, the type of coupling (e.g. threaded, bayonet) between the first and second cap portions 20 and 22.

In some embodiments, the tube 14 may comprise a first engager 24 for engagement by the first cap portion 20, and a second engager 26 for engagement by the second cap portion 22. During fitting of the cap to the tube, the engagement between the respective cap portions and engagers causes (e.g. collectively) relative movement between the cap portions, optionally in combination with a coupling (e.g. active coupling) between the cap portions. For example, in some embodiments, the second engager 26 restrains the second cap portion 22 against substantial rotational movement while the first cap portion 20 is screwed on to the first engager 24. This generates relative rotational movement between the cap portions 20 and 22 to open the chamber or cavity.

However, other relative movements are also possible. For example, the second engager 26 may actively generate movement of the second cap portion 22 with respect to the tube 14, in a different manner from movement of the first cap portion 20 with respect to the tube 14.

The nature of the first and second engagers 24 and 26 may vary according to the type of relative movement intended between first and second cap portions. At least one of the first and second engagers 24 and 26 may comprise at least one selected from: a screw thread; a non-threaded element engageable with a screw thread; a bayonet connection track; an element engageable with a bayonet connection track; a rotation stop; a stop; an abutment; a post; a projection.

The first and second cap portions 20 and 22 may be integral with each other, or they may be discrete components. Integral components may, for example, be integrally molded together, or be coupled together by an integral coupling or joint.

Figure 38:
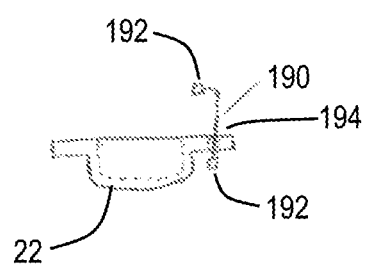
FIG. 38 is a schematic section view showing a second cap portion (in isolation), with a tether, according to some embodiments.

In some embodiments, the first and second cap portions 20 and 22 may be captively coupled to each other, for example, by a tether (shown at 190 in FIG. 38). The tether may be integral with at least one of the portions 20 and 22. Additionally or alternatively, the tether may be non-integral with at least one of the components (for example, a loop defining a captive coupling). In the form illustrated in FIG. 38, the tether 190 comprises a strap having a retainer protrusion or shoulder 192 at at least one end, optionally at each opposite end. The tether 190 may pass through one or more apertures, for example aperture 194 shown in the second cap portion 22. The protrusions) may retain the tether 190 captively engaged in the aperture, so that in turn the first and second cap portions 20 and 22 are relatively movable, but captively coupled.

Referring specifically to the example of FIGS. 1 and 2, in some embodiments, the first cap portion 20 comprises an outer wall of the cap (for example, a top wall 30, and depending side wall 32 carrying a screw thread 34), and an (e.g. depending) inner wall 36 defining at least partly the chamber 16. The second cap portion 22 comprises a closure engageable at and/or over a mouth or aperture of the chamber 16. For example, the closure 22 may be in the form of a second cap or plug, for example, positioned in an inverted state at and/or over a downwardly opening mouth of the chamber 16. For example, the chamber may have an open bottom end defining the mouth. The inner wall 36 may depend from the top wall 30 of the cap 12. Additionally, or alternatively, the closure 22 may be coupled to the inner wall 36 by a screw threaded connection (not shown). In some embodiments, where at least a portion of the second cap portion 22 may fit partly within the aperture, the second cap portion 22 may be referred to as a plug or plug-like.

Use of a closure 22 as described herein may facilitate production of the device 10, and filling of the chamber 16. It is relatively easy to fill the chamber 16 with the first cap portion 20 in an inverted state, and the chamber 16 presenting an open cup space. Thereafter, the closure 22 (second cap portion) may be screwed into place on the first cap portion 20 to close the chamber 16. The closure 22 may use standard capping techniques to ensure a reliable seal preventing leakage of the preservative solution when the cap 12 is subsequently placed in an upright (or non-inverted) orientation, without involving excessive torquing of the closure 22 on to the first cap portion 20.

In some embodiments, the second cap portion (e.g. closure, cap or plug) 22 is at least partly disengageable and/or at least party separable from the first cap portion 20 to open the chamber. Movement of at least a portion of the second cap portion 22 away from the first cap portion 20 may provide a signal (first signal) to a user in the form of a visual indication that the chamber 16 has been opened and/or that the preservation solution has been successfully dispensed into the collected bodily fluid sample. The second cap portion 22 (or at least a portion of the second cap portion 22) may be colored with a contrasting color to aid its visibility. For example, the color may be different from that of the first cap portion and/or the tube. The tube (or at least a portion of the tube) may optionally be transparent or translucent. In addition to, or as an alternative to a visual signal, the falling down of the second cap portion 22 into the tube may generate an audible sound and/or produce a tactile knock, thereby providing additional/alternative components of a signal to the user.

In the illustrated form (FIG. 2), once the closure 22 is (e.g., at least partly) disengaged from the first cap portion 20, at least a portion of the closure may drop towards or into the sample collection space 18, where it is easily visible to the user. As shown in FIG. 2, in the (e.g., at least partly) disengaged state, the second cap portion 22 may optionally lie in an inclined position partly trapped or supported by a support 38. The support 38 may obstruct the second cap portion 22 from falling completely into the sample collection space 18, where it may interfere with intermixing of the reagent with the collected sample. In the illustrated form, the support 38 is a post that wedges the second cap portion 22 in combination with the inner wall 36. However, many other forms of support may be used as desired, for example, a cage or keep (e.g. as described later with respect to FIGS. 49 and 50). In some embodiments (e.g. described later with respect to FIGS. 10 and 11, and subsequent figs.), the interior cross-sectional area of the tube may be smaller in the sample collection space, than at the mouth. The narrowing of the interior cross-section may also act as a natural support or stop to obstruct the second cap portion from dropping (e.g. fully) into the sample collection space. Alternatively, the second cap portion 22 may remain integrally or captively coupled to the first cap portion 20.

In some embodiments, the relative movement between the first and second cap portions 20 and 22 causes the second cap portion 22 to translate progressively in a direction towards the sample collection space 18. This may be achieved, for example, by using a screw threaded coupling (between the first and second cap portions 20 and 22), having a thread angle opposite in sense (or direction) to the screw threaded coupling between the cap 12 and the tube 14. The thread angles may be the same or different in magnitude, yet opposite in sense (or direction). As the first cap portion 20 is screwed on to the tube 14, the closure 22 is restrained from rotating and "unscrews" in a downward direction until it disengages from the first cap portion 20, or achieves an open position not disengaged entirely from first cap portion. For example, the length of the screw threaded coupling between the first and second cap portions 20 and 22 may be such that the second cap portion 22 does not unscrew completely, but instead attains an open position while remaining threadedly coupled to the first cap portion 20.

Where a screw threaded coupling is used between the first and second cap portions, in some embodiments (e.g. shown in FIGS. 1, 2, 3, 26, 28 and 29), a radially inwardly facing thread of the second cap portion 22 may optionally engage with a radially outwardly facing thread of the first cap portion 20 (for example, carried on a radially outwardly facing surface of the inner wall 36 of the first cap portion 20). Alternatively, in some embodiments (e.g. shown in FIGS. 12, 16, 25, 32, 34, 36 and 37) a radially outwardly facing thread of the second cap portion 22 may optionally engage with a radially inwardly facing thread of the first cap portion 20 (for example, carried on a radially inwardly facing surface of the inner wall 36 of the first cap portion 20).

In some embodiments, the first and second engagers 24 and 26 may be configured to engage respective cap portions 20 and 22 substantially simultaneously, such that the relative rotation of one cap portion with respect to the other commences as soon as the cap 12 has begun to be screwed on to the tube 14. However, in other embodiments, the second engager 26, for example, may be configured not to engage the second cap portion 22 to restrain rotation until the cap 12 has already been screwed partway on to the tube 14. Such an arrangement may facilitate establishment of a seal between the cap 12 and tube 14 before any relative rotation of the cap portions 20 and 22 to open the chamber 16. However, such an arrangement also reduces the range of rotation between the cap portions 20 and 22 compared to the range of movement between the cap 12 and tube 14. Alternatively, the second engager 26 for example, may be configured to engage the second cap portion 22 before the first engager 24 engages the first cap portion 24. The parameters may be varied according to design preference.

Referring to an alternative example shown in FIG. 3, in some embodiments, the chamber in the cap for holding a preservative solution is at least partly defined or closed by a frangible wall portion 40. In some embodiments, the frangible wall portion 40 is a membrane that at least partly defines a wall of the chamber and/or closes an aperture in the chamber wall. For example, the membrane may be of plastics (e.g. plastics film), or a thin metallic foil or sheet, or a plastics/metallic laminate. The frangible wall portion 40 may be a part of one of the cap portions, or it may be a further component of the cap. The frangible wall portion 40 may be fastened to one of the cap portions (for example), by adhesive or welding, or by a mechanical fastening, or held captive by a carrier.

In the example illustrated in FIG. 3, the frangible wall portion 40 is mounted to the first cap portion 20. The frangible wall portion may be in the form of a blister encapsulating the preservative solution and/or closing an aperture in the chamber wall. In the case of an encapsulated blister, the blister may be produced and filled separately using conventional blister forming/filling techniques, and subsequently mounted.

In some embodiments, one of the cap portions (e.g. second cap portion 22) is configured, upon relative movement with respect to the other cap portion (e.g. first cap portion 20), to break the integrity of the frangible wall portion 40, to open the chamber. For example, the second cap portion 22 comprises a cutting or piercing element 42 for breaking the integrity. A single cutting/piercing element 42 may be used, or plural cutting/piercing elements 42 may be used if preferred (for example, two, three, four, or more).

As already described, the second cap portion 22 may be coupled to the first cap portion 20 by a rotating or screw-threaded coupling. The second cap portion 22 may have the form of a nut with an interior thread (not shown graphically but denoted at 44) for connection to an exterior facing thread (not shown graphically, but denoted at 46) on a depending wall 48 of the first cap portion 20. Additionally or alternatively, the second cap portion 22 may have the form of an annular nut carrying the cutting/piercing element 42. Additionally or alternatively, the thread of the nut may be the cutting/piercing element 42 if the thread profile is sufficiently sharp. As the first cap portion 20 is screwed into engagement with the tube, the second cap portion 22 may be restrained against rotation. The resulting relative rotation between the first and second cap portions 20 and 22 causes the cutting/piercing element 42 to press against, or wipe across, the frangible wall portion to break its integrity. For example, the second cap portion 22 may ride upwardly towards the frangible wall portion 40 (as illustrated in FIG. 3), or it the second cap portion 22 may be configured to ride downwardly (in a similar manner to the embodiments of FIGS. 1 and 2) towards a frangible wall portion positioned towards the lower end of the wall 48.

It will be appreciated that by incorporating the cutting/piercing element 42 into the assembly of the cap 12, there is no need to provide an exposed cutting/piercing element in the mouth of the tube, where it may pose a risk to the lips, mouth or other body member of a donor while donating the bodily fluid sample. Instead, both the chamber of preservative solution (which may be toxic), and the cutting/piercing element can be shielded from the don or.

Various forms of relative movement between the first and second cap portions 20 and 22 may be envisaged, while still providing the benefit that the chamber and the cutting/piercing element 42 are both incorporated in the cap itself. The disclosure is not limited only to relative rotational movement (including screw threaded movement) between the first and second cap portions 20 and 22, although relative rotational movement may provide additional advantages by being related to the movement to screw the cap on to the tube.

Figure 4:
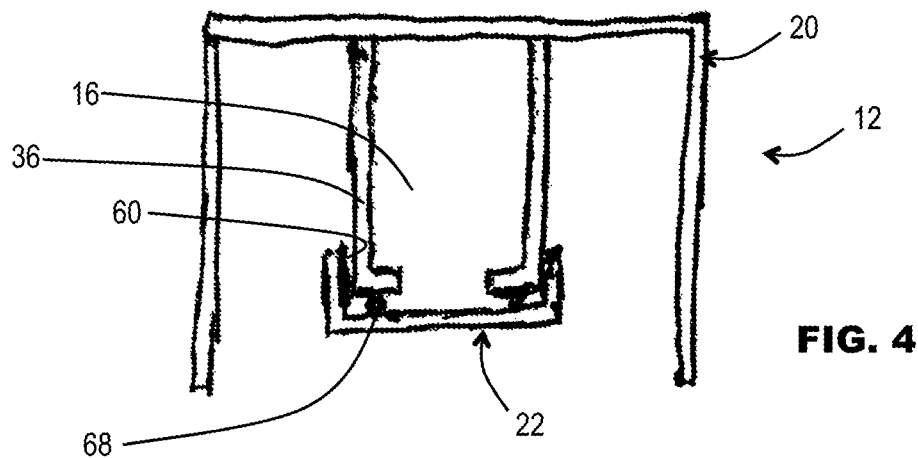
FIG. 4 is a schematic section through a cap of a further example of sample collection device, according to some embodiments.
Figure 5A:
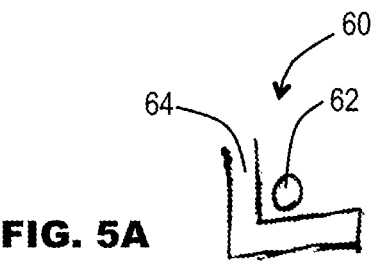
FIGS. 5A and 5B are schematic illustrations of a bayonet style coupling, according to some embodiments.
Figure 5B:
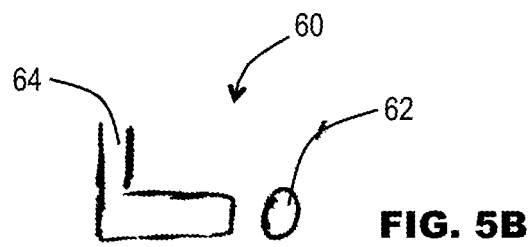

Referring the example of FIGS. 4 to 7, the second cap portion 22 may be similar to that of FIGS. 1 and 2, except that:

(i) In some embodiments, the second cap portion 22 is coupled to the first cap portion 20 by a bayonet coupling (indicated generally at 60 in FIG. 4). The bayonet coupling may comprise one or pins or projections 62 carried by one cap portion engageable with a respective complementary track or tracks 64 carried by the other cap portion. Purely by example, the projection(s) 62 may be carried by the first cap portion 20 and the track(s) 64 carried by the second cap portion 22, but the two may be reversed according to design preference. The track 64 may by a guide rib or fence against which the projection 62 bears, or the track 64 may be slot within which the projection 62 slides.

(ii) Whether or not a bayonet connection is used, in some embodiments, the second cap portion 22 may remain attached to the first cap portion 20 when the second cap portion 22 is moved to an open position.

For example, the cap 12 may comprise a disengagement stop (indicated generally at 66) to prevent (or at least obstruct) disengagement of the second cap portion 22 from the first cap portion 20. The disengagement stop 66 may be integrated into the bayonet coupling (or other coupling, whether rotational or not), or the disengagement stop 66 may be a distinct coupling arrangement between the first and second cap portions 20 and 22.

Preventing (or at least obstructing) separation of the first and second cap portions 20 and 22 can stop the second cap portion 22 from dropping down entirely into the sample collection space 18 of the tube 14. As explained above, this can reduce the risk of the second cap portion interfering with good mixing of the reagent and the collected sample.

Figure 6:
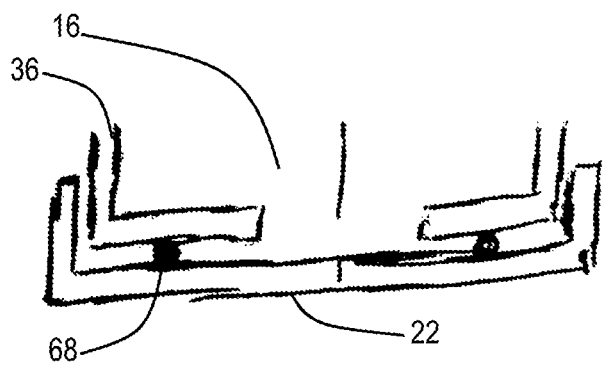
FIG. 6 is a schematic section showing the second cap portion of FIG. 4 in a closed position, according to some embodiments.
Figure 7:
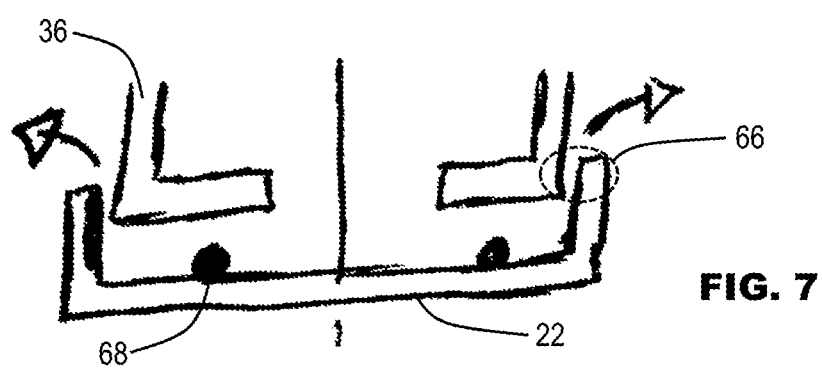
FIG. 7 is a schematic section showing second cap portion of FIG. 6 in an open position, according to some embodiments.

(iii) The cap 12 may comprise an elastomeric sealing element 68, for example, of silicone. The sealing element 68 may be compressed when the second cap portion 22 is in its closed state on the first cap portion (FIG. 6). The sealing element 68 may generate a return force tending to urge the second cap portion 22 away from the first cap portion 20 when the bayonet coupling is relaxed (FIG. 7). Such an arrangement may automatically urge the second cap portion to move towards its open position.

In the open position of the second cap portion 22 (FIG. 7), the reagent may escape from the chamber 16 either through escape channels formed in the coupling between the first and second cap portions 20 and 22 (as indicated by the arrows), or through escape apertures formed in the second cap portion (not shown).

Figure 8:
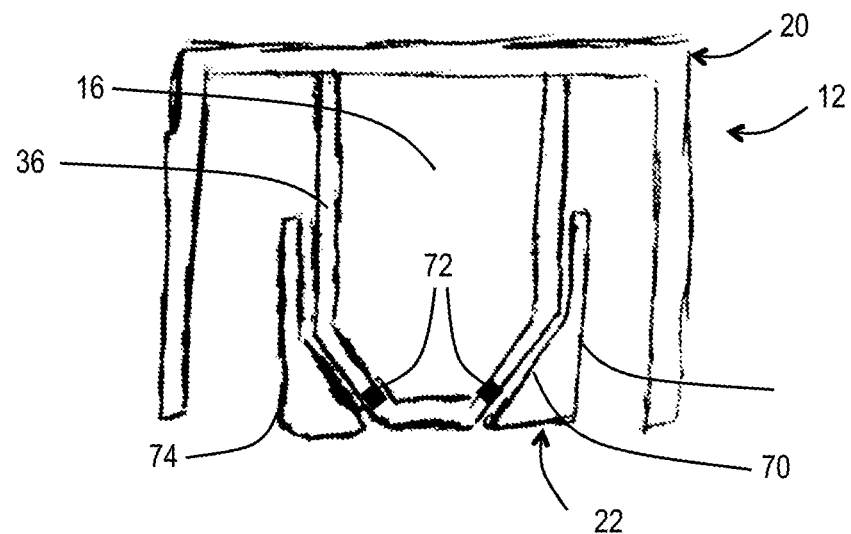
FIG. 8 is a schematic section through a cap of a further example of sample collection device, according to some embodiments.
Figure 9:
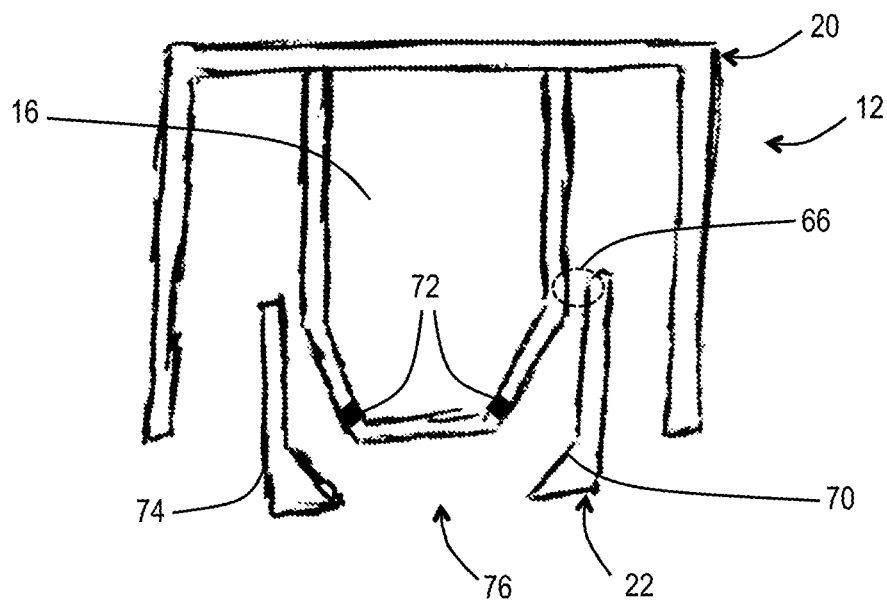
FIG. 9 is a schematic section through the cap of FIG. 8, but showing the second cap portion displaced to an open position, according to some embodiments.

Referring to the example of FIGS. 8 and 9, in some embodiments the coupling between the first and second cap portions 20 and 22 may be "passive". The coupling may permit at least a range of predetermined movement, without the coupling being response to actively move the second cap portion 22 relative to the first cap portion.

For example, the second cap portion 22 may have the form of a pull-down cover that is displaceable from a closed position (FIG. 8) to an open position (FIG. 9). The cover has a interior seal surface 70 configured to seal around apertures 72 formed in the inner wall 36 when the second cap portion 22 is in its closed position. The inner wall 36 may have a tapered lower end at which the apertures 72 are positioned. The inner wall 36 may include a floor defining a closed shape for the chamber 16.

An additional active displacement mechanism may be provided for causing the second cap portion 22 to move downwardly with respect to the first cap portion 20 when the cap 12 is placed on to a tube. In some embodiments, the active displacement mechanism may, for example, be a threaded coupling between the exterior surface 74 of the second cap portion, and a complementary thread of the second engager 26. Alternatively, a lever arrangement (not shown) in the cap 12 may be responsive to fitting the cap 12 to the tube 14, in order to generate a force urging the second cap portion 22 downwardly.

In the open position of the second cap portion 22, the seal surface 70 is moved away from blocking the aperture 72, thereby allowing the reagent to escape through the apertures 72. The second cap portion 22 may include one or more openings 76 through which the reagent may enter the sample collection space of the tube.

The coupling between the first and second cap portions 20 and 22 may include a disengagement stop (again indicated generally at 66 in FIG. 9) for preventing (or at least obstructing) disengagement of the second cap portion 22 from the first cap portion.

As an alternative to the second cap portion 22 displacing downwardly with respect to the first cap portion, in some embodiments, the second cap portion 22 may be configured to be displaced upwardly (for example, by engagement with a second displacer 26 configured to push upwardly on the second cap portion 22).

In the example of FIGS. 8 and 9, if preferred, the first and second cap portions 20 and 22 may be coupled by means of an active coupling, such as a threaded coupling or a bayonet coupling.

Figure 10:
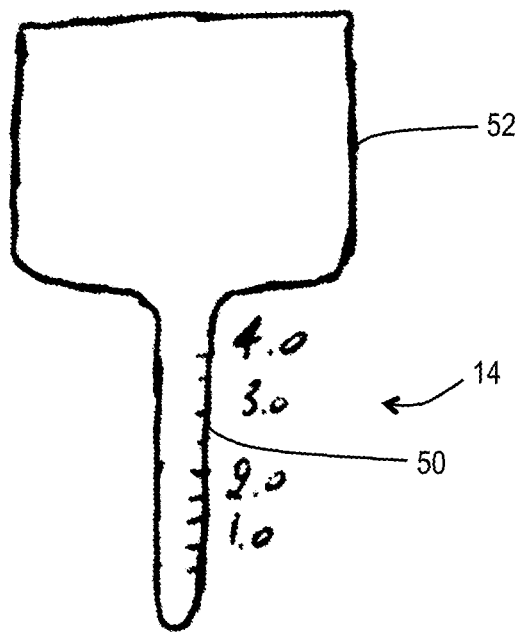
FIG. 10 is a schematic section through a tube of a further example of sample collection device, according to some embodiments.
Figure 11:
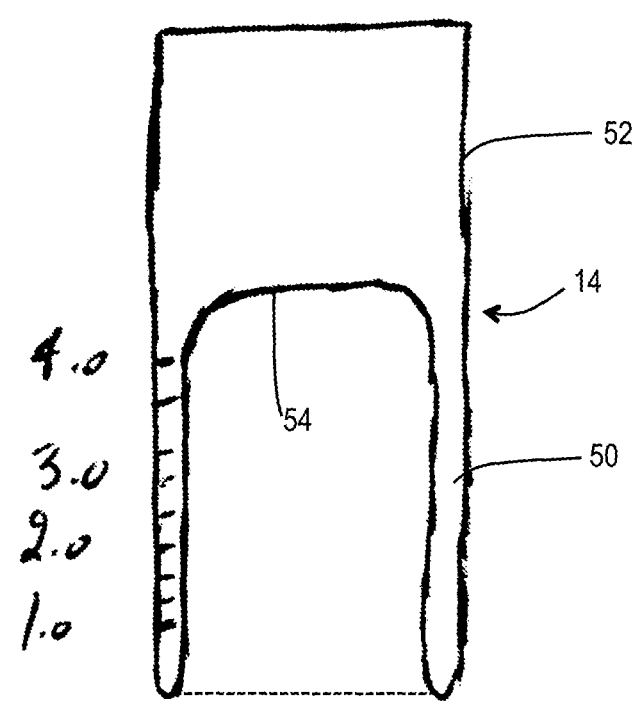
FIG. 11 is a schematic section through a tube of a further example of sample collection device, according to some embodiments.
Figure 12:
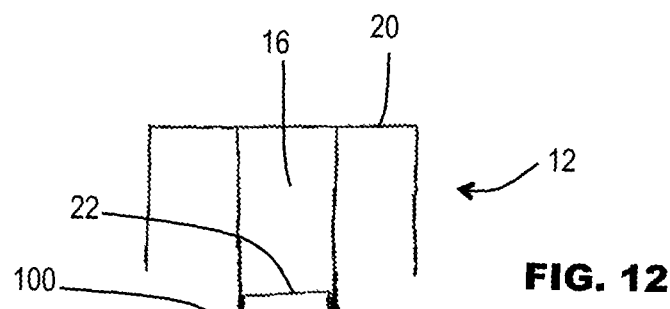
FIG. 12 is a schematic sectional view of a cap in a further embodiment.
Figure 13:
FIG. 13 is an underside view of the second cap portion of the cap of FIG. 12, according to some embodiments.
Figure 14:
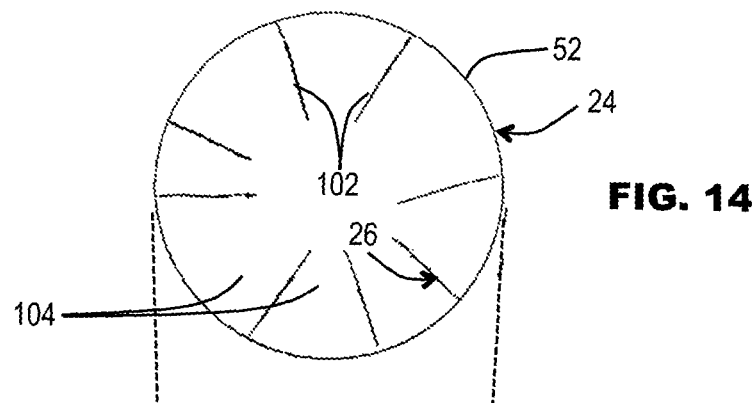
FIG. 14 is a top view of the mouth of a tube for use with the cap of FIG. 12 according to some embodiments.
Figure 15:
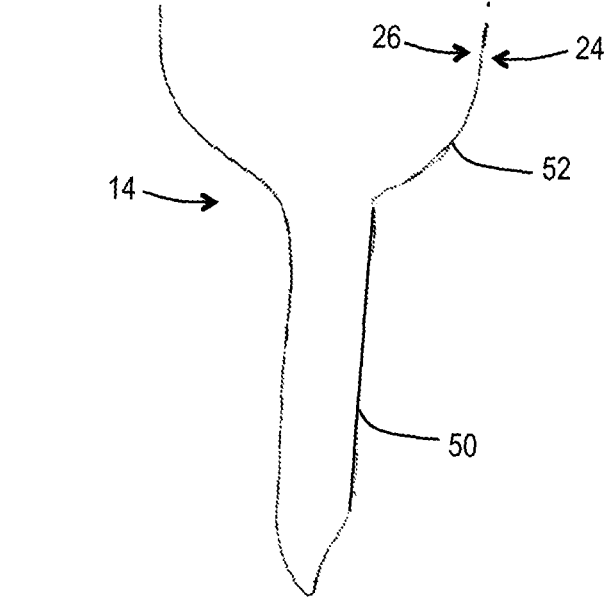
FIG. 15 is a schematic side section through the tube of FIG. 14, according to some embodiments.
Figure 16:
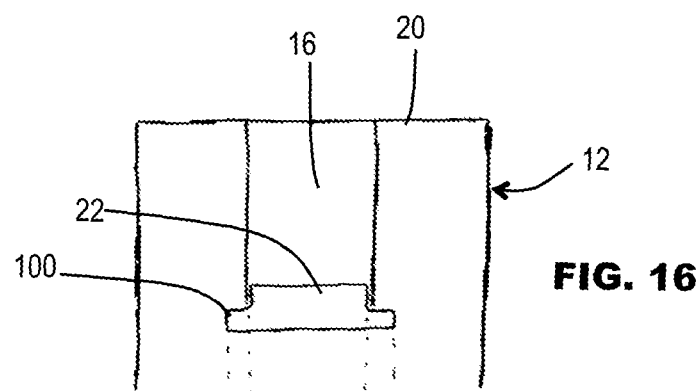
FIG. 16 is a schematic sectional view of a cap in a further embodiment.
Figure 17:
FIG. 17 is an underside view of the second cap portion of the cap of FIG. 16, according to some embodiments.
Figure 18:
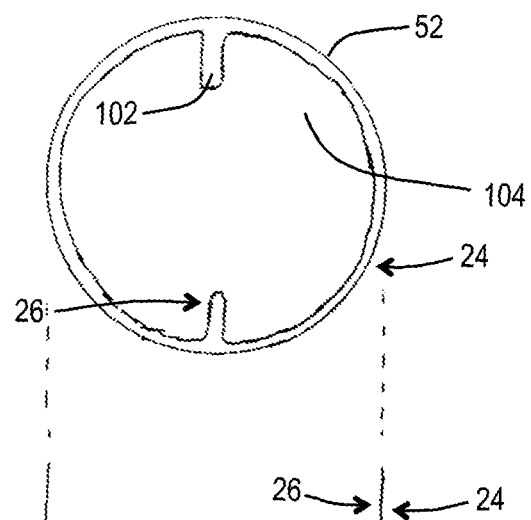
FIG. 18 is a top view of the mouth of a tube for use with e cap of FIG. 16, according to some embodiments.
Figure 19:
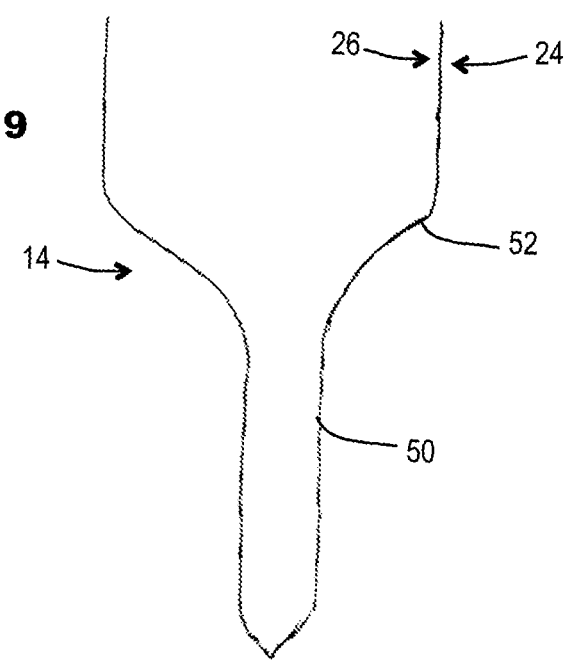
FIG. 19 is a schematic side section through the tube of FIG. 18, according to some embodiments.

Referring to FIGS. 10 and 11, whether or not the cap incorporates any of the above cap features, the tube 14 may have a shape including a sample collection portion 50 having a smaller interior cross-sectional area than at the mouth 52 for receiving the cap (not shown). Providing a small cross-sectional area enables a finely graduated fill scale and/or fill line to be provided that may be easily read and judged for collecting small amounts of bodily fluid. For example, for saliva, the collected sample may be between about 1 ml and 6 ml in volume. It may be desirable to indicate a graduation for each 2 ml, or 1 ml, or half ml, or even smaller. Alternatively, it may be desirable to have only one graduation indicating either a volume of 2 ml, 4 ml, 6 ml, or any volume between 1 and 6 ml. In the non-limiting example illustrated, the scale is graduated between 1 and 4 ml. Alternatively, a (e.g. single) fill line may also be provided instead of one or more specific measurement graduations.

Providing a fill scale and/or fill line that is clear to see and/or judge is greatly facilitated by having a small interior cross-sectional area, without compromising the size of the mouth of the tube.

A fill scale and/or fill me may be advantageous in some embodiments disclosed herein, where the second cap portion 22 may translate towards, or drop towards, the sample collection space. By avoiding overfilling the sample, any risk of the tube overflowing may be avoided. Overflow could otherwise result from release of the reagent into an tube overfilled with the bodily fluid sample (the reagent may be toxic), and/or from the action of the second cap portion 22 dropping or translating towards the sample collection space, potentially reducing the available volume.

The region of small cross-sectional area may also prevent (in some embodiments) dropping down of the second cap portion 22 into the small cross-sectional area sample collection space.

By way of example, the cross-sectional area of the sample collection portion may be no more than about 50% of the mouth cross-sectional area, optionally no more than about 45% of the mouth cross-sectional area, optionally no more than about 40% of the mouth cross-sectional area, optionally no more than about 35% of the mouth cross-sectional area, optionally no more than about 30% of the mouth cross-sectional area, optionally no more than about 25% of the mouth cross-sectional area, optionally no more than about 20% of the mouth cross-sectional area, optionally no more than about 15% of the mouth cross-sectional area, optionally no more than about 10% of the mouth cross-sectional area, optionally no more than about 5% of the mouth cross-sectional area.

Additionally or alternatively, in some embodiments, the cross-sectional area of the sample collection portion may be at least about 70 mm$^2$, optionally at least about 200 mm$^2$, optionally at least about 300 mm$^2$. Additionally or alternatively to any of these values, in some embodiments, the cross-sectional area of the sample collection portion may be not substantially greater than about 700 mm$^2$, optionally not substantially greater than about 500 mm$^2$, optionally not substantially greater than about 400 mm$^2$. In some embodiments, the cross-sectional area may be between about 70 mm$^2$ and about 700 mm$^2$, optionally between about 200 mm$^2$ and about 500 mm$^2$, optionally between about 300 mm$^2$ and about 400 mm$^2$.

In the example of FIG. 10, the sample collection portion 50 may have a thin columnar shape. In the example of FIG. 11, the sample collection portion 50 may have an annular or toroid shape defined (for example) by an inverted-U-shape floor 54 of the tube 14. Such a shape may be more stable than a thin columnar portion of FIG. 4, and may enable the tube to be placed upright on a table (for example if desired).

The concept of a thin columnar shape of sample collection portion 50 of the tube 14 is also illustrated in some further examples below, although these further embodiments are not limited only to such a shape. The tube 14 may have a sample collection portion 50 of thin columnar shape, and a wider mouth region 52. The cap 12 may have a first cap portion 20 defining a downwardly depending chamber 16 with an aperture at the bottom closed by a second cap portion 22. The second cap portion 22 may be releasable from the first cap portion 20 by relative rotation between the cap portions 20 and 22. For example, the second cap portion 22 may be threadedly coupled to the first cap portion, and unscrewed therefrom in response to the relative rotation. A first engager 24 on the tube mouth 52 may threadedly engage the first cap portion 20. A second engager 26 on the tube mouth 52 may engage the second cap portion 22 to restrain the second cap portion 22 against rotation when the first cap portion 20 is screwed on to the tube mouth 52.

Some embodiments address a relationship between (i) ease of attaching the cap 12 to the tube, and (ii) the angular screw thread length available for engaging/releasing the second cap portion 22 with respect to the first cap portion 20. The following examples use a design criterion that a first angular thread length for securing the cap 12 to the tube 14 (for example, and defining the engagement between the first cap portion 20 and the first engager 24) corresponds to rotation through about a single turn (e.g. about 360°). Such an engagement thread length may provide good usability for many different users, while still providing sufficient engagement to reliably seal the tube 14 closed. However, longer first thread lengths, for example, about a turn and a half, or more, or shorter first thread lengths, for example, about a three-quarter turn, or about a half turn, or less, may also be used as desired.

Referring to FIGS. 12-15, in some embodiments, it may be desirable to have a relatively long second angular engagement thread length (measured in rotation angle) between the first and second cap portions 20 and 22, for example, not substantially shorter than the first engagement thread length referred to above, for example, corresponding to about one full turn. This may be facilitated by arranging the second engager 26 to engage the second cap portion 22 before, or substantially at the same time as, or at least not substantially later than, engagement between the first engager 24 and the first cap portion 20. Such relatively early engagement by the second engager 26 can ensure that the second cap portion 22 is restrained against rotation almost immediately when the first cap portion 20 is rotated, and thereby enable at least the majority, or substantially all, of the rotation movement of the first cap portion 20 to be available for generating the relative rotation between the first and second cap portions 20 and 22 for opening the chamber.

In FIGS. 12-15, the first cap portion 22 is positioned below the mouth of the first cap portion 20. In use, abutments 100 of the second cap portion are manually keyed with an arrangement of projections 102 defining the second engager 26 in the mouth portion 52 of the tube 14, before the first cap portion 20 engages the screw thread of the first engager 24. The arrangement of projections 102 defines angular spaces 104 that are not substantially larger than the angular or circumferential width of the abutments 100, to provide engagement without substantial lost rotation or backlash. For example, the spaces 104 may be less than twice the angular width of the abutments 100, optionally less than 150%, optionally less than 125%. In use, the user may manually key the abutments 100 with the spaces 104 between the projections 102 as an initial stage of fitting the cap 12 to the tube 14. The position of the second cap portion 22 below the mouth of the first cap portion 20 may facilitate easy viewing to arrange the keyed alignment. Thereafter, the user may slide the cap 12 axially further towards the tube 14 to engage the first cap portion 20 with the first engager 24 and permit screwing of the first cap portion 20 on to the tube 14. As already described, the early engagement between the second engager 26 and the second cap portion 22 can avoid significant "lost rotation" in the relative movement between the first and second cap portions 20 and 22. It can also ensure that the user feels a generally uniform resistance during screwing the cap 12 on to the tube 14 because the engagement of the second engager 26 is not delayed.

Referring to FIGS. 16-19, in some embodiments, it may be desirable to accommodate screwing of the cap 12 on to the tube 14 without the user having to manually key together the second engager 26 and the second cap portion 22. This may be facilitated by increasing the angular spaces 104 between the projections 102, and/or reducing the number of the projections 102 defining the second engager 26, and/or by shortening the angular width of the abutments 100. For example, the number of projections 102 may be four or less, optionally three or less, optionally two or less, optionally one. In the example of FIGS. 16-19, two projections 102 are illustrated, separated by angular spaces 104 each of at least about 170°, for example, approaching 180°. Such an arrangement may provide a large angular position range over which the abutments 100 may enter a space 104 between the projections 102 to loosely key the second engager 26 and the second cap portion 22. Such an arrangement may avoid any need for the user to manually key the second engager 26 and the second cap portion 22, because the two components can fit together in almost any relative angular orientation. The second cap portion 22 may be recessed (or at least non-projecting) with respect the mouth of the first cap portion 20.

A consequence of the large angular spaces 104 may be that significant so-called lost rotation or backlash exists between the second engager 26 and the second cap portion 22, before the second cap portion 22 is restrained from rotation during screwing of the cap 12 on to the tube 14. For example, in the illustrated example, the lost rotation may be up to about a half turn, (for example, up to between about 170° and about 180°). The second angular thread length (between the first and second cap portions 20 and 22) may be designed to be less than the first angular thread length (between the first engager 24 and the first cap portion 20) by at least a corresponding amount. For example, the first angular thread length for screwing the cap 12 on the tube 14 may be about one full turn (e.g. about 360°), and the second angular thread length may be about a half-turn (e.g. about 180°). The amount of relative rotation available for engaging/releasing the first and second cap portions 20 and 22 may be reduced compared to the preceding embodiment, but with easier fitting of the cap 12 to the tube 14 without having to manually key the second cap portion 22 with the second engager 26.

Referring to FIG. 20, in some embodiments, the first and second cap portions 20 and 22 may be formed or joined together as a unitary item. A frangible wall portion 110 (e.g. an integral frangible wall portion) may be breakable to release the second cap portion 22 from the first cap portion 20 in response to relative movement (for example, relative rotation between the cap portions 20 and 22. The cap portions 20 and 22 may be regarded as being relatively movable at least in use. Additionally or alternatively, the cap portions 20 and 22 may be regarded as being in use moved one relative to the other. The release or opening of the chamber 16 may be similar to a twist-to-break-open design, in which a frangible wall portion is designed to fail or break in response to forced twisting of one portion relative to another. The first and second cap portions 20 and 22 may be formed as an injection molded body.

In some embodiments, the second cap portion 22 may comprise relatively strong and/or large fins 112 to enable sufficient torque to be applied to the second cap portion 22 by the second engager 26 to restrain the second cap portion 22 from rotation and break the frangible wall portion 110.

In some embodiments, a protective sleeve 113 may be provided for protecting the second cap portion 22 from accidental breakage prior to intended use. The protective sleeve 113 may be manually removable by the user at the time of use, or it may be intended to remain in place, and be received within the mouth portion of the tube 14.

In some embodiments, the cap 12 may further comprise a filling port 114 that is distinct from the aperture for releasing the reagent, and/or distinct from connection to the second cap portion 22. Such a filling port 114 may be especially suitable when the first and second cap portions 20 and 22 are integrally formed together to define a closed-bottom chamber 16, but the filling port 114 may also be used in any of the other embodiments described herein. The filling port 114 may enable the reagent to be introduced into the chamber 16 independently of the dispensing aperture and/or the second cap portion. In some embodiments, the filling port 114 may be closed by a press-fit (e.g. snap fit) cover or plug 115, or by any other suitable closure.

Referring to FIGS. 21 and 22, in some embodiments, the second cap portion 22 comprises a movable wall of a closed bladder or other variable volume and/or variable shape chamber 116. For example, the chamber 116 may have a bellows or accordion design, including a wall portion 118 that is intended to fold or collapse to provide variable volume and/or shape. The cap 12 may further comprise a cutting and/or piercing element 42 for breaking the integrity of a frangible wall portion of the chamber 116 in response to movement of the movable wall (e.g. second cap portion 22). In some embodiments, the cutting/piercing element 42 may be provided inside the chamber 116. Such an arrangement provides considerable safety advantages by avoiding any exposed sharp edge prior to use. Such an arrangement can also accommodate the cutting/piercing element within a relatively low package profile. Alternatively, the cutting/piercing element 42 may be arranged outside the chamber 116.

In some embodiments, the chamber 116 (and optionally the cutting/piercing element) may be produced as a self-contained module independently of a cap shell 120. This can allow the chamber module to be filled with reagent by a separate operation before the module is mounted to the cap shell 120. For example, the module may be attached to a mounting 122 of the cap shell by any suitable fixing technique, for example, by adhesive, welding, or an interference fit.

In use, when the cap 12 is fitted to the tube 22, the movable wall (second cap portion 22) may bear against an abutment defining the second engager 26 in the mouth portion 52 of the tube 14. The abutment causes the movable wall to displace upwardly into contact with the cutting/piercing element 42. The element 42 breaks the integrity of the movable wall, thereby releasing the reagent from the chamber 116.

The cap 12 may be attachable to the tube 14 by any suitable attachment, for example, a screw thread, a bayonet connection, or a press-fit (e.g. a snap-fit).

In some embodiments, a protective sleeve 113 may be provided for protecting the chamber 116 from accidental deformation or breakage prior to intended use. The protective sleeve 113 may be manually removable by the user at the time of use, or it may be intended to remain in place, and be received within the mouth portion of the tube 14. Additionally or alternatively, the chamber 116 may be disposed within a protective case (not shown), or behind a protective wall (not shown). The case or wall may include one or more apertures through which respective pushers or plungers may bear on the movable wall without exposing the movable wall itself. The reagent when released from the chamber 116 may be dispensed through these (or other) apertures.

Although the present embodiment illustrates the chamber 116 installed within the cap, in other embodiments, the chamber 116 may be installed within the tube, and configured to be deformed upon fitting of the cap to the tube.

Figure 23:
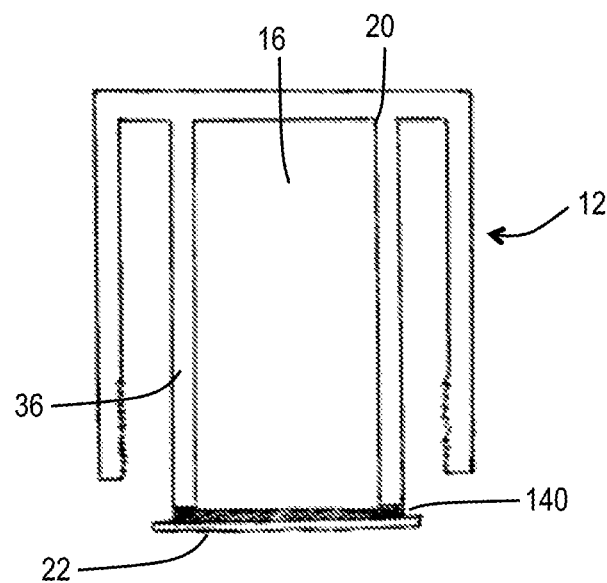
FIG. 23 is a schematic section showing a cap comprising a welded foil cap portion, according to some embodiments.
Figure 24:
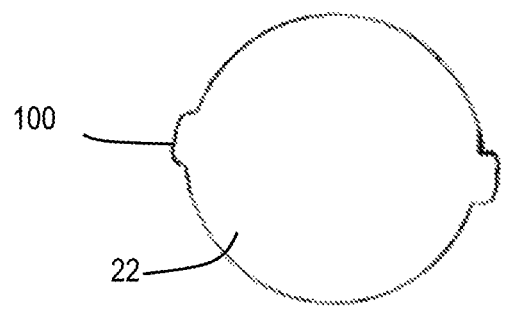
FIG. 24 is a schematic underside view of the second cap portion of the cap of FIG. 23, according to some embodiments.

Referring to FIGS. 23 and 24, in some embodiments, the second cap portion 22 may be provided as a foil or plug that is welded (at region 140) to the first cap portion 20 (e.g. to the depending wall 36). The second cap portion 22 may, for example, comprise a laminate of plastics and metal foil, optionally reinforced with a plug body or frame. The second cap portion 22 may be attached to the first cap portion 20 by any suitable welding technique, such as ultrasonic welding. Welding may provide a convenient and low-cost technique for establishing a seal closing the chamber 16. In the illustrated form, the depending wall 36 is optionally slightly longer than the outer body of the cap 12, in order to facilitate welding.

The second cap portion 22 may comprise abutments 100 which function in the same way as described earlier. In use, when the cap 12 is screwed to the tube (14, not illustrated in FIGS. 23 and 24), the abutments 100 are engaged by complementary profiles of the tube 14 to restrain the second cap portion 22 from rotation. The resulting torsion breaks the seal to release the contents of the chamber 16 into the tube. In some embodiments, the torsion may break the integrity of the weld join, such that the second cap portion 22 is disengaged from the first cap portion. Additionally or alternatively, in some embodiments, the torsion may rupture or tear the foil material of the second cap portion, thereby creating openings to release the contents of the chamber 16. Optionally, the foil may have predetermined lines or zones of weakness defining intended tear locations.

Use of a welded second cap portion may provide some advantages in enabling a reliable seal to be established quickly and simply, using known food container techniques. In particular, it may avoid the need and the tooling cost of molding screw threads for coupling the first and second cap portions. It may also avoid the need for incorporating any cutting or piercing element.

Figure 25:
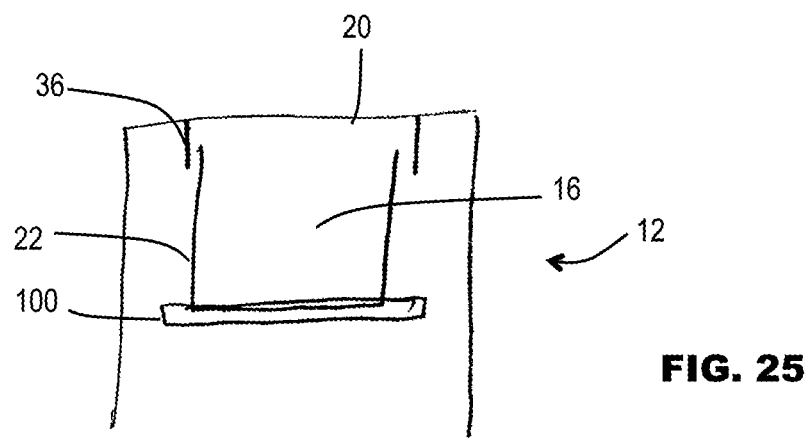
FIG. 25 is a schematic section showing a cap comprising a cup-shaped second cap portion, according to some embodiments.

Referring to FIG. 25, in some embodiments, second cap portion 22 may, instead of being relatively flat, have a substantially cup form. The second cap portion 22 may, for example, be taller than the depending wall 36 of the first cap portion 20. The coupling between the first and second cap portions may be active or passive. The coupling may be rotatable, for example, a threaded coupling or a bayonet coupling. The second cap portion 22 may, for example, include the abutments 100 referred to above for cooperating with complementary elements of the tube, to restrain the second cap portion 22 against rotation during fitting of the cap 12 to the tube.

In use, this embodiment may function similarly to the preceding embodiments. In response to relative movement (e.g. rotation) between the first and second cap portions 20 and 22 upon fitting the cap 12 to a tube, the second cap portion 22 may disengage from the first cap portion 20. Optionally the second cap portion 22 may drop down at least partly towards or into the tube. Optionally the second cap portion 22 may lean or tip over to promote release of the agent into the tube. Optionally, mixing of the agent with the collected sample may be enhanced by the user manually shaking the sample collection device after having fitted the cap 12 to the tube.

Figure 26:
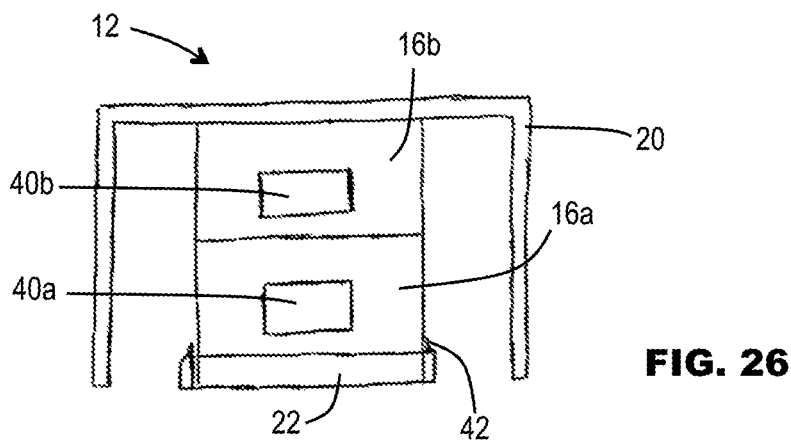
FIG. 26 is a schematic section showing a cap comprising plural chambers, according to some embodiments.
Figure 27:
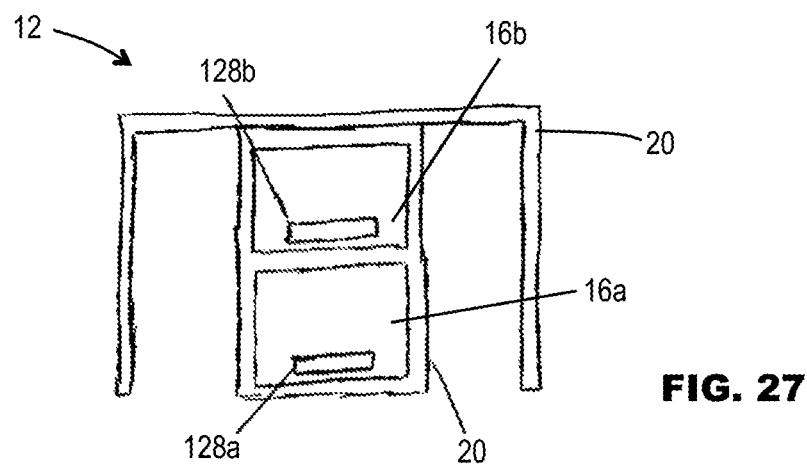
FIG. 27 is a schematic section through a cap comprising multiple chambers, showing the first cap portion in isolation, according to some embodiments.
Figure 28:
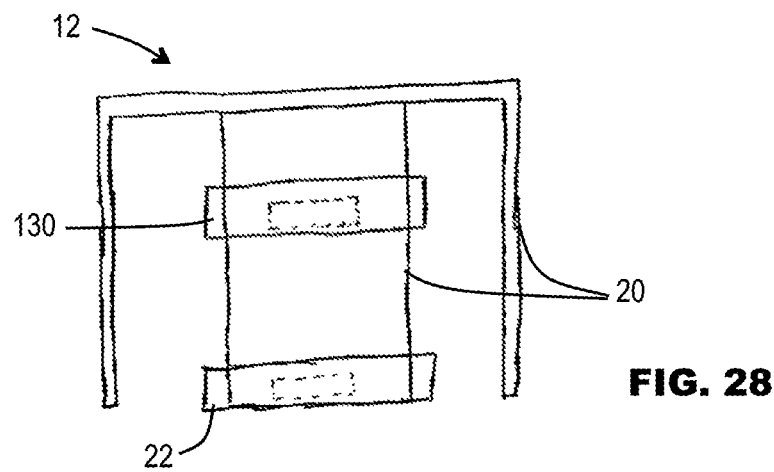
FIG. 28 is a schematic section showing the cap of FIG. 27 fitted with respective cap portions for closing/opening the plural chambers, according to some embodiments.

Although not illustrated above, any of the preceding embodiments may optionally comprise plural chambers 16 (or 116) for containing plural reagents or plural reagent components. Some embodiments explicitly incorporating plural chambers 16a and 16b are shown in FIGS. 26-28.

In some embodiments, the plural chambers first and second chambers 16a and 16b) are defined by respective compartments in the first cap portion. In some embodiments, the compartments may be one above the other (as illustrated). Alternatively or additionally, compartments may be arranged side by side. The number of compartments may be two, or three, or more as desired.

Plural chambers 16a and 16b may enable plural different reagents to be stored separately, and/or plural reagent components to be stored separately. For example, certain reagents or components may have a longer shelf-life when stored separately than when mixed together, and/or may be less sensitive to external influence such as temperature when stored separately, and/or may form an active reagent that is only active for a limited period of time once mixed together.

If desired, the cap 12 may be configured to release the contents of the chambers 16a and 16b generally at the same time as each other, or sequentially one after the other. Sequential release may be especially suitable when it is desired to contact the sample with one reagent or component before the other.

In some embodiments, the mechanism for opening each chamber 16 to release its contents may be similar to any of the release mechanisms described above. In particular the cap 12 may comprise portions that are relatively movable with respect to one another, and/or in use are moved one relative to another, in response to fitting the cap 12 to the tube 14. The relative movement between the cap portions may open each chamber 16a and 16b (optionally sequentially) to release the chambers' contents.

Referring to FIG. 26, in some embodiments, each chamber 16a and 16b may have an aperture in a wall of the first cap portion 20, closed by a frangible wall portion 40a and 40b, similar to the frangible wall portion 40 described above. The second cap portion 22 may be coupled to the first cap portion 20 by a rotating or screw-threaded coupling. The second cap portion 22 may comprise one or more cutting/piercing elements 42 configured to break the integrity of the frangible wall portions 40a and 40b as the second cap portion 22 moves rides upwardly in response to relative rotation. The second cap portion 22 may optionally be configured to open the chambers 16a and 16b sequentially one after the other responsive to the axial movement. Although the second cap portion 22 is illustrated as being initially at the bottom (mouth) of the cap 12, and configured to ride upwardly into the cap, the second cap portion 22 may if desired be positioned initially at the upper end, and configured to ride downwardly towards the cap mouth.

Referring to the alternative embodiment of FIGS. 27 and 28, the first cap portion 20 is similar to FIG. 26, except that the apertures 128a and 128a are not covered by frangible wall portions. Instead, each aperture is closed by a respective cap portion, for example, each in the form of a nut or other annular member. The aperture 128a of chamber 16a may be closed by a second cap portion 22, and the aperture 128a of chamber 16b may be closed by a further (e.g. third) cap portion 130. The cap portions 22 and 130 may be configured to move relative to the first cap portion 20, to uncover the respective apertures of the chambers 16a and 16b when the cap 12 is fitted to the tube 14.

For example, in some embodiments, the second cap portion 22 may be caused to rotate first upon fitting the cap 12 to the tube 26, to move upwardly into the cap 12, and uncover the aperture 128a of the first chamber 16a, to release its contents. Continued relative rotation causes the second cap portion 22 to bear against and similarly move the third cap portion 130, in order to uncover the aperture 128a of the second chamber 16b, to release its contents sequentially after the first chamber 16a. As an alternative to the above, both the second and third cap portions could be caused to rotate simultaneously, in order to release the contents of the chambers 16a and 16b together. As a further alternative, the second and third cap portions could be replaced by a single cap portion having an axial length sufficient to cover the apertures 128a and 128a of both chambers 16a and 16b. The single cap portion may be shaped to provide simultaneous or sequential opening of the chambers 16a and 16b in response to relative rotation, according to design preference.

Figure 29:
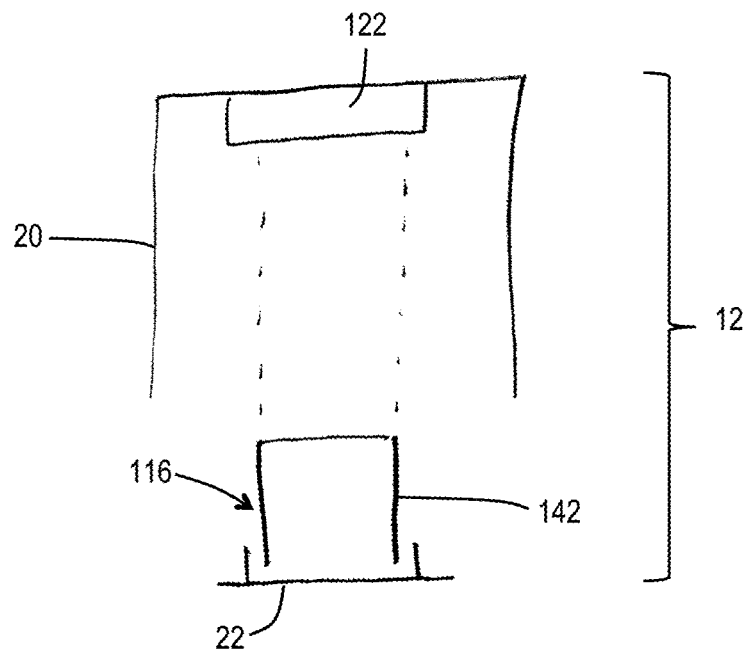
FIG. 29 is a schematic section through a cap comprising a modular chamber, according to some embodiments.

Referring to FIG. 29, the principles of producing the agent containing chamber 116 as a self-contained module independently of a cap shell 120, and previously described with reference to the embodiment of FIGS. 21 and 22, may be applied to any of the other types of chamber 16 and cap portions 20 and 22 described hereinbefore. FIG. 29 illustrates, for example, generally a chamber module 116 comprising an inverted cup-shaped body 142, and a second cap portion 22.

The coupling between the body 142 and the second cap portion 22 may be active or passive. The coupling may be rotatable, for example, a threaded coupling or a bayonet coupling. The second cap portion 22 may, for example, include the abutments 100 referred to above for cooperating with complementary elements of the tube, to restrain the second cap portion 22 against rotation during fitting of the cap 12 to the tube.

The chamber module 116 may be attached to a mounting 122 of the cap shell 20 by any suitable fixing technique, for example, by adhesive, welding, a screw thread, or an interference fit. Especially in the case of the second cap portion 22 being responsive to relative rotation, the fixation at the mounting may optionally be of a non-rotation type that does not, after fixing, permit relative rotation between the cap shell 120 and the body 142.

Producing the chamber 116 in a self-contained module form may provide several potential advantages, in some embodiments. For example:

(iv) the chamber module 116 can be filled with re-agent by a separate (e.g. automated) operation before the module is mounted to the cap shell 120. This may simplify filling production.

(v) the tooling for molding the components for the cap 12 may be simplified, because the cap is built from several parts that are, individually, easier to mold than may be a more complicated integral molding (vi) the technique may permit modular moldings to be used that may be difficult to mold in integral form. For example, as illustrated in FIG. 29, the engagement between the second cap portion 22 and the body 142 may be on an external face of the body 142. The molding used for the body 142 may, for example, have an exterior thread. Such an external thread may be molded more easily when the body 142 is made separately from the cap shell 120.

In the embodiments of FIGS. 21, 22 and 29, the cap shell 120 and/or a portion (e.g. 142) of the chamber module 116 to be affixed to the cap shell 120 may be regarded as a first cap portion. When both parts in combination are considered to be comprised in the first cap portion, such an embodiment may illustrate a cap portion constructed from plural parts assembled together.

Figures 30, 31:
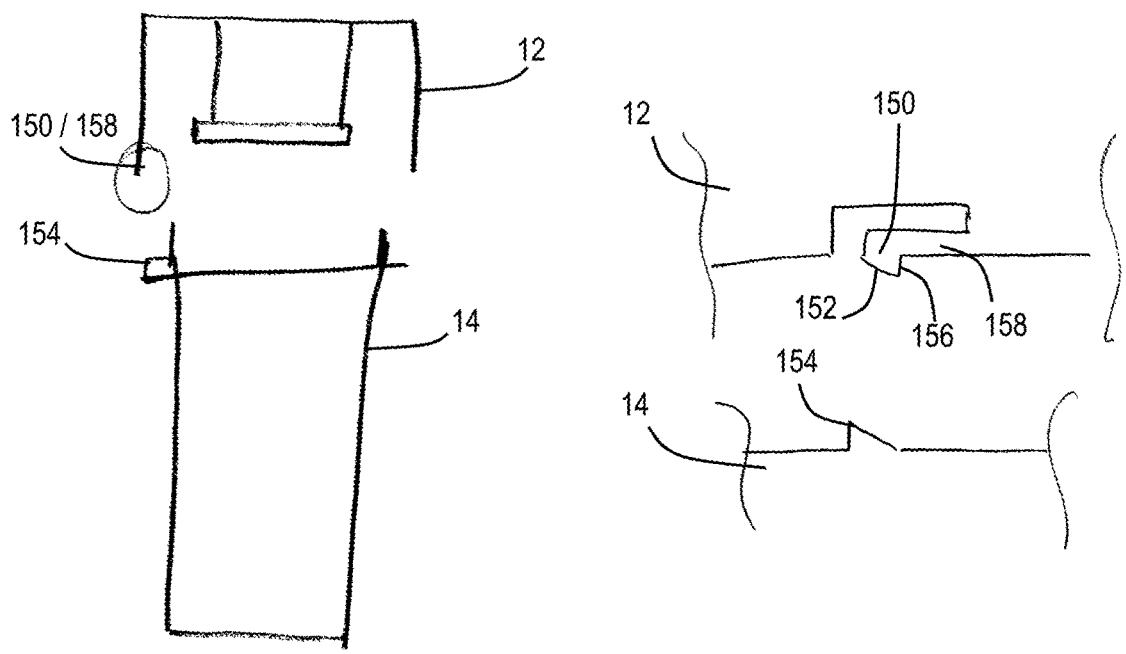
FIG. 30 is a schematic section showing a sample collection device including a lock device, according to some embodiments.
FIG. 31 is a schematic drawing illustrating a detail of the lock device from FIG. 30, according to some embodiments.
Figure 32:
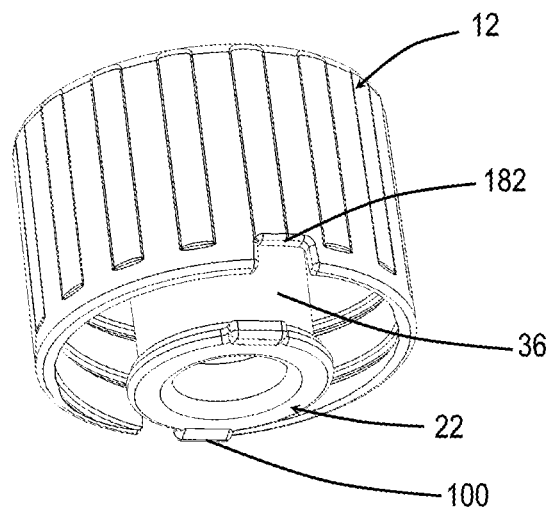
FIG. 32 is a schematic perspective view showing a cap of a further embodiment, according to some embodiments.
Figure 33:
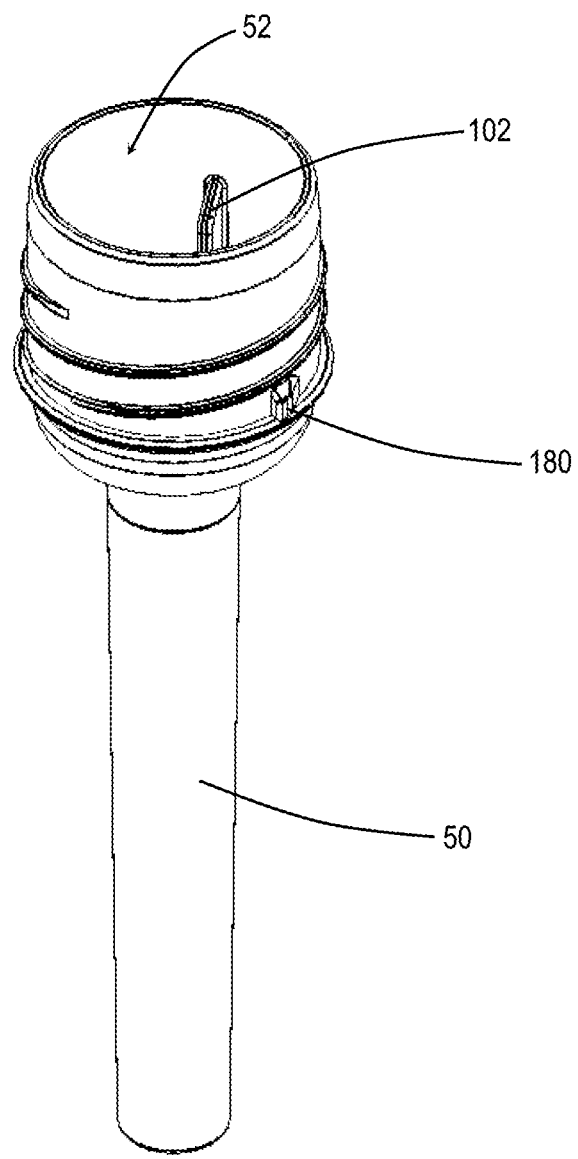
FIG. 33 is a schematic perspective view showing a collection tube (optionally usable with the cap of FIG. 32), according to some embodiments.

Referring to FIGS. 30 and 31, in some embodiments, and applicable to any of the above examples, the sample collection device may further include locking and/or sealing means, such that the cap cannot be removed from the tube by the donor once the cap has been connected or screwed onto the tube, such as by the donor. Suitable locking members can include a wedge on the cap and a matching flange on the tube or visa-versa. The wedge and flange can either be on the inside of the cap and tube, or on the outside of the cap and tube. Suitable sealing means include a sealed cavity containing a sealing solution, such as a glue, wherein the sealing solution is released when the cap is pushed, rotated or screwed onto the tube and thereafter cures in order to prevent disengagement between the cap and tube. In some embodiments, the sealing solution may be a two-component glue, such as an epoxy, with one component being sealed into the cap, and the other component sealed into the tube, such that the two components mix within the threads when the cap is screwed onto the tube. In other embodiments, the sealing solution can be a single component, such as a cyanoacrylate-based glue, which can be in a sealed cavity in the cap or tube, such that the sealing solution is released into the threads when the cap is screwed onto the tube. In some embodiments, the sealing solution can cure soon after engagement between the cap and tube such that disengagement between the tube and cap by the user can be generally prevented.

Referring to FIGS. 30 and 31, in one form, a locking means may comprise a ratchet or a resilient latch. The ratchet or latch may, for example, comprise at least one projection or formation 150 that has a ramp surface 152 for permitting a second component 154 to pass over the formation 150 by riding over the ramp surface 152 in the first direction (corresponding to the rotation direction to screw the cap 12 to the tube 14), and an abutment surface 156 for blocking (or at least obstructing) movement in the second direction (unscrewing direction). The second component 154 may optionally comprise complementary ramp and abutment surfaces. Additionally or alternatively, to any of the above, the ratchet or latch may, for example, comprise a cantilever and/or articulated member 158 configured such that, in use, the member 156 is (i) able to be displaced by a second component 154 for permitting the second component 154 to pass the cantilever/articulated member 156 in the first direction, and (ii) not displaced by the second component 154 when contacted in the second movement direction.

One component may be arranged on the cap 12 and the other on the tube 14. For example, as illustrated in FIGS. 30 and 31, a second component ramp or wedge 154 may be formed on the tube, for engagement by a latch/ratchet of the cap 12 and defining the cantilever member 158 and/or the formation 150.

In some embodiments, the first and second movement directions may, for example, be generally axial or they may, for example, be generally circumferential.

The lock device may generate a signal (second signal) to the user to indicate that the lock device has locked the cap 12 in its closed state. The second signal may include audible and/or tactile signal components generated by the operation of the, for example, ratchet or latch. For example, the user may feel a physical "click" upon the lock operating, and/or hear a "click" sound.

In some embodiments, the collection device may be configured to provide to the user a first signal indicative of the chamber having been opened, and a second signal indicative of the cap having reached a closed and/or locked position.

As already described, the first signal may result from dropping down of the second cap portion 22 at least partly into the tube. The first signal may be at least partly visual, and/or at least partly tactile, and/or at least partly audible.

As described recently above, the second signal may result from operation of a lock device (for example, a latch or ratchet). The second signal may be at least partly tactile and/or at least partly audible.

The combination of the first and second signals generated to the user can provide intuitive feedback to the user that the cap is firmly closed, and that the agent has been released.

Referring to FIGS. 32 to 37, a further embodiment of sample collection device is illustrated. (In some of these drawings, a quadrilateral "X" denotes a cut-plane where an item is shown partly or wholly in cross-section.) The device may have any of the features described hereinbefore, whether or not illustrated or described below. In particular, the device 10 may comprise a cap 12 threadedly engageable at and/or over the mouth of a collection tube 14. The cap 12 may comprise a first cap portion 20 having an inner wall 36 defining a chamber 16 for a reagent, the chamber 16 having an open lower end. The cap may further comprise a second cap portion 22 in the form of a closure (or cap or plug) for closing the open end. The second cap portion 22 may be threadedly coupled to the first cap portion 20 by a reverse thread (e.g. having an opposite thread direction to the threaded coupling between the cap 12 and the tube 14).

In the illustrated form, at least a region of the second cap portion 22 may have a top hat shape. For example, referring to FIG. 36, the second cap portion 20 may comprise an inverted cup portion 160 defining a hollow cavity 162, and encircled by a flange (or annular shoulder) 164. The (e.g. reverse) screw thread of the second cap portion 22 may be radially outwardly facing (e.g. example, carried on a radially outwardly facing surface of the inverted cup portion 160) for engaging a radially inwardly facing screw thread of the first cap portion 20 (e.g. carried on a radially inwardly facing surface of the inner wall 36). Such a shape of second cap portion 22, with a cavity 162, may be especially suitable to be made by injection molding, without requiring complicated mold parts, or excess plastics.

The second cap portion 22 may further comprise abutments 100 in the form of lateral extensions of the flange 164. In some embodiments, two abutments 100 may be provided, generally diametrically opposed, in a similar manner to the embodiment of FIGS. 16-19. However, in other embodiments, the number of abutments 100 may be fewer than two, or greater than two, according to design choice.

In some embodiments, the contact between the first and second cap portions 20 and 22 may be sufficient to form a liquid-tight seal to prevent leakage of the agent prior to intended use. Additionally or alternatively, a seal gasket 166 may be provided to effect a seal at an interface between the first and second cap portions 20 and 22. For example, the seal gasket 166 may have a closed-loop or washer shape (or optionally an O-ring). When provided, the seal gasket 166 may be carried by one of the first and second cap portions 20 and 22, for example, attached to the second cap portion 22 as indicated by the arrow in FIG. 36. The gasket 166 may, for example, be adhered to the flange 164. Alternatively, the gasket 166 could be integrally formed by a multi-shot molding process. In the modified example of second cap portion 22 in FIG. 37, the gasket 166 may be retained in place by a peripheral wall 168 of the second cap portion 22 and/or by one or more undercut retainers 170 of the second cap portion 22. In the illustrated example, both the peripheral wall 168 and the retainers 170 are illustrated, but one or the other could be used independently, and/or in addition to the adhering or multi-shot molding of the gasket 166 with respect to the second cap portion 22. In the case of undercut retainers 170, the flange 164 may be formed with openings 172 resulting from, or accommodating, portions of the mold tooling for forming the undercut retainers 170. As explained above, the gasket 166 may be omitted altogether if the contact between the cap portions 20 and 22 themselves is sufficient to effect a liquid-tight seal for containing the agent with the compartment 16.

Figure 34:
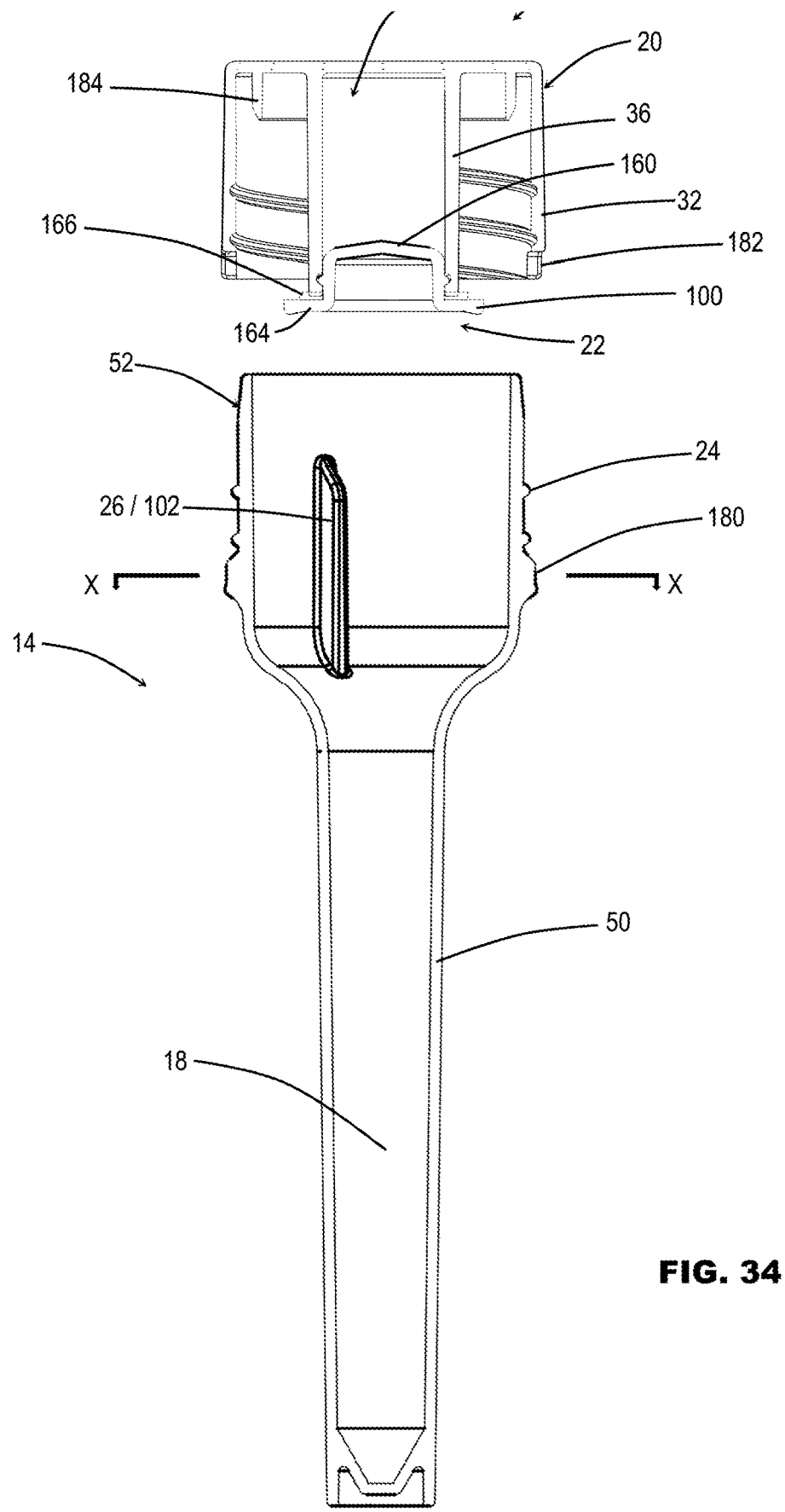
FIG. 34 is a schematic section showing the cap of FIG. 32 and the tube of FIG. 33 just prior to fitting together, according to some embodiments.
Figure 35:
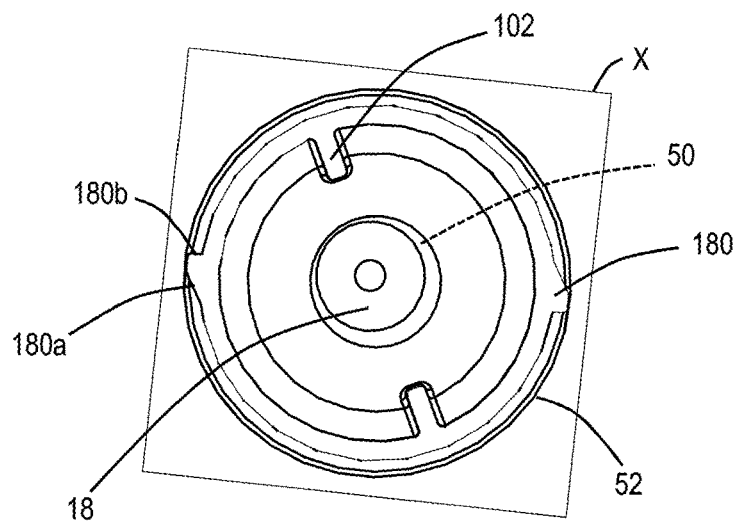
FIG. 35 is a schematic section along the line X-X of FIG. 34, according to some embodiments.
Figure 36:
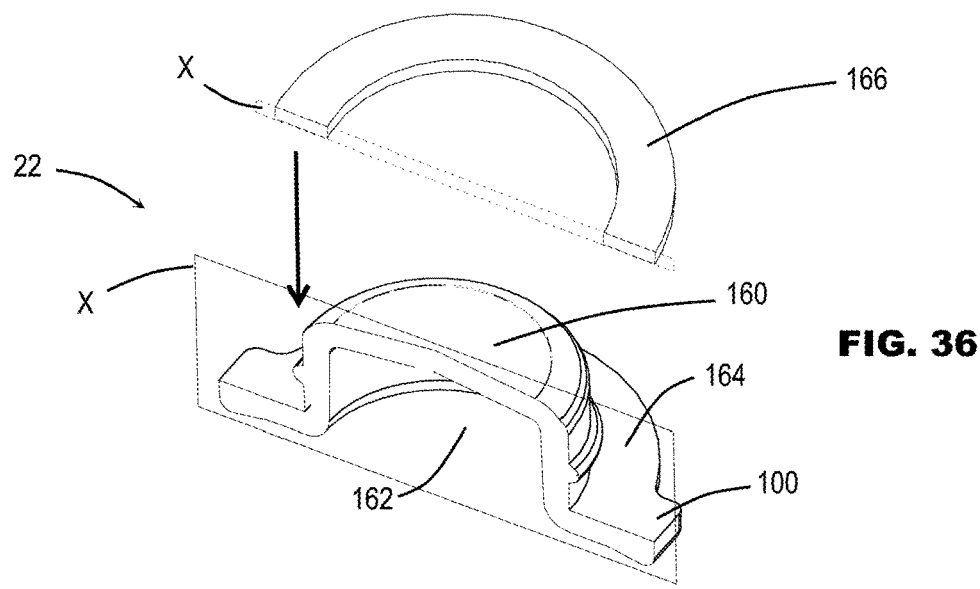
FIG. 36 is a schematic perspective section through an example of second cap portion (plug) for the cap of FIGS. 32 and 34, according to some embodiments.
Figure 37:
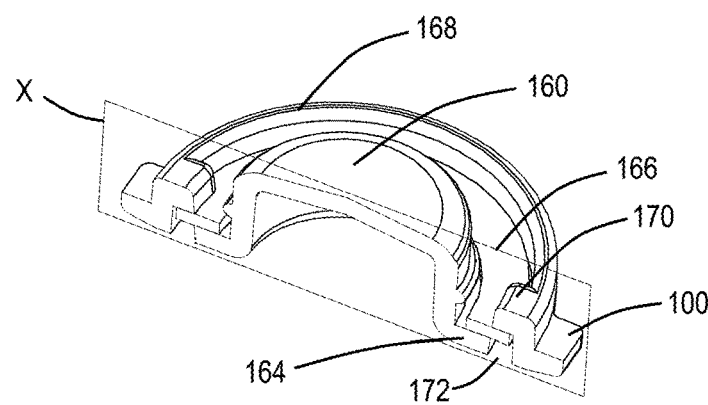
FIG. 37 is a schematic perspective section through an alternative example of second cap portion (plug) for the cap of FIGS. 32 and 34, according to some embodiments.

As may be seen in FIG. 34, in some embodiments, the inner wall 36 and/or the second cap portion 22 may depend or project below the periphery of the outer side wall 32. This can facilitate keying of the abutments 100 and the projections 102 when fitting the cap 12 to the tube 14. Additionally or alternatively, it can enable the projections 102 to be placed lower inside the mouth 52 of the tube 14, such that the projections 102 are recessed or spaced axially away from the open end of the tube 14. Even though the projections 102 are not sharp, spacing the projections 102 away from the open end (to be contacted in use, for example, by the donor's mouth or lips), may enhance further the ergonomics of the device 10 and avoid any surprising sensation of the projections 102 against the donor's mouth or lips should the donor's lips accidentally enter the open end while using the device 10.

In a similar manlier to that described previously, when the cap 12 is fitted to, and tightened by screwing on, the mouth 50, rotation of the second cap portion 22 relative to the tube 14 is obstructed once the abutments 100 of the second cap portion 22 abut the projections 102 of the tube mouth 50. Continued screwing of the cap 12 (e.g. the first cap portion 20) generates relative rotation between the first and second cap portions 20 and 22. The reverse threaded coupling between the first and second cap portions 20 and 22 causes the second cap portion 22 to unscrew from the first cap portion. Once released, the second cap portion 22 may drop down from the inner wall 36, thereby opening the compartment 16, and allowing the reagent in the compartment 16 to be dispensed into the sample collection space 18 of the tube. The dropping down of the second cap portion 22 may generate a first signal to the user, that the reagent has been released as intended. The first signal may, for example, be at least partly tactile (e.g. the user feeling the dropping down), and/or at least partly visual (e.g. the user seeing the second cap portion 22 in its dropped down position if the tube 14 comprises transparent material), and/or at least partly audible (e.g. if the user hears the second cap portion 22 dropping down).

As described for preceding embodiments, the design may be varied according to design preference regarding the angle of rotation (e.g. turns) for screwing the cap 12 on to the tube 14, and/or for unscrewing the second cap portion 22. For example, the rotation to secure the cap 12 may be made up of (a) a first angle to bring the thread starts of the first cap portion 20 and the tube 14 into alignment, and (b) a second angle to fully screw the cap 12 on to the tube. In some embodiments, the first cap portion 20 and the tube 14 may include two thread starts, e.g. diametrically opposed, such that the angle (a) is up to about half a turn (depending on an arbitrary orientation of initial fitting, the worst case is up to a half turn before the thread starts are aligned). The angle (b) to fully engage the first cap portion 20 may be about a full turn, optionally at least about a full turn, optionally at least about one and a quarter turns, optionally at least about one and a half turns. If desired, the first angle (a) may be reduced by increasing the number of thread starts. For example, for three thread starts the angle (a) may be up to about a third of a turn, or for four thread starts the angle (a) may be up to about a quarter of a turn.

Within the combined range of movement (a) plus (b) above, the movement to disengage the second cap portion 22 may also be accommodated. For example, the motion to disengage the second cap portion 22 may be made up of (c) a third angle to engage the abutments 100 with the projections 102, and (d) a fourth angle for the second cap portion 22 to unscrew once its rotation is restrained with respect to the tube 14. The third angle (c) may depend on the number of projections 102 and/or the number of abutments 100. In the illustrated form, the number of projections 102 is two, and the number of abutments 100 is also two. The third angle (c) may be up to about half a turn. Depending on an arbitrary orientation of initial fitting, the worst case is up to about half a turn before the abutments 100 are aligned to engage the projections 102. The fourth angle (c) depends on the thread design. In some embodiments the fourth angle may generally be less than three-quarters of a turn, optionally not more than about half a turn, optionally not more than about a quarter of a turn. If desired, the third angle (c) may be reduced by increasing the number of abutments 100 and/or the number of projections 102. For example, by increasing the number of abutments 102 to four, and/or by increasing the number of projections 100 to four, each uniformly arranged, the third angle (c) may be reduced to up to about a quarter of a turn.

In some embodiments, the cap 12 and tube 14 may be configured such that the abutments 100 of the second cap portion 22 do not engage the projections 100 of the tube 14 before the first cap portion 20 has already been threadedly engaged (e.g. the thread starts have already engaged) with the tube 14. Such an arrangement may prevent the second cap portion 22 from beginning to unscrew before the cap 12 is at least partly screwed on to the tube 14. For example, the abutments 100 may engage the projections 102 only after the first cap portion 20 has already begun threaded engagement with the tube 14 through at least about a quarter of a turn.

Additionally or alternatively, in some embodiments, the second cap portion 22 may be configured to disengage from the first cap portion 20 before the first cap portion 20 has completed fully being screwed on to the tube 14. This may ensure that the second cap portion 22 is always reliably disengaged during fitting of the cap 12. For example, the second cap portion 22 may disengage at about at least a quarter of a turn before the fully screwed position of the cap 12 on the tube 14 (optionally at least half a turn before, optionally at least three-quarters of a turn before). Such an arrangement can also provide the sequential generation of first and second indicator signals to the user as described above.

Owing to manufacturing (e.g. molding) tolerances, the above specifications of angles may (in some embodiments) vary by as much as plus or minus a quarter of a turn.

The tube 14 may have a shape in which the interior cross-sectional area may be smaller in the sample collection space 18, than at the mouth 52. The narrowing of the interior cross-section may act as a natural support or stop to obstruct the second cap portion 22 from dropping (e.g. fully) into the sample collection space 18. The small interior cross-section may also enhance the visibility of the amount of bodily fluid collected, compared to a target fill line or scale (not shown). The small interior cross-section may, in some embodiments, be dimensioned at least to prevent entry of the second cap portion 22.

The device 10 may be configured with a lock to obstruct removal of the cap 12 from the tube 14 by the donor once the cap 12 has been connected or screwed on to the tube 14. For example, the lock may comprise at least one lock wedge 180 on one of the tube 14 and cap 12, and at least one lock keep 182 on the other of the tube 14 and cap 12. In the illustrated form, the tube 14 comprises the lock wedge(s) 180 (for example, one, two, three, four, or more), and the cap 12 comprises the lock keep(s) 182 (for example, one, two, three, four, or more). The number of wedges 180 and keeps 182 may be the same of different, according to design preference. In the illustrated example, two lock wedges 180 and two lock keeps 182 are provided.

Each lock wedge 180 may generally comprise a ramp surface 180a, and an abutment surface 180b. Additionally or alternatively, each keep 182 may generally comprise an opening or recess, and an abutment edge or surface around the opening or recess. The keep 182 may, for example, comprise a generally rectangular or inverted-U-shaped cut-out in the cap wall. The wedge 180 and keep 182 are generally configured such that, when the cap 12 is screwed to a fully closed position on the tube 14, the abutment surface of the keep 182 can cam or slide progressively over the ramp surface 180a of the wedge. Upon reaching the fully closed position, the wedge 180 is received at the opening or recess of the keep 182. Should the user try to unscrew the cap, the abutment surface 180b of the wedge will abut or strike the abutment edge of the keep 182, thereby blocking or obstructing such unscrewing motion, and effectively locking the cap 12 in its fully closed position.

The engagement of the lock may generate a second signal to the user, indicative of the cap 12 reaching its fully closed position. The second signal may, for example, be at least partly tactile (e.g. the user feeling a click as the wedge 180 enters the keep 182), and/or at least partly visual (e.g. the user seeing the wedge 180 captive in the keep 182), and/or at least partly audible (e.g. if the user hears an audible click as the wedge 180 enters the keep 182).

In the illustrated example (as may be seen in FIGS. 32 and 34), the abutments 100 of the second cap portion 12 may be (in the closed position of the second cap portion 22 with respect to the first cap portion 20) generally angularly aligned with (e.g. on the same radius direction as) the lock keeps 182. Especially in the case of the lock keeps 182 being visible on or from the exterior of the cap 12, this can enable the lock keeps 182 to be used as a visual alignment aid, should it be desired to align or key the abutments 100 with the projections 102 in the mouth 52 of the tube 14 when initially fitting the cap 12 on to the tube 14.

In some embodiments, in the closed position, the cap 12 may effect a liquid-tight seal at the mouth of the tube 14. Various different seal configurations may be used as desired. In the illustrated example, a very effective seal may be provided by a depending annular seal lip (or wedge or wiper) 184 (FIG. 34) that can engage the inner surface of the mouth of the tube 14.

Alternatively, or in addition, and applicable to any of the examples described previously, some embodiments may flintier include an annular member at the base of the cap that is partially secured to the cap, such that removal of the cap after it has been screwed onto the tube breaks the bond between the cap and the annular member, thereby indicating that the tube has been opened. This "tamper-evident" embodiment is similar to those used to attach a cap to a soda bottle.

As described above, in some embodiments, the second cap portion 22 may be configured to drop down at least partly into the tube 14. When the device 10 subsequently is returned to a laboratory for processing of the preserved sample, it may be desirable to remove the second cap portion 22 in a manner that does not interfere with the collected sample. As already described, the second cap portion 22 may in some embodiments remain captively coupled to the first cap portion 20 such that, when the first cap portion 20 is removed to open the device 10, the second cap portion 22 may be withdrawn automatically with the first cap portion 20. However, in other embodiments in which the second cap portion 22 is not captively coupled, the second cap portion 22 may remain in the tube 14 after removal of the first cap portion. The following examples address how the second cap portion 22 may be retrieved independently, without interfering with the collected sample.

Figure 39:
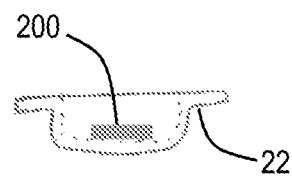
FIG. 39 is a schematic section view showing a first example of second cap portion having a retrieval magnet, according to some embodiments.
Figure 40:
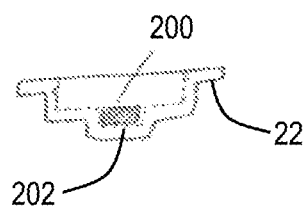
FIG. 40 is a schematic section view showing a second example of second cap portion having a retrieval magnet, according to some embodiments.
Figure 41:
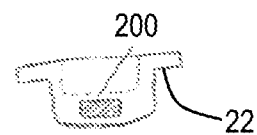
FIG. 41 is a schematic section view showing a third example of second cap portion having a retrieval magnet, according to some embodiments.

Referring to FIGS. 39-41, in some embodiments, the second cap portion 22 may carry or comprise a magnetic element 200. The magnetic element 200 may, for example, be a magnet, or it may be of material that is attractable by a magnet. Different mountings of the magnetic element 200 are envisaged. For example, referring to FIG. 39, the magnetic element 200 may be surface mounted on the second cap portion 22, for example, in the cavity of a plug shaped second cap portion 22. Alternatively, referring to FIG. 40, the magnetic element 200 may be received in a suitable recess 202. The profile of the cap 22 may optionally bulge to one side (shown at 204) to accommodate the recess 202 without requiring thinning of the cap material. In a further alternative example of FIG. 41, the magnetic element 200 may be embedded substantially entirely in the material of the second cap portion, such that the magnetic element 200 has substantially no exposed surface.

Figure 42:
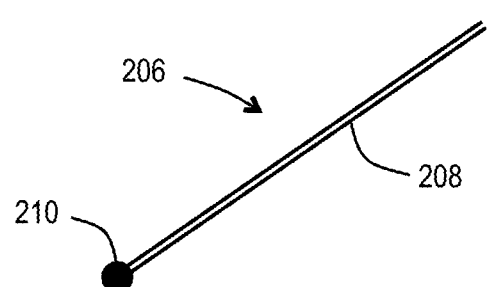
FIG. 42 is a schematic side view of a retrieval tool for use with the examples of FIG. 39, 40 or 41, according to some embodiments.

FIG. 42 illustrates a retrieval tool 206 for use to retrieve the second cap portion 22 of FIGS. 39-41. The retrieval tool 206 may comprise a handle 208 having a magnetic element 210 at one end configured to magnetically attract the element 200 of the second cap portion 22. By inserting the end of the tool 206 having the magnetic element 210 into the tube 14, the second cap portion 22 can easily be magnetically hooked and retrieved, without interfering with the preserved sample.

As an alternative to magnetic retrieval, a mechanical gripping/hooking and retrieval are also envisaged. Various mechanical arrangements may be used, for example, an "eye" and "hook" system (not shown) in which the second cap portion is provided with an open eye capable of being hooked by a suitable hook provided on a retrieval tool.

FIGS. 43 and 44 illustrate an alternative mechanical retrieval tool 220, including a deployable gripper 224 disposed within a control sleeve 222. The gripper 224 may have distensible and/or deployable gripper fingers 226. The fingers 226 may be resiliently biased to a distended state (FIG. 44), but be radially collapsible to a stowed state when constrained by the control sleeve 222 (FIG. 43). The gripper 224 and/or the fingers 226 may be of any suitable elastic or super-elastic material. In one example use, the tool 220 is advanced in its collapsible condition (FIG. 43), towards a feature of the second cap portion 22. To deploy the gripper 224, the control sleeve 222 may be retracted (as shown by the arrows in the upper half of FIG. 44) and/or the gripper 224 may be advanced relative to the sleeve 222. Once no longer constrained by the sleeve 222, the fingers 226 are free to distend to engage the feature of the second cap portion (as described below).

FIGS. 45 to 48 illustrates examples of second cap portion 22 that include a feature mechanically grippable by the retrieval tool 200. The feature may be a recess or hole 228 (for example a blind hole) capable of being gripped by the fingers 226 when the deployment end of the tool 220 is inserted into or positioned adjacent to the hole 228, depending on the dimensions of the fingers 226. The fingers 226 may distend into contact with the sidewall of the hole 228, providing sufficient contact force to enable the second cap portion 22 to be retrieved. In FIG. 45, the hole 228 may be the or a cavity 230 on the underside of the plug shape of the second cap portion 22. In FIG. 46, the hole 228 may be a smaller recess in the floor of the cavity. In FIGS. 47 and 48, plural holes 228 may be provided on opposite faces or sides of the second cap portion 22 to permit retrieval whether the second cap portion 22 is lying upside down or normally.

Figure 49:
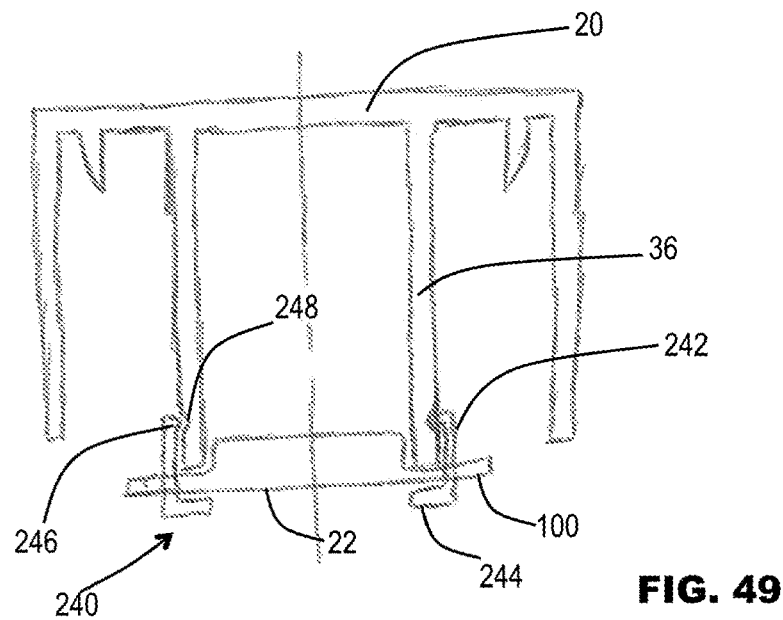
FIG. 49 is a schematic section view showing a cage fitted to the first cap portion for keeping the second cap portion captive, according to some embodiments.
Figure 50:
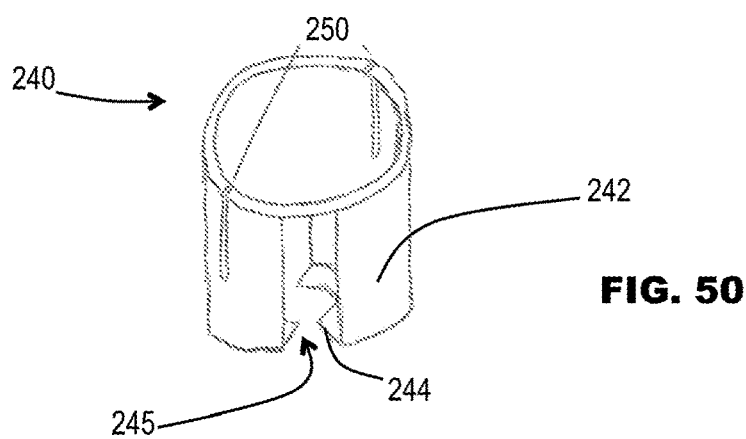
FIG. 50 is a schematic section view showing the cage of FIG. 49 in isolation, according to some embodiments.

Referring to FIGS. 49 and 50, as previously described, instead of the second cap portion 22 being free to separate completely from the first cap portion 20, the first cap portion 20 may be provided be a cage 240 into which the first cap portion 22 may fall, while being retained captive and removable from the tube 14 with the first cap portion 20 when the first cap portion 20 is removed to open the tube 14.

In the illustrated form, the cage 240 may comprise a plurality of depending struts or members 242 configured in use to depend from the inner wall 36 of the first cap portion, and a plurality of transverse struts or members 244 that collectively define a floor, or bottom supports, of the cage 240 on which the second cap portion 22 may rest once the second cap portion 22 has opened. In the illustrated form, the depending members 242 and the transverse members 244 are integrally firmed as L-shaped members. The L-shaped members may be interconnected at the upper end of the cage 240, to define a tubular shape of the cage 240.

The cage 240 may include apertures 245 through which the abutments 100 of the second cap portion 22 may project to engage the projections 102 defining the second engager 26 previously described. The apertures 245 may, for example, be defined by spaces between the depending members 242.

The cage 240 may optionally define the extent to which the second cap portion 22 may separate from the inner wall 36 of the first cap portion 20 when the second cap portion 22 is released. FIG. 49 may illustrate a relatively shallow cage 24 limiting the separation; F 50 may illustrate a deeper cage 240 permitting greater separation. It will be appreciated that the dimension may be varied according to design preference.

In some embodiments, the cage 240 may be produced separately from the first cap portion 20, and be securable to the first cap portion 10 either at the same time as fitting the second cap portion 22 to seal the chamber, or thereafter. For example, the cage 240 may clip to the first cap portion 10, or another securing mechanism may be provided. In the illustrated form, the mouth of the cage 240 is formed with a radially inwardly projecting undercut 246 which forms an interference fit with a circumferential groove 248 of the inner wall 36. The undercut 246 and the groove 248 optionally may have surfaces designed to permit easy assembly, but to obstruct disassembly.

In order to permit expansion of the mouth of the cage 240 to permit the undercut 246 to ride over the inner wall 36 to the groove 248, at least one (optionally multiple or all) of depending members 242 may be formed with axial slits or cuts 250.

In some embodiments, the cage 240 may be rotatable (e.g. with the second cap portion 22) about the axis of the chamber. For example, the cage 240 may be produced (e.g. molded) in its as-fitted state. The slits 250 may permit temporary expansion of the mouth of the cage 240 to assemble the cage 240 to the inner wall 36, after which the cage 240 returns to its undeformed state.

Alternatively, in some embodiments, the cage 240 may be substantially non-rotatable (or rotation may be at least partly resisted), by circumferential friction between the cage 240 and the inner wall 36. For example, the cage 240 may be produced (e.g. molded) in a slightly undersized state. The slits 250 may permit forced expansion of the mouth of the cage 240 when assembling the cage 240 to the inner wall 36. Once fitted, the cage 240 may remain expanded, tending to squeeze against the groove 248 of the inner wall 36 to produce circumferential friction that at least partly resists, relative rotation with respect to the first cap portion 20.

Figure 51:
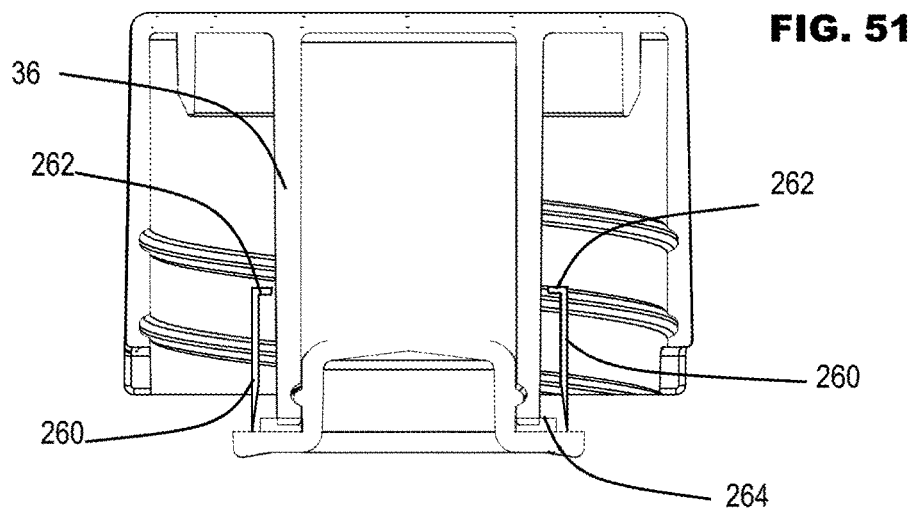
FIG. 51 is a schematic section view showing a further example of retainer for retaining the second cap portion captive to the first cap portion, according to some embodiments.

Referring to FIG. 51, in some embodiments, the second cap portion 22 may be provided with retainer arms 260 extending upwardly to overlap the inner wall 36 around the chamber. The retainer arms 260 may have barbs or abutments 262 which engage behind a beaded lower edge 264 of the inner wall 36 when the second cap portion 22 drops downwards. The second cap portion 22 may be rotatable with respect to the first cap portion, but coupled or retained captively to the first cap portion 20 by the retainer arms 260.

Figure 52:
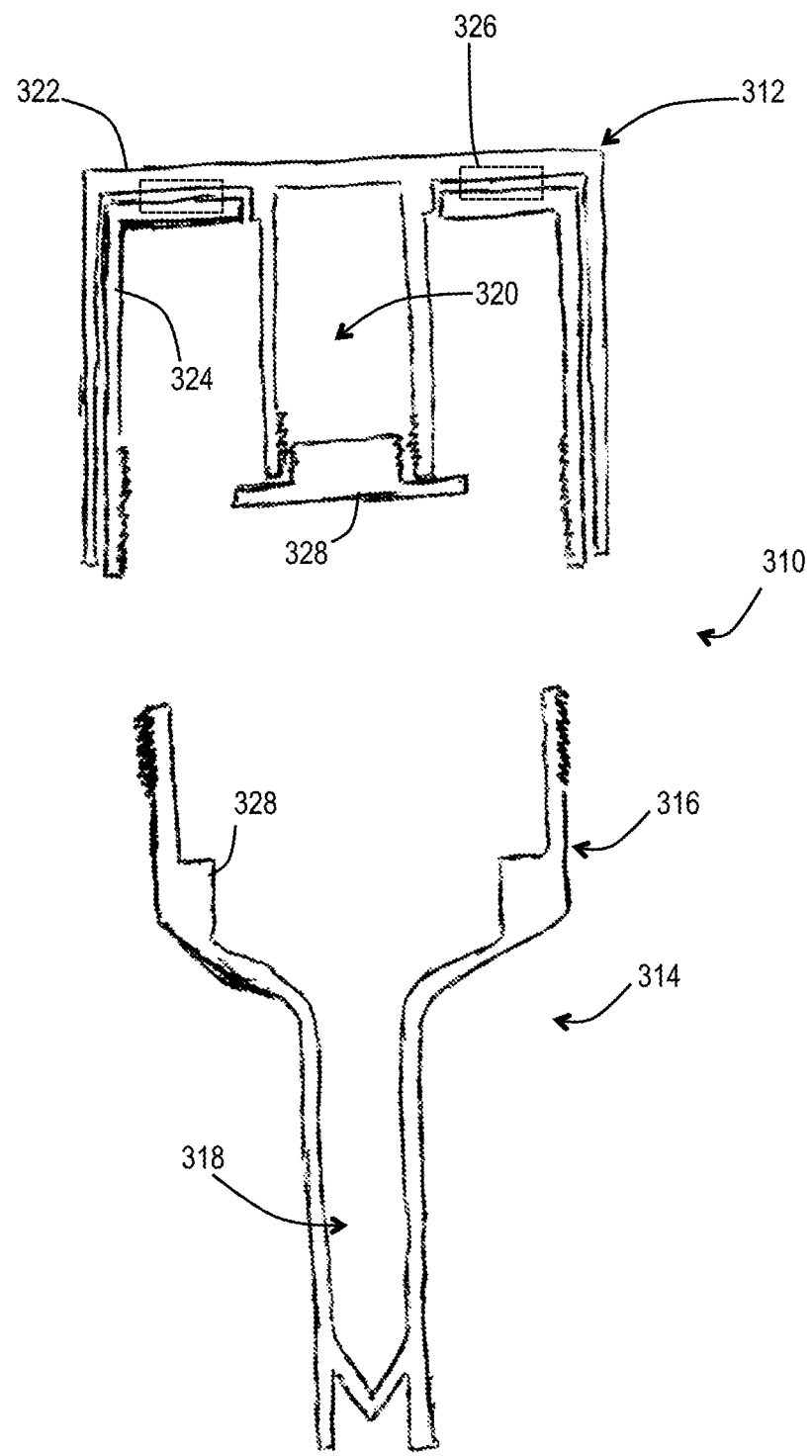
FIG. 52 is a schematic section of a bodily fluid sample collection device, including a cap and a tube, according to some embodiments.

Referring to FIG. 52 in some embodiments, a bodily fluid sample collection device 310 for the collection of naturally expressed body fluids, generally comprises a cap 312 engageable with a tube 314 to close a mouth 316 of the tube. The tube 314 defines at least partly a sample collection space 318 for receiving the natural expressed bodily fluid. The device 310 (the cap 312 in this embodiment, or optionally the tube in other embodiments) comprises a chamber 320 for containing a reagent for mixing with a collected sample. The cap comprises a first body 322 by which a user manipulates the cap, and a second body 324 that is rotatably mateable with the tube for securing the cap 312 to the tube 314. A coupling (shown schematically at 326) between the first and second bodies may be configured for (i) transmitting torque from the first body to the second body for permitting rotation of the second body to secure the second body to the tube, and (ii) permitting slippage between the bodies after the second body has reached a fully secured position. A mechanism (328a, 328a) is operable to cause the chamber to be opened in response to manual rotation of the first body at least after the second body has reached the fully secured position.

The mechanism 328a, 328a may be operable to begin to cause the chamber 320 to be opened only after the second body 324 has reached the fully secured position, or the mechanism 328a, 328a may be operable partly before the second body 324 has reached the fully secured position. In either case, the second body 324 may reach the fully secured position before the chamber 320 has been fully opened. Further manual rotation of the first body 322 after the second body 324 has reached the fully secured position, may open or complete the opening of the chamber 320.

The second body 324 may be threadedly mateable with the tube 314, but other rotatably mateable couplings, such a bayonet coupling, may be used as desired.

In some embodiments, the coupling 326 may be a torque-responsive coupling. In some embodiments, the coupling 326 may be a torque-limiting coupling that limits the amount of torque transmissible from the first body 322 to the second body 324, and permits relative slippage between the two bodies 322, 324 when the torque exceeds a threshold. For example, during initial fitting (e.g. screwing) of the cap 312, the second body 324 may rotate relatively freely as it mates with the tube 314, and the applied torque may be small. Once the second body 324 reaches a fully secured position on the tube 314, it can no longer rotate relative to the tube 314, and the applied torque will therefore increase. The coupling 326 may be responsive to applied torque to permit the first body 322 to slip with respect to the second body 324, thereby permitting continued rotation of the first body 322 despite the second body 324 no longer being able to rotate.

In some embodiments, the coupling may be responsive to the direction of rotation, so as not to transmit significant torque from the first body 322 to the second body 324 in a rotation direction for releasing the second body 324.

In some embodiments, the coupling 326 may comprise a ratchet and/or a clutch.

In some embodiments, the second body 324 may be substantially shrouded by the first body 322, at least during fitting of the cap 312 on the tube 314.

In some embodiments, the mechanism 328a, 328a for causing opening of the chamber may be responsive to relative rotation between the tube 314 and the first cap portion 322. Alternatively, the mechanism for causing opening of the chamber may be responsive to rotation between the first and second bodies.

Various mechanisms are envisaged. In one form, the chamber 320 may comprise an aperture closed by a closure 328a. The closure may be a third body distinct from the first body 322, or it may be integral with the first body 322. The closure 328a may be rotatable relative to the chamber 320 to open the chamber 320. For example, the closure 328a may be threadedly coupled to the chamber 320. In some embodiments, the chamber 320 may be rotatable with the first member 322. The mechanism 328a, 328a may operate to restrain the closure 328a against rotation with respect to the tube 314 and/or the second body. For example, the mechanism may comprise abutments 328a in the mouth 316 that engage projections of the closure 328a to block rotation of the closure 328a. Rotation of the first body 322 may rotate the chamber 320, thereby generating relative rotation between the chamber 320 and the closure 328a, to move the closure 328a to an open condition with respect to the chamber aperture.

Other types of mechanisms for opening the chamber may also be used, for example, a piercing element that ruptures a frangible film or wall of the chamber.

Figure 53:
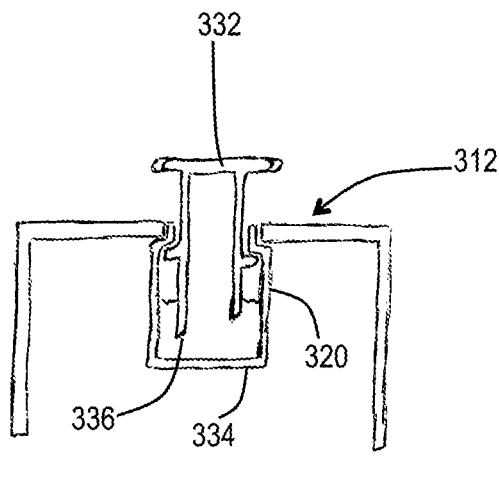
FIG. 53 is a schematic section showing a further embodiment of cap with a chamber actuator in a non-actuated position, according to some embodiments.
Figure 54:
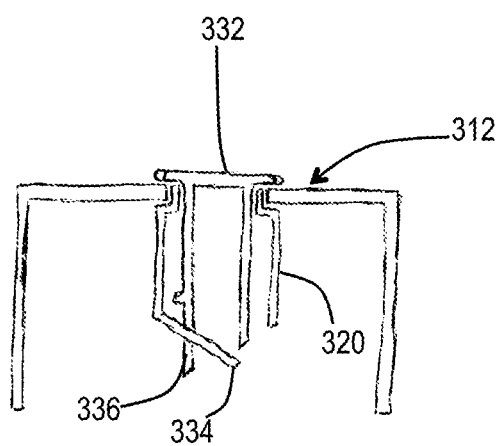
FIG. 54 is a schematic section similar to FIG. 53, but showing the chamber actuator in an actuated position to open the chamber, according to some embodiments.

Referring to FIGS. 53 and 54, a further example of cap 212 is illustrated. The cap may be used with the tube of FIG. 52, or with the tube of FIG. 57 described later, or with a tube as illustrated in other drawings herein, or as described in the aforementioned WO 2012/177656.

In FIGS. 53 and 54, the sample collection device (optionally the cap 312 as shown in this embodiment, or optionally the tube in other embodiments) comprises a chamber 320 for containing a reagent for mixing with a collected sample. The device (optionally the cap 312 in this embodiment, or optionally the tube in other embodiments) may further comprise a manually operable actuator 332 operable from outside the device at least once the cap has been secured to the tube, for causing the chamber 320 to be opened in response to manual actuation of the actuator 332.

In some embodiments, the device may optionally comprise a lockout mechanism (not shown) for preventing actuation of the actuator 332 before the cap 312 has been placed in a fully secured position.

In some embodiments, the actuator may be rotatable and/or pressable and/or depressible.

In the illustrated form, the chamber 320 comprises a body with a frangible wall 334. The actuator 332 comprises a plunger with a tip 336 shaped for cutting or breaking the wall 334 when the plunger is depressed (FIG. 54). Opening of the wall 334 permits the reagent in the chamber 320 to mix with the collected bodily fluid sample.

Figure 55:
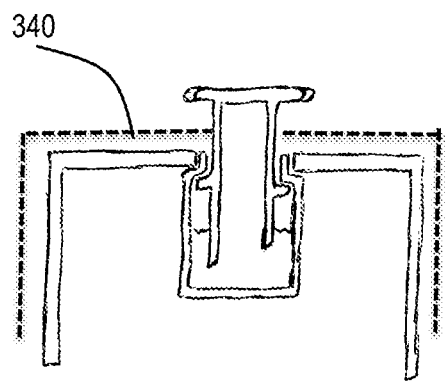
FIG. 55 is a schematic section similar to FIG. 53 showing how the cap is too large to be received in packaging, according to some embodiments.
Figure 56:
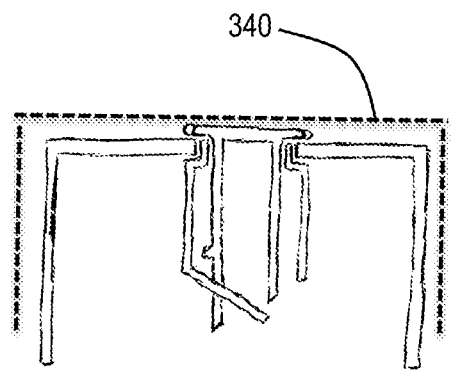
FIG. 56 is a schematic section similar to FIG. 54, showing how the cap is able to fit within the confines of the packaging, according to some embodiments.

Referring to FIGS. 55 and 56, in some embodiments, the device may be provided as part of a kit containing packaging (depicted schematically at 340) in which the device is intended to be placed for sending (e.g. by post) to a processing institution for processing, analysis or research. The packaging 340 may be configured to accept the device only in a condition in which the actuator has been actuated to cause the chamber to be opened. For example, the packaging 340 may include a predetermined space (e.g. a well) that is dimensioned to receive the device only in such a condition. The actuator may, for example, be depressable, whereby an exterior dimension of the cap or tube becomes smaller. Prior to depression (FIG. 55), the device may be too large to fit in the predetermined space of the packaging 340. The projecting actuator 332 may make the device too tall to fit within the confines of the packaging 340. Referring to FIG. 56, the device may only fit once the actuator 332 has been fully depressed. Such an arrangement can ensure that the user does not accidentally forget to operate the actuator.

Figure 57:
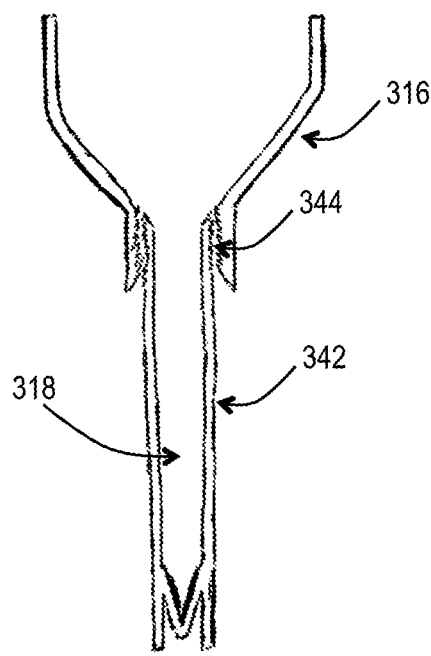
FIG. 57 is a schematic section showing a further embodiment of tube.

Referring to FIG. 57, a further example of tube 314 is illustrated. Although not shown explicitly in FIG. 57, the tube 314 may be used with the cap of any of the preceding embodiments, or as described in the aforementioned WO 2012/177656. The cap may be secured to a mouth portion 316 of the tube 314 to seal the collected bodily fluid sample closed. In some embodiments, the tube 314 defines at least partly a sample collection space 318 for receiving the naturally expressed bodily fluid. The device (optionally the cap, or optionally the tube) comprises a chamber (not shown) for containing a reagent for mixing with a collected sample.

In some embodiments, the mouth portion 316 may be separable from a collection portion 342 of the tube 314, to facilitate opening of the device after the cap has been secured. The collection portion 342 of the tube may define the collection space 318. For example, the mouth portion 316 may be coupled to the collection portion 342 by a threaded connection 344, or some other mechanically separable connection, or by a frangible integral connection.

The mouth portion 316 may flare towards an open end defining a mouth of the tube, and/or narrow towards the collection portion. The mouth portion 316 may optionally comprise the abutments 328a (or other mechanism) for interacting with the chamber to cause the chamber to be opened, although such abutments are not shown in FIG. 57 for clarity.

In some embodiments, the cap and the mouth portion together comprise a mechanical or adhesive lock for locking the cap in its fully secured condition once the cap has been closed. With an arrangement as in FIG. 57, the ability to separate the mouth portion 316 from the collection portion 342 of the tube 314 may facilitate ease of access to the sample contents when the device is received at a processing installation, while still obstructing accidental reopening of the cap by the user having deposited a sample.

Additionally or alternatively, in some embodiments, the cap may comprise a closure for a chamber for containing reagent. The closure may be configured to be opened when, or after, the cap may be secured to the mouth portion, the closure dropping down into the mouth portion 316 when the closure is opened. The mouth portion 316 may prevent the closure from dropping into the collection portion 342 of the tube. With such an arrangement, the ability to separate the mouth portion 316 from the collection portion 342 of the tube may facilitate easy access to the sample contents, without having to manually retrieve the closure from the mouth portion. Instead, by removing the mouth portion itself, the closure is removed with the mouth portion.

Additionally or alternatively, in some embodiments, the ability to separate the mouth portion 316 from the collection portion 342 may enable the sample to be handled, processed or stored in a relatively more compact form of the collection portion 342 absent a flared or funnel shaped mouth portion 316.

The sample collection devices according some embodiments can be made of any suitable plastics, such as polypropylene, polystyrene and polycarbonate. The dimensions of the device can be modified to suit the specific processing the sample will be subjected to. In certain embodiments, typical dimensions include the following. For the inner chamber of the cap, the volume is from about 3 ml to about 10 ml, typically about 6 ml. For the lumen of the tube, the volume is from about 15 ml to about 50 ml, typically about 25 ml. Other volumes are within the scope of some embodiments of the present disclosure.

In some embodiments, a solution for preserving cells in one or more bodily fluids, such as saliva and urine, is disclosed. The preservative solution may optionally be used in any of the embodiments. The solution for preserving cells may be beneficial for further separation into cell types and downstream molecular analysis that allows for storage of cells in the body fluid to retain their antigenicity and cellular architecture. The solution may contain at least one chemical fixing agent, such as but not limited to paraformaldehyde, and at least one protease inhibitor. In some embodiments, the solution may further contain one or more of at least one antimicrobial agent, and serum proteins from human and/or other animal species. The solution can be buffered at a pH from between about 6.4 to about 8.4, preferably from between about 7.2 to about 7.6.

For purposes of the disclosure, "preserving cells" means preventing the cells from having their antigens degraded, such that they can be purified or enriched based on their antigens, and preventing alterations in the cellular epigenome. The "epigenome" means the state or pattern of alteration of genomic DNA by covalent modification of the DNA or of proteins bound to the DNA. Examples of such alteration include methylation at the 5 position of cytosine in a CpG dinucleotide, acetylation of lysine residues of histones, the binding of proteins to the DNA to initiate transcription (example: transcription factors) and other heritable or non-heritable changes that do not result from changes in the underlying DNA sequence.

In some embodiments, concentrations of agents in the following description can be those of the sample preserving solution itself. Depending upon the bodily fluid, and in the case of saliva, about an equal volume of solution and body fluid can be mixed together. This preferably results in the cells from the body fluids retaining their antigenicity and DNA integrity for at least one week at room temperature.

In some embodiments of the disclosure, the volume of preservation solution held within the device and deployed may be between about 100 and about 500 ml, which is relevant, for example, for the preservation of cells in urine. As such, the preservation solution for urine may be anywhere between about ten times (10×) concentrated solution to a one-point five times (1.5×) solution for urine.

A "chemical fixing agent", according to some embodiments, is a chemical cross-linking compound used to alter cell components such that the cells resist degradation. The chemical fixing agents can also serve to cross-link histones and other DNA-binding proteins to the DNA. Such agents may be known in the art and include, without limitation, paraformaldehyde, formaldehyde, formalin, aldehydes, alcohol, oxidizing agents, Mercurials, Picrates, Hepes-glutamic acid buffer-mediated organic solvent protection effect (HOPE), fixative combinations such as Zambonis fixative, combinations of aldehydes, and synthetic cross-linking reagents. In some embodiments, the chemical fixing agent is paraformaldehyde. In some embodiments, the chemical fixing agent is present at a concentration of about 1% (v/v).

To protect the cells from degradation by proteases present in the body fluids, in some embodiments, the solution can contain at least one protease inhibitor. In some embodiments, the protease inhibitor can be selected from the group consisting of Aspartic protease inhibitors, Cysteine protease inhibitors, Metalloprotease inhibitors, Serine protease inhibitors (e.g., serpins), Threonine protease inhibitors, Trypsin inhibitors, and Kunitz STI protease inhibitor. Some specific, non-limiting, examples include sodium azide, PMSF, Aprotinin, leupeptin, pepstatin, natural or synthetic proteinase inhibitors, and cocktail mixtures of protease inhibitors. Suitable concentrations of these inhibitors can include, without limitation, PMSF (Phenylmethylsulfonyl fluoride) Serine proteases at about 0.1-1 mM, Benzamidine Serine proteases at about 1 mM, Pepstatin A Acid proteases at about 1 µg/ml, Leupeptin Thiol proteases at about 1 µg/ml, Aprotinin Serine proteases at about 5 µg/ml, and Antipain Thiol proteases at about 1 µg/ml. In certain embodiments, the protease inhibitor is sodium azide at a concentration of about 0.01% (w/v).

To prevent damage to the cells from microbial contamination, some embodiments of the solution contain at least one antimicrobial agent. Suitable antimicrobial agents include, without limitation, antibacterial and antifungal antibiotics.

Preservation of cell architecture is enhanced by the presence of serum proteins, which may optionally be added to the solution in some embodiments. Additionally serum proteins may be used to neutralize osmotic difference between cells and solution. These can be from human or other animal sources. In some cases, whole serum may be used. For example, fetal bovine serum may be added, in some embodiments at about 1% (v/v).

The solution according to the present disclosure may include any combination of the foregoing embodiments.

In some embodiments of the disclosure, a method for preserving cells in one or more bodily fluids is disclosed. The method for preserving the cells can comprise contacting the body fluids with the solution according to the present disclosure. The body fluids can contain a variety of cell types and the cells in the body fluids can be preserved by the solution according to the present disclosure. While not critical to the present disclosure, a ratio of solution to body fluids of from about 1 to 1 is typically used.

The following examples are intended to further illustrate some embodiments of the solutions and methods for preserving cells in body fluids and are not to be construed to limit the scope of this disclosure.

For example, a solution of PBS pH 7.4, 1% Paraformaldehyde, 1% FBS, and 0.01% NaN3 can be added at a 1:1 ratio with saliva, then T-cells can be purified and DNA extracted. The results of such a process are shown FIG. 8 of WO 2012/177656. These results can demonstrate that the integrity of the antigenicity and DNA of T-cells was maintained for at least one week.

Figure 58:
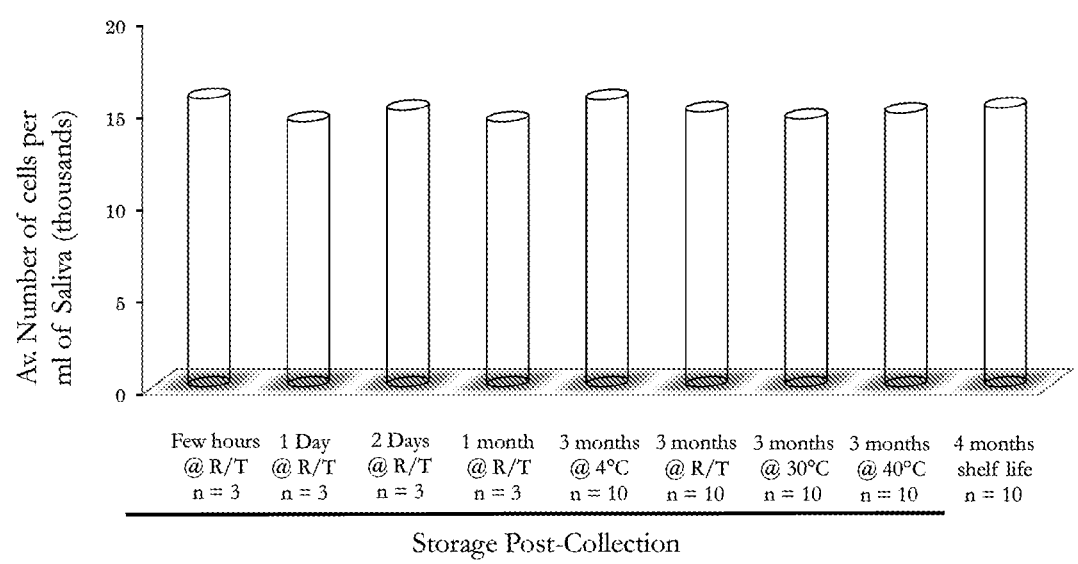
FIG. 58 is a graph demonstrating the preservation of T-cells in a saliva sample contacted by a preservation solution, according to some embodiments.

As shown in the accompanying FIG. 58, further testing has demonstrated the efficacy of the solution in preserving T-cells in a saliva sample for extended durations, even at elevated temperature, and even after an extended shelf life.

In FIG. 58, the vertical axis represents the number of T-cells (in thousands) per ml of a saliva sample mixed with the preservation solution in a 1:1 ratio, as determined by analysis. The cell concentration is effectively halved compared to the original saliva sample, as a result of the 1:1 mix with the preservation solution.

The first (leftmost) column indicates the number of cells in three samples stored a room temperature for a few hours after sample collection and mixing with the preservation solution. The first column acts as a benchmark for assessing the cell numbers in other samples.

The second, third and fourth columns compare the number of cells in three groups of three samples each, stored at room temperature for a day, two days and 1 month, respectively, after sample collection and mixing with the preservation solution. The second to third columns show very little variation with each other or with the first column.

The fifth, sixth, seventh and eighth columns compare the number of cells in groups of ten samples each, stored for a period of three months after sample collection and mixing with preservative solution, kept respectively at 4° C., room temperature, 30° C. and 40° C. Ten samples (instead of three samples) were used, because the test was focused on long-term preservation. The fifth to eight columns show very little variation with each other or with the first column.

The final column repeats the test for the second column, using a sample group of ten samples, and using a preservation solution that has been stored (pre-use shelf-term) for 4 months. As above, ten samples (instead of three samples) were used, because the test was focused on demonstrating extended shelf life.

The graph illustrates that the preservative solution is highly effective, to preserve T-cells in a saliva solution for an extended duration, over a wide range of temperature conditions, and even after an extended shelf-term. The solution may have a similar or corresponding preservation capability for other types of cells. The deviation amongst the cell numbers in the different columns can be explained at least by the usual differences in cell numbers from different people donating the samples and/or different samples even from the same person. The number of cells per ml is also eminently satisfactory for permitting downstream cell analysis.

Further information regarding the construction and use of the sample collection device, preservative solution, and downstream analysis may be found in the aforementioned WO 2012/177656 already incorporated herein by reference in its entirety.

Figure 59:
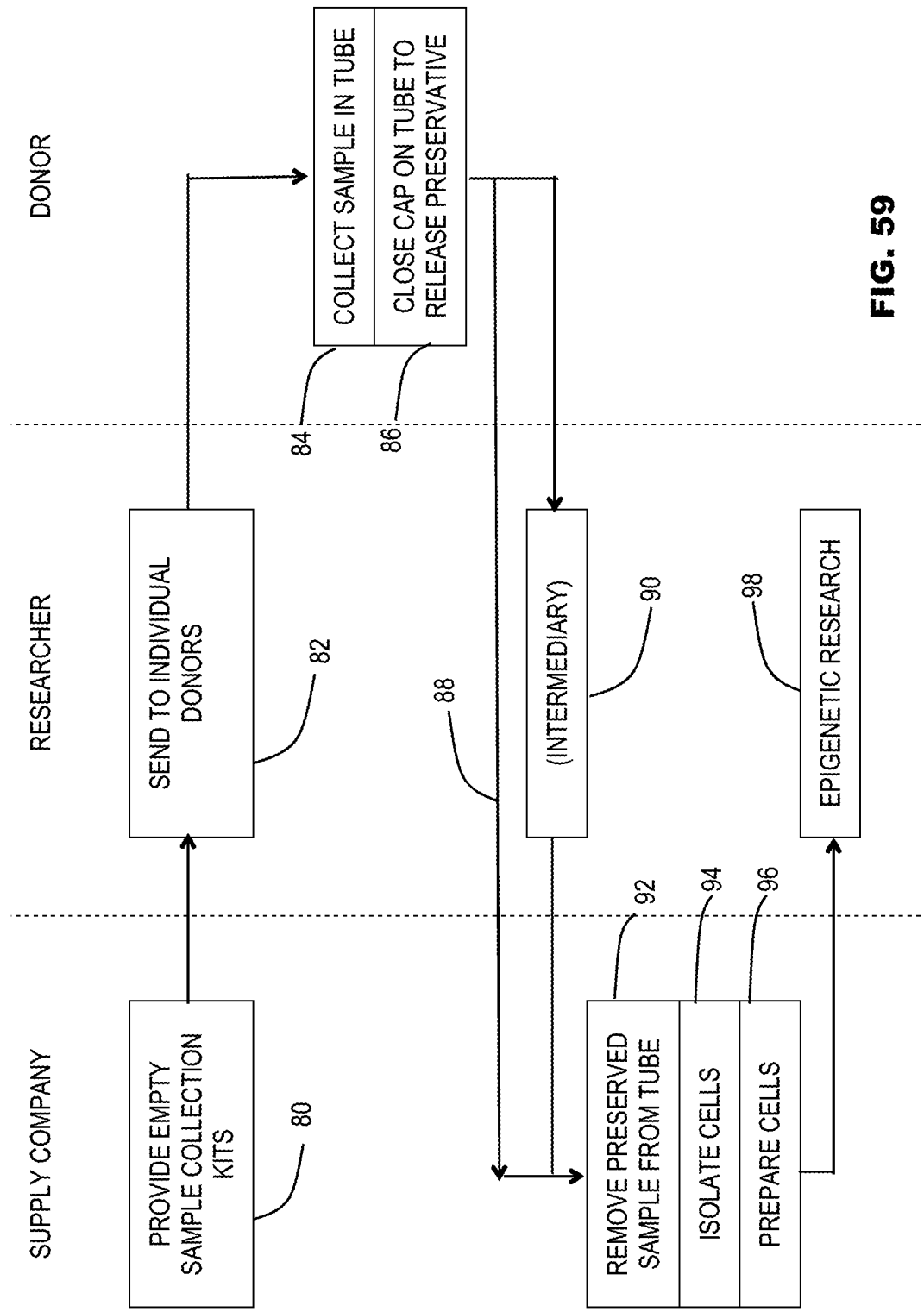
FIG. 59 is a schematic flow diagram illustrating a process for organizing shipping, filling, and processing of sample collection devices, according to some embodiments.

FIG. 59 depicts one manner in which sample collection devices (optionally as described herein) may be used to provide a flexible technique for sample collection from, for example, home based donors. The diagram depicts how a researcher or diagnostic professional wishing to conduct cell diagnosis, epigenetic research or other analysis may be able to benefit from a procedure enabling sample collection devices to be supplied, collected and processed At step 80, a supply company may provide sample collection kits including, for example, a tube 14, a cap 12, and instructions for use. The kits may be supplied to the researcher or diagnosis professional upon request. At step 82, the researcher/diagnosis professional may send individual kits to individual donors, for example, by post or other delivery technique. Each donor may collect a sample of naturally expressed bodily fluid within the tube (step 84), and close the tube by fitting the cap (step 86). The step of fitting cap releases the reagent within the tube to preserve cells within the collected sample. The donor may collect the sample in a home environment. The bodily fluid may, for example, be saliva.

After closing the tube, the donor returns the sample collection device, for example, by post or by other delivery technique. In some embodiments, the donor may return the device directly to the supply company (step 88), or via the researcher/diagnosis professional as an intermediary (step 90). In the latter case, the researcher/diagnosis professional may collect returned samples from multiple donors, and forward these in batches to the supply company.

The supply company processes the returned devices by removing the preserved sample from the tube (step 92), isolating cells from the sample (step 94), and preparing the cells for sending to the researcher (step 96). The step of removing the sample from the tube may optionally comprise using automated machinery to open the sample collection device and extract the sample. The step of isolating the cells may optionally include any of the techniques described in the aforementioned WO 2012/177656. The step 96 of preparing the cells may optionally include freezing the cells.

At step 98, the prepared cells may be sent to the researcher/diagnosis professional for research, diagnosis or analysis, for example, epigenetic research or analysis.

In some embodiments, a serial number system may be used for identifying each sample collection device, and its associated bodily fluid sample. For example, each sample collection device may be assigned a serial number. The serial number may optionally be assigned during manufacture of the sample collection device. The serial number may, for example, be printed on one or more (or all) components of the sample collection device during manufacture, or on a label affixed to the sample collection device. Alternatively, the serial number may be assigned by the researcher while processing the kits before sending to individual donors at step 82. During processing of the collected samples (steps 92-96), the samples may be identified by the serial number of the collection device. The same serial number may be used to identify the isolated and prepared cells finally returned to the researcher for step 98.

It will be appreciated that the foregoing description is merely illustrative of preferred embodiments of the disclosed inventions, and that many improvements, alternatives and/or equivalents may be used.

By way of example only, a non-limiting hierarchical summary of certain features in some embodiments is as follows:

Item/Embodiment

An embodiment represented in a bodily fluid sample collection device for the collection of naturally expressed bodily fluids, comprising a cap engageable with a tube to close a mouth of the tube, the cap comprising a first cap portion defining at least partly a chamber for containing a reagent, and the tube defining at least partly a sample collection space for receiving the naturally expressed bodily fluid; wherein the cap further comprises a second cap portion defining a closure for closing an aperture communicating with the chamber, the second cap portion being configured, in use responsive to fitting the cap to the tube, to disengage from the first cap portion, and descend at least partly into the tube.

The device of embodiment 1, wherein the first and second cap portions are relatively movable with respect to each other, the first and second cap portions being configured such that, responsive to engagement of the cap on the tube, one of the cap portions is caused to move relative to the other cap portion to open the chamber and permit fluid communication between the chamber and the sample collection space, whereby a reagent in the chamber is permitted to mix with the bodily fluid in the sample collection space.

The device of embodiment 2, wherein the second cap portion is configured, upon relative movement with respect to the first cap portion, to translate in a direction towards the sample collection space in response to the relative movement between the first and second cap portions.

An embodiment represented in a bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions relatively movable with respect to each other, the first and second cap portions being configured such that, responsive to engagement of the cap on the tube, one of the cap portions is caused to move relative to the other cap portion to open the chamber and permit fluid communication between the chamber and the sample collection space, whereby a reagent in the chamber is permitted to mix with the bodily fluid in the sample collection space; and wherein the second cap portion is configured to translate in a direction towards the sample collection space in response to the relative movement between the first and second cap portions.

The device of embodiment 2, 3 or 4, wherein the first and second cap portions are configured such that, responsive to engagement of the cap on the tube, one of the cap portions is caused to move integrally relative to the other cap portion.

The device of any preceding embodiment, wherein the second cap portion is integrally coupled to, or captively coupled to, or integral with, the first cap portion.

The device of embodiment 7, wherein the second cap portion s coupled to the first cap portion by a tether.

The device of embodiment 7 or 8, wherein the first cap portion is provided with a cage for retaining the second cap portion captively coupled to the first cap portion.

The device of embodiment 9, wherein the cage is rotatable with respect to the first cap portion.

The device of any preceding embodiment, wherein the tube comprises a support for preventing the second cap portion from dropping into the sample collection space.

The device of any preceding embodiment, wherein the tube has a sample collection portion having a smaller interior cross-sectional area than at a mouth for receiving a cap for closing the device.

The device of embodiment 12, wherein the cross-section area of the sample collection space is too small to accommodate the second cap portion, whereby the second cap portion is obstructed from dropping down into the sample collection space.

The device of embodiment 12 or 13, wherein the sample collection portion has a shape selected from: columnar; annular; toroid.

The device of any preceding embodiment, wherein the sample collection portion bears at least one mark indicating sample volume and/or a fill level.

The device of any preceding embodiment, wherein the cap is securable to a mouth portion of the tube, the mouth portion being separable from a collection portion the tube, to facilitate opening of the device after the cap has been secured.

The device of embodiment 16, wherein the cap is a separate body from the mouth portion, and securable thereto to close the mouth portion.

The device according to any preceding embodiment, wherein the second cap portion comprises or is provided with a feature for permitting retrieval of the second cap portion from a dropped down position in the tube.

The device according to embodiment 18, wherein feature is a magnetic element.

The device according to embodiment 86 or 87, wherein the feature is a blind hole.

The device of any preceding embodiment, and configured to provide to the user a first signal indicative of the chamber having been opened, and a second signal indicative of the cap having reached a closed and/or locked position.

An embodiment represented in an apparatus comprising a bodily fluid sample collection device for the collection of naturally expressed bodily fluids, the device comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions configured such that, responsive to engagement of the cap on the tube, one of the cap portions is caused to drop down into the tube and thereby open the chamber and permit fluid communication between the chamber and the sample collection space, whereby a reagent in the chamber is permitted to mix with the bodily fluid in the sample collection space; and a retrieval tool for retrieving the second cap portion from the tube once the first cap portion has been subsequently removed to open the device to access the collected sample.

A retrieval tool for retrieving a second cap portion from a bodily fluid sample collection device of a type comprising a tube having a mouth closed by a first cap portion, the tube containing a second cap portion that has at least partly separated from the first cap portion, and the tube containing a preserved sample of bodily fluid, the retrieval tool comprising a magnetic and/or mechanical feature for engaging the second cap portion, for retrieving the second cap portion from the tube once the first cap portion has been removed, to permit access to the sample of bodily fluid.

The retrieval tool of embodiment 23, wherein the tool comprises a plurality of distensible fingers for mechanically engaging a blind hole of the second cap portion.

The retrieval tool of embodiment 24, wherein the tool comprises a tubular stem in which a gripper member is reciprocally movable, the gripper member comprising the distensible fingers.

A bodily fluids sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; the device being configured to open the chamber responsive to engagement of the cap on the tube, for allowing the reagent to enter the sample collection space; and wherein the device is configured to provide to the user a first signal indicative of the chamber having been opened, and a second signal indicative of the cap having reached a closed and/or locked position.

The device of embodiment 21 or 26, wherein the first signal comprises any one or a combination of two or more of: a visual signal, an audible signal, a tactile signal.

The device of embodiment 21, 26 or 27, wherein the second signal comprises any one or a combination of two or more of: a visual signal, an audible signal, a tactile signal.

The device of embodiment 21, 26, 27 or 28, wherein the cap comprises first and second cap portions together defining at least partly the chamber, wherein the second cap portion is configured to drop at least partly into the tube to open the chamber, and the first signal is provided by the dropping down of the second cap portion.

The device of any of embodiments 21 or 26 to 29, wherein the cap further comprises a lock device engageable upon the cap reaching a fully closed position of the tube, the lock device configured for locking the cap in the fully closed position, and wherein the second signal is generated by operation of the lock device.

The device of any of embodiments 1 to 21, or 26 to 29, wherein the second cap portion comprises at least a portion having a top-hat shape, comprising a cup portion defining a cavity, and a flange encircling the cup portion.

An embodiment represented in a bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions configured such that, responsive to engagement of the cap on the tube, one of the cap portions is caused to move relative to the other cap portion to open the chamber and permit fluid communication between the chamber and the sample collection space, whereby a reagent in the chamber is permitted to mix with the bodily fluid in the sample collection space; wherein the second cap portion comprises at least a portion having a top-hat shape, comprising a cup portion defining a cavity, and a flange encircling the cup portion.

The device of embodiment 31 or 32, wherein the second cap portion carries a thread on a radially outwardly facing surface, for engaging a radially inwardly facing thread of the first cap portion.

The device of embodiment 31, 32 or 33, wherein the cup portion is configured for entering the open end of the chamber for closing the chamber.

The device of any or embodiments 1 to 21 or 26 to 34, wherein a first amount of rotation to fully secure the cap to the tube is not more than three turns, and wherein a second amount of rotation between the first and second cap portions to open the chamber is less than the first amount of rotation.

An embodiment represented in a bodily fluid sample collection device for the collection of naturally expressed bodily fluids comprising a cap threadedly engageable with a tube to close a mouth of the tube, the cap comprising a chamber for containing a reagent, and the tube defining at least partly a sample collection space for receiving the naturally expressed bodily fluid; wherein the cap comprises first and second cap portions threadedly coupled together and configured such that, responsive to engagement of the cap on the tube, one of the cap portions is caused to move rotatably relative to the other cap portion to open the chamber and permit fluid communication between the chamber and the sample collection space, whereby a reagent in the chamber is permitted to mix with the bodily fluid in the sample collection space, wherein a first amount of rotation to fully secure the cap to the tube is not more than three turns, and wherein a second amount of rotation between the first and second cap portions to open the chamber is less than the first amount of rotation.

The device of embodiment 35 or 36, wherein the first amount of rotation is at least one selected from: not more than two and a half turns; not more than two turns; not more than one and a half turns; not more than one turn.

The device of embodiment 35, 36 or 37, wherein the second amount of rotation is at least one selected from: mot more than one turn; not more than three-quarters of a turn; not more than half a turn; not more than a quarter of a turn.

The device of embodiment 35, 36, 37 or 38, wherein the second amount of rotation comprises a first angular segment for an engager of the tube to cooperate with the second cap portion to restrain the second cap portion against rotation with respect to the tube, and a second angular segment for the threaded coupling between the first and second cap portions to unscrew.

The device of embodiment 39, wherein the first angular segment s selected from: not more than about a quarter of a turn, or not more than about half a turn; and the second angular segment is selected from: not more than about a quarter of a turn, or nor more than about half a turn.

The device of any of embodiments 1 to 21 or 26 to 40, wherein the cap comprises a cap shell and a self-contained chamber module assembled to the cap shell, the self-contained chamber module defining the chamber.

An embodiment represented in a bodily fluid sample collection device, optionally according to any of embodiments 1 to 21 or 26 to 41, the device for the collection of naturally expressed bodily fluids comprising a cap engageable with a tube to close a mouth of the tube, the tube defining at least partly a sample collection space for receiving the naturally expressed body fluid, the device (optionally the cap, or optionally the tube) further comprising a chamber for containing a reagent for mixing with a collected sample; wherein the cap comprises a first body by which a user manipulates the cap, a second body that is rotatably mateable with the tube for securing the cap to the tube and a coupling between the first and second bodies configured for (i) transmitting torque from the first body to the second body for permitting rotation of the second body to secure the second body to the tube, and (ii) permitting slippage between the bodies after the second body has reached a fully secured position; the device further comprising a mechanism operable to cause the chamber to be opened in response to manual rotation of the first body at least after the second body has reached the fully secured position.

The device of embodiment 42, wherein the mechanism is operable to begin to cause the chamber to be opened only after the second body has reached the fully secured position.

The device of embodiment 42, wherein the mechanism is operable partly before the second body has reached the fully secured position.

An embodiment represented in a bodily fluid sample collection device, optionally according to any of embodiments 1 to 21 or 26 to 44, the device for the collection of naturally expressed bodily fluids comprising a cap engageable with a tube to close a mouth of the tube, the tube defining at least partly a sample collection space for receiving the naturally expressed body fluid, the device comprising a chamber for containing a reagent for mixing with a collected sample; wherein the device further comprises a manually operable actuator operable from outside the device at least once the cap has been secured to the tube, for causing the chamber to be opened in response to manual actuation of the actuator.

The device of embodiment 45, wherein the chamber is disposed at a position selected from: on the cap; or on the tube.

The device of embodiment 45 or 46, wherein the manually operable actuator is disposed at a position selected from: on the cap; or on the tube.

An embodiment represented in an apparatus comprising: a device according to embodiment 47; and packaging in which the device is intended to be placed, the packaging configured to accept the device only in a condition in which the actuator has been actuated to cause the chamber to be opened.

A bodily fluid sample collection device, optionally according to any of embodiments 1 to 21 or 26 to 47, the device comprising a tube, and a cap securable to a mouth portion of the tube, the tube defining at least partly a sample collection space for receiving the naturally expressed body fluid, and the device comprising a chamber for containing a reagent for mixing with a collected sample; wherein the mouth portion is separable from a collection portion the tube, to facilitate opening of the device after the cap has been secured.

The device of embodiment 49, wherein the chamber is disposed at a position selected from: on the cap; or on the tube.

The device of embodiment 49 or 50, further comprising a lock mechanism for obstructing removal of the cap once the cap has been fitted to the mouth portion of the tube.

The device of embodiment 49, 50 or 51, wherein the cap is a separate body from the mouth portion, and securable thereto to close the mouth portion.

A bodily fluid sample collection device, optionally according to any of embodiments 1 to 21, or 26 to 47, or 49 to 52, the device for the collection of naturally expressed bodily fluids comprising a cap engageable with a tube to close a mouth of the tube, the cap comprising a first cap portion defining at least partly a chamber for containing a reagent, and the tube defining at least partly a sample collection space for receiving the naturally expressed bodily fluid; wherein the cap further comprises a second cap portion defining a closure for closing an aperture at a lower end of the chamber, the second cap portion having a cup shape.

The device of embodiment 53, wherein the second cap portion configured to disengage from the first cap portion responsive to fitting the cap to the tube.

A bodily fluid sample collection device, optionally according to any of embodiments 1 to 21, or 26 to 47, or 49 to 54, the device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions relatively rotatable with respect to each other, the first and second cap portions being configured such that, responsive to engagement of the cap on the tube, one of the cap portions is caused to rotate relative to the other cap portion to break the integrity of a frangible wall portion of the chamber, to open the chamber and permit fluid communication between the chamber and the sample collection space, whereby a reagent in the chamber is permitted to mix with the bodily fluid in the sample collection space.

A bodily fluid sample collection device, optionally according to any of embodiments 1 to 21, or 26 to 47, or 49 to 55, the device for the collection of naturally expressed bodily fluids, comprising a cap engageable with a tube to close a mouth of the tube, the device further comprising a chamber for containing a reagent, and the tube defining at least partly a sample collection space for receiving the naturally expressed bodily fluid; wherein the chamber is defined at least partly by a variable volume and/or shape chamber unit having a frangible wall portion; in use the chamber is at least partly deformed in response to fitting the cap to the tube, such that the integrity of the frangible wall portion is broken, allowing the contents of the chamber to be dispensed into the sample collection space.

The device of embodiment 56, further comprising a piercing element for breaking the integrity of the frangible wall portion upon the frangible wall portion contacting the piercing element in response to deformation of the chamber.

The device of embodiment 57, wherein the piercing element is provided inside the chamber.

The device of embodiment 56, 57, or 58, wherein the variable volume and/or shape chamber unit comprises at least one selected from: a bladder; a bellows; an accordion.

The device of any of embodiments 56 to 59, wherein in use the chamber is at least partly deformed by compression of the chamber in at least one direction, in response to fitting the cap to the tube.

A bodily fluid sample collection device, optionally according to any of embodiments 1 to 21, or 26 to 47, or 49 to 60, the device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions joined by a frangible wall portion, the first and second cap portions and the frangible wall portion together defining at least partly the chamber and being integrally molded together, the cap configured such that, responsive to engagement of the cap on the tube, one of the cap portions is caused to move relative to the other cap portion to break the frangible wall portion and thereby open the chamber and permit fluid communication between the chamber and the sample collection space, whereby a reagent in the chamber is permitted to mix with the bodily fluid in the sample collection space.

A bodily fluid sample collection device, optionally according to any of embodiments 1 to 21, or 26 to 47, or 49 to 61, the device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions joined by a weld or adhesive bond, the first and second cap portions together defining at least partly the chamber and being integrally molded together, the cap configured such that, responsive to engagement of the cap on the tube, one of the cap portions is caused to move relative to the other cap portion to break the weld or adhesive bond and thereby open the chamber and permit fluid communication between the chamber and the sample collection space, whereby a reagent in the chamber is permitted to mix with the bodily fluid in the sample collection space.

The device according to any of embodiments 1 to 21, or 26 to 47, or 49 to 62, further comprising a second chamber for containing a second reagent separately from the reagent of the first chamber.

A bodily fluid sample collection device for the collection of naturally expressed bodily fluids, comprising a cap engageable with a tube to close a mouth of a tube, the device further comprising a plurality of chambers for containing reagents or reagent components separately from one another, and an opener for opening the chambers to dispense the contents of the chambers into a sample collection space of the tube when the cap is fitted to close the mouth of the tube.

The device of embodiment 63 or 64, wherein the opener is configured to cause opening of one chamber before another, to define sequential release of the chambers' contents into the sample collection space.

The device of embodiment 63 or 64, wherein the opener is configured to cause substantially simultaneous opening of one chamber before another, to define substantially simultaneous release of the chambers' contents into the sample collection space.

The device of embodiment 63, 64, 65 or 66, wherein at least one, and optionally first and second, of the plurality of chambers is or are provided in the cap.

The device of embodiment 63, 64, 65, 66 or 67, wherein the opener comprises at least one cap portion configured to move relative to another cap portion when the cap is engaged to the mouth of the tube.

A bodily fluid sample collection device, optionally according to any of embodiments 1 to 21, or 26 to 47, or 49 to 68, the device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions relatively movable with respect to each other, the first and second cap portions being configured such that, responsive to engagement of the cap on the tube, one of the cap portions is caused to move integrally relative to the other cap portion to open the chamber and permit fluid communication between the chamber and the sample collection space, whereby a reagent in the chamber is permitted to mix with the bodily fluid in the sample collection space.

A bodily fluid sample collection device, optionally according to any of embodiments 1 to 21, or 26 to 47, or 49 to 69, the device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions configured such that, responsive to engagement of the cap on the tube, one of the cap portions is caused to move relative to the other cap portion to open the chamber and permit fluid communication between the chamber and the sample collection space, whereby a reagent in the chamber is permitted to mix with the bodily fluid in the sample collection space.

The device of embodiment 69 or 70, wherein the first and second cap portions are rotatably movable with respect to each other.

The device of embodiment wherein the first and second cap portions are threadedly coupled together.

The device of any of embodiments wherein the cap is rotatably engageable on the tube.

The device of embodiment 73, wherein the cap is threadedly engageable on the tube.

The device of any of embodiments 69 to 74, wherein the first and second cap portions are rotatable about an axis that is generally parallel with an axis about which the cap is rotatable when fastening the cap to the tube.

The device of embodiment 75, wherein the axes are generally coincident.

The device of any of embodiments 69 to 76, wherein the tube comprises a first engager for engagement by the first cap portion, and a second engager for engagement by the second cap portion.

The device of embodiment wherein the first engager comprises a component of a threaded coupling.

The device of embodiment 77 or 78, wherein the second engager comprises a restrainer for restraining the second cap portion from relative rotation with respect to the tube.

The device of embodiment 77, 78 or 79, wherein in use one of the first and second engagers is configured to engage a respective cap portion before the other engager engages its respective cap portion, said other engager engaging its respective cap portion after relative movement between the cap and the tube.

The device of embodiment 80, wherein the second engager is configured to be keyed to engage the second cap portion before engagement between the first engager and the first cap portion.

The device of embodiment 80, wherein the second engager is configured to engage the second cap portion after the first cap portion has been fitted to engage the first engager.

The device of embodiment 77, 78 or 79, wherein the first and second engagers are configured to engage the respective cap portions generally simultaneously during engagement of the cap with the tube.

The device of any of embodiments 69 to 83, wherein the tube is configured to engage the first and second cap portions such that, during fastening of the cap to the tube, one of the first and second cap portions is at least partly restrained against movement relative to the tube while the other cap portion moves relative to the tube.

The device of any of embodiments 69 to 84, wherein the first and second cap portions are coupled together by a coupling which causes or permits relative axial displacement between the cap portions responsive to relative rotation.

The device of any of embodiments 69 to 85, wherein the second cap portion is releasable from the first cap portion to open the chamber.

The device of any of embodiments 69 to 85, wherein the second cap portion is integrally coupled to, or captively coupled to, or integral with, the first cap portion.

The device of embodiment 87, wherein the second cap portion is coupled to the first cap portion by a tether.

The device of embodiment 87 or 88, wherein the first cap portion is provided with a cage for retaining the second cap portion captively coupled to the first cap portion.

The device of embodiment 89, wherein the cage is rotatable with respect to the first cap portion.

The device of any of embodiments 69 to 90, wherein the second cap portion comprises a closure for closing an aperture of the chamber.

The device of embodiment 91, wherein the second cap portion has or comprises a generally cup-shape.

The device of embodiment 91 or 92, wherein the chamber has an open lower end.

The device of embodiment 91, 92 or 93, wherein at least a portion of the second cap portion drops into or towards the sample collection space of the tube when the second cap portion is disengaged from the first cap portion.

The device of any of embodiments 69 to 94, wherein the e second cap portion is configured to translate in a direction towards the sample collection space in response to the relative movement between the first and second cap portions.

The device of any of embodiments 69 to 95, wherein the second cap portion is configured, upon relative movement with respect to the first cap portion, to break the integrity of a frangible wall portion of the chamber, to open the chamber.

The device of embodiment 96, wherein the frangible wall portion comprises material selected from: plastics; metal; a plastics/metal laminate.

The device of embodiment 96 or 97, wherein the frangible wall portion is an integral wall portion joining the first and second cap portions.

The device of embodiment 96, 97 or 98, wherein the second cap portion comprises a piercing and/or cutting element for breaking the integrity of the frangible wall portion.

The device of any of embodiments 96 to 99, wherein the frangible wall portion is selected as one or more of: a blister defining the chamber; a closure sealed to close an aperture of the chamber; an integral part of at least one of the cap portions; a foil welded or glued at an aperture of the chamber.

The device of any of embodiments 96 to 100, wherein the chamber is defined by a variable volume and/or shape chamber unit having at least one movable wall portion.

The device of embodiment 101, wherein the frangible wall portion s a wall portion of the variable volume and/or shape chamber unit.

The device of embodiment 101, wherein the frangible wall portion is a said movable wall portion of the variable volume and/or shape chamber unit.

The device of any of embodiments 101 to 103, wherein the variable volume and/or shape chamber unit comprises at least one selected from: a bladder; a bellows; an accordion.

The device of any of embodiments 101 to 104, further comprising a cutting and/or piercing element for breaking the integrity of the frangible wall portion.

The device of embodiment 105, wherein the cutting and/or piercing element for breaking the integrity of the frangible wall portion is provided inside the variable volume and/or shape chamber unit.

The device of embodiment 105 or 106, wherein the cutting and/or piercing element is configured to break the integrity of the movable wall portion of the variable volume and/or shape chamber unit when the movable wall portion moves in response to compression of the chamber.

The device of any of embodiments 69 to 107, wherein the first and second cap portions are joined by adhesive or welding, the join being configured to break in response to said relative movement between the first and second cap portions when the cap is engaged on the tube.

The device of any of embodiments 69 to 107, wherein the cap comprises a cap shell and a self-contained chamber module assembled to the cap shell, the self-contained chamber module defining the chamber.

The device of any of embodiments 69 to 108, and configured to provide to the user a first signal indicative of the chamber having been opened, and a second signal indicative of the cap having reached a closed and/or locked position.

The device of embodiment 109, wherein at least one of the first and second signals comprises any one or a combination of two or more of: a visual signal, an audible signal, a tactile signal.

The device of embodiment 109 or 110, wherein the first signal is generated by dropping down of the second cap portion at least partly into the tube.

The device of embodiment 109, 110 or 111, wherein the second signal is generated by engagement of a lock mechanism operative to lock the cap in a fully closed condition.

The device of embodiment 112, wherein the lock mechanism comprises at least one selected from: a latch; a ratchet.

The device of any of embodiments 69 to 113, wherein the tube has a sample collection portion having a smaller interior cross-sectional area than at a mouth for receiving a cap for closing the device.

The device of embodiment 114, wherein the sample collection portion bears at least one mark indicating sample volume and/or a fill level.

The device of embodiment 114 or 115, wherein the sample collection portion has a shape selected from: columnar; annular; toroid.

The device of embodiment 114, 115 or 116, wherein the interior cross-sectional area of the sample collection portion is sufficiently small that it prevents the second cap portion from entering the sample collection portion.

The device of any of embodiments 69 to 117, wherein the reagent comprises a preservation solution.

The device of any of embodiments 69 to 118, further comprising a second chamber for containing a second reagent separately from the reagent of the first chamber.

The device of embodiment 119, wherein the second chamber is configured to be opened in use by one or more of: relative movement of the second cap portion; relative movement of a third cap portion.

The device of embodiment 119 or 120, wherein the second chamber is configured to be opened substantially at the same time as the first chamber, or in sequence before or after opening of the first chamber.

An embodiment represented in a solution for preserving cells in bodily fluid for further separation into cell types and downstream epigenetic analysis that allows for storage of cells in bodily fluid to retain their antigenicity and cellular architecture, the solution comprising at least one chemical fixing agent and at least one protease inhibitor, buffered at a pH from about 6.4 to about 8.4, wherein the solution is effective to preserve cells for a duration of at least 1 week.

The solution of embodiment 122, wherein the solution is effective to preserve cells for a duration selected from: at least two weeks; or at least three weeks, or at least a month, or at least two months; or at least three months.

The solution of embodiment 122 or 123, wherein the solution is effective to preserve cells when kept at a temperature selected as at least one of the following temperatures or temperature ranges: between 4° C. and 40° C.; between 4° C. and 30° C.; about room temperature; about 4° C.; about 30° C.; about 40° C.

The solution of embodiment 122, 123 or 124, wherein the solution has a shelf-life selected from at least one of the following: at least 1 month; at least two months; at least three months; at least four months.

The solution of embodiment 125, wherein the shelf-life is shelf-life at room temperature.

The solution of any of embodiments 122 to 126, wherein the solution is effective to preserve at least a predetermined percentage of cells from an original sample of the body fluid, the predetermined percentage being selected from: at least 50%, at least 55%, at least 60%, at least 65%, at least 70%, at least 75%, at least 80%, at least 85%, at least 90%, at least 95%.

The solution of any of embodiments 122 to 127, wherein in a number of preserved or a predetermined type, per ml is at least about 5000, or at least about 10000, or at least about 12000.

The solution of any of embodiments 122 to 128, wherein the cells are T-cells.

The solution according to any of embodiments 122 to 129, further comprising one or more of at least one antimicrobial agent and serum proteins from human and/or other animal species.

The solution according to any of embodiments 122 to 130, wherein the chemical fixing agent is selected from the group consisting of aldehydes.

The solution according to embodiment 131, wherein the chemical fixing agent is paraformaldehyde.

The solution according to any of embodiments 122 to 132, wherein the chemical fixing agent is present at a concentration of about 1% (v/v).

The solution according to any of embodiments 122 to 133, wherein the antimicrobial agent is selected from the group consisting of antibacterial and antifungal antibiotics.

The solution according to any of embodiments 122 to 134, wherein the protease inhibitor is selected from the group consisting of: Aspartic protease inhibitors, Cysteine protease inhibitors, Metallo protease inhibitors, Serine protease inhibitors, Threonine protease inhibitors, Trypsin inhibitors, Kunitz STI protease inhibitor and a combination of any of the foregoing.

The solution according to any of embodiments 122 to 135, wherein the protease inhibitor is selected from the group consisting of: sodium azide, PMSF, aprotinin, leupeptin, pepstatin, natural or synthetic proteinase inhibitors, mixtures of protease inhibitors both natural and synthetic, and any combination of the foregoing.

The solution according to any of embodiments 122 to 136, wherein the protease inhibitor is sodium azide.

The solution according to any of embodiments 122 to 137, wherein the solution is buffered at a pH of from about 7.2 to about 7.6.

The solution according to any of embodiments 122 to 138, wherein the buffer is selected from the group consisting of: barbital, trisphosphate, citrate, cacodylate, other non-phosphate buffers and any combination of the foregoing.

The solution according to any of embodiments 122 to 139, wherein the buffer is a phosphate buffer.

A method for preserving cells in a naturally expressed bodily fluid comprising contacting the bodily fluid with the preservation solution according to any of embodiments 122 to 140.

A sample collection device, optionally according to any of embodiments 1 to 21, or 26 to 47, or 49 to 121, the device for collection of a naturally expressed bodily fluid, the sample collection device containing a preservation solution according to any of embodiments 122 to 140.

A sample collection kit including a solution as defined in any of embodiments 122 to 140.

A sample collection kit including a sample collection device as defined in any of embodiments 1 to 21, or 26 to 47, or 49 to 121.

The kit of embodiment 143 or 144 for collection of a bodily fluid sample from which cells and/or DNA may be isolated for analysis.

The kit of embodiment 145, further comprising a reagent in the device, the reagent configured to preserve cells and/or cell components.

Use of a device as defined in any of embodiments 1 to 21, or 26 to 47, or 49 to 121, for collecting a bodily fluid sample for analysis of cells or cellular components, the analysis selected from: genetics; epigenetics, diagnostics; or other purposes.

An embodiment represented in a method comprising: providing at least one sample collection kit for collecting a naturally expressed sample of bodily fluid, the kit optionally according to any of embodiments 143 to 146, the sample collection kit comprising a sample collection device and instructions for use, the sample collection device comprising a tube, a cap engageable with the tube to close a mouth of the tube, and a preservative for preserving cells of the donated bodily fluid sample, the preservative being contained in a chamber of the device that is configured to be opened automatically upon fitting the cap to the tube, to release the preservative into the tube; shipping the at least one sample collection kit; receiving at least one sample collection device contained a bodily fluid sample; extracting the bodily fluid sample from the collection device; processing the sample to isolate cells for epigenetic analysis or diagnostic purpose; and preparing the isolated cells for shipping.

The method of embodiment 148 wherein the collected bodily fluid is saliva.

The method of embodiment 148 or 149, wherein the step of preparing the isolated cells comprises freezing the cells.

A bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions relatively movable with respect to each other, the first and second cap portions being configured such that, responsive to engagement of the cap on the tube, one of the cap portions is caused to move integrally relative to the other cap portion to open the chamber and permit fluid communication between the chamber and the sample collection space, Whereby a reagent in the chamber is permitted to mix with the bodily fluid in the sample collection space.

A bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions configured such that, responsive to engagement of the cap on the tube, one of the cap portions is caused to move relative to the other cap portion to open the chamber and permit fluid communication between the chamber and the sample collection space, whereby a reagent in the chamber is permitted to mix with the bodily fluid in the sample collection space.

The device of embodiment 151 or 152, wherein the first and second cap portions are rotatably movable with respect to each other.

The device of embodiment 153, wherein the first and second cap portions are threadedly coupled together.

The device of any of embodiments 151 to 154, wherein the cap is rotatably engageable on the tube.

The device of embodiment 155, wherein the cap is threadedly engageable on the tube.

The device of any of embodiments 151 to 156, wherein the first and second cap portions are rotatable about an axis that is generally parallel with an axis about which the cap is rotatable when fastening the cap to the tube.

The device of embodiment 157, wherein the axes are generally coincident.

The device of any of embodiments 151 to 158, wherein the tube comprises a first engager for engagement by the first cap portion, and a second engager for engagement by the second cap portion.

The device of embodiment 159, wherein the first engager comprises a component of a threaded coupling.

The device of embodiment 159 or 160, wherein the second engager comprises a restrainer for restraining the second cap portion from relative rotation with respect to the tube.

The device of embodiment 159, 160 or 161, wherein in se one of the first and second engagers is configured to engage a respective cap portion before the other engager engages its respective cap portion, said other engager engaging its respective cap portion after relative movement between the cap and the tube.

The device of embodiment 162, wherein the second engager is configured to be keyed to engage the second cap portion before engagement between the first engager and the first cap portion.

The device of embodiment 162, wherein the second engager is configured to engage the second cap portion after the first cap portion has been fitted to engage the first engager.

The device of embodiment 159, 160 or 161, wherein the first and second engagers are configured to engage the respective cap portions generally simultaneously during engagement of the cap with the tube.

The device of any of embodiments 151 to 165 wherein the tube is configured to engage the first and second cap portions such that, during fastening of the cap to the tube, one of the first and second cap portions is at least partly restrained against movement relative to the tube while the other cap portion moves relative to the tube.

The device of any of embodiments 151 to 166, wherein the first and second cap portions are coupled together by a coupling Which causes or permits relative axial displacement between the cap portions responsive to relative rotation.

The device of any of embodiments 151 to 167, wherein the second cap portion is releasable from the first cap portion to open the chamber.

The device of any of embodiments 151 to 167, wherein the second cap portion is integrally coupled to, or captively coupled to, or integral with, the first cap portion.

The device of embodiment 169, wherein the second cap portion is coupled to the first cap portion by a tether.

The device of embodiment 169 or 170, wherein the first cap portion is provided with a cage for retaining the second cap portion captively coupled to the first cap portion.

The device of embodiment 171, wherein the cage is rotatable with respect to the first cap portion.

The device of any of embodiments 151 to 172, wherein the second cap portion comprises a closure for closing an aperture of the chamber.

The device of embodiment 173, wherein the second cap portion has or comprises a generally cup-shape.

The device of embodiment 173 or 174, wherein the chamber has an open lower end.

The device of embodiment 173, 174 or 175, wherein at least a portion of the second cap portion drops into or towards the sample collection space of the tube when the second cap portion is disengaged from the first cap portion.

The device of any of embodiments 151 to 176, wherein the second cap portion is configured to translate in a direction towards the sample collection space in response to the relative movement between the first and second cap portions.

The device of any of embodiments 151 to 177, wherein the second cap portion is configured, upon relative movement with respect to the first cap portion, to break the integrity of a frangible wall portion of the chamber, to open the chamber.

The device of embodiment 178, wherein the frangible wall portion comprises material selected from: plastics; metal; a plastics/metal laminate.

The device of embodiment 178 or 179, wherein the frangible wall portion is an integral wall portion joining the first and second cap portions.

The device of embodiment 178, 179 or 180, wherein the second cap portion comprises a piercing and/or cutting element for breaking the integrity of the frangible wall portion.

The device of any of embodiments 178 to 181, wherein the frangible wall portion is selected as one or more of: a blister defining the chamber; a closure sealed to close an aperture of the chamber; an integral part of at least one of the cap portions; a foil welded or glued at an aperture of the chamber.

The device of any of embodiments 178 to 182, wherein the chamber is defined by a variable volume and/or shape chamber unit having at least one movable wall portion.

The device of embodiment 183, wherein the frangible wall portion is a wall portion of the variable volume and/or shape chamber unit.

The device of embodiment 182, wherein the frangible wall portion is a said movable wall portion of the variable volume and/or shape chamber unit.

The device of any of embodiments 183 to 185, wherein the variable volume and/or shape chamber unit comprises at least one selected from: a bladder; a bellows; an accordion.

The device of any of embodiments 183 to 186, further comprising a cutting and/or piercing element for breaking the integrity of the frangible wall portion.

The device of embodiment 187, wherein the cutting and/or piercing element for breaking the integrity of the frangible wall portion is provided inside the variable volume and/or shape chamber unit.

The device of embodiment 187 or 188, wherein the cutting and/or piercing element is configured to break the integrity of the movable wall portion of the variable volume and/or shape chamber unit when the movable wall portion moves in response to compression of the chamber.

The device of any of embodiments 151 to 189, wherein the first and second cap portions are joined by adhesive or welding, the join being configured to break in response to said relative movement between the first and second cap portions when the cap is engaged on the tube.

The device of any of embodiments 151 to 190, wherein the cap comprises a cap shell and a self-contained chamber module assembled to the cap shell, the self-contained chamber module defining the chamber.

The device of any of embodiments 151 to 191, and configured to provide to the user a first signal indicative of the chamber having been opened, and a second signal indicative of the cap having reached a closed and/or locked position.

The device of embodiment 192, wherein at least one of the first and second signals comprises any one or a combination of two or more of: a visual signal, an audible signal, a tactile signal.

The device of embodiment 192 or 193, wherein the first signal is generated by dropping down of the second cap portion at least partly into the tube.

The device of embodiment 192, 193 or 194, wherein the second signal is generated by engagement of a lock mechanism operative to lock the cap in a fully closed condition.

The device of embodiment 195, wherein the lock mechanism comprises at least one selected from: a latch; a ratchet.

The device of any of embodiments 151 to 196, wherein the tube has a sample collection portion having a smaller interior cross-sectional area than at a mouth for receiving a cap for closing the device.

The device of embodiment 197, wherein the sample collection portion bears at least one mark indicating sample volume and/or a fill level.

The device of embodiment 197 or 198, wherein the sample collection portion has a shape selected from: columnar; annular; toroid.

The device of embodiment 197, 198 or 199, wherein the interior cross-sectional area of the sample collection portion is sufficiently small that it prevents the second cap portion from entering the sample collection portion.

The device of any of embodiments 151 to 200, wherein the reagent comprises a preservation solution.

The device of any of embodiments 151 to 201, further comprising a second chamber for containing a second reagent separately from the reagent of the first chamber.

The device of embodiment 202, wherein the second chamber is configured to be opened in use by one or more of: relative movement of the second cap portion; relative movement of a third cap portion.

The device of embodiment 202 or 203, wherein the second chamber is configured to be opened substantially at the same time as the first chamber, or in sequence before or after opening of the first chamber.

An embodiment represented in a bodily fluid sample collection device for the collection of naturally expressed bodily fluids comprising a cap engageable with a tube to close a mouth of the tube, the cap comprising a first cap portion defining at least partly a chamber for containing a reagent, and the tube defining at least partly a sample collection space for receiving the naturally expressed bodily fluid; wherein the cap further comprises a second cap portion defining a closure for closing an aperture communicating with the chamber, the second cap portion being configured, in use responsive to fitting the cap to the tube, to disengage from the first cap portion, and descend at least partly into the tube.

A bodily fluid sample collection device for the collection of naturally expressed bodily fluids comprising a cap engageable with a tube to close a mouth of the tube, the cap comprising a first cap portion defining at least partly a chamber for containing a reagent, and the tube defining at least partly a sample collection space for receiving the naturally expressed bodily fluid; wherein the cap further comprises a second cap portion defining a closure for closing an aperture at a lower end of the chamber, the second cap portion having a cup shape, and optionally being configured to disengage from the first cap portion responsive to fitting the cap to the tube.

A bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions relatively rotatable with respect to each other, the first and second cap portions being configured such that, responsive to engagement of the cap on the tube, one of the cap portions is caused to rotate relative to the other cap portion to break the integrity of a frangible wall portion of the chamber, to open the chamber and permit fluid communication between between the chamber and the sample collection space, whereby a reagent in the chamber is permitted to mix with the bodily fluid in the sample collection space.

An embodiment represented in a bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the tube has a sample collection portion having a smaller interior cross-sectional area than at a mouth for receiving a cap for closing the device.

The device of embodiment 208, wherein the sample collection portion bears at least one mark indicating sample volume and/or a fill level.

The device of embodiment 208 or 209, wherein the sample collection portion has a shape selected from: columnar; annular; toroid.

An embodiment represented in a bodily fluid sample collection device for the collection of naturally expressed bodily fluids, comprising a cap engageable with a tube to close a mouth of a tube, the device further comprising a plurality of chambers for containing reagents or reagent components separately from one another, and an opener for opening the chambers to dispense the contents of the chambers into a sample collection space of the tube when the cap is fitted to close the mouth of the tube.

The device of embodiment 211, wherein the opener is configured to cause opening of one chamber before another, to define sequential release of the chambers' contents into the sample collection space.

The device of embodiment 211, wherein the opener configured to cause substantially simultaneous opening of one chamber before another, to define substantially simultaneous release of the chambers' contents into the sample collection space.

The device of embodiment 211, 212 or 213, wherein at least one, and optionally and second, of the plurality of chambers is or are provided in the cap.

The device of embodiment 211, 212, 213 or 214, wherein the opener comprises at least one cap portion configured to move relative to another cap portion when the cap is engaged to the mouth of the tube.

An embodiment represented in a bodily fluid sample collection device for the collection of naturally expressed bodily fluids, comprising a cap engageable with a tube to close a mouth of the tube, the device further comprising a chamber for containing a reagent, and the tube defining at least partly a sample collection space for receiving the naturally expressed bodily fluid; wherein the chamber is defined at least partly by a variable volume and/or shape chamber unit having a frangible wall portion; in use the chamber is at least partly deformed in response to fitting the cap to the tube, such that the integrity of the frangible wall portion is broken, allowing the contents of the chamber to be dispensed into the sample collection space.

The device of embodiment 216, further comprising a piercing element for breaking the integrity of the frangible wall portion upon the frangible wall portion contacting the piercing element in response to deformation of the chamber.

The device of embodiment 217, wherein the piercing element is provided inside the chamber.

The device of embodiment 216, 217, or 218, wherein the variable volume and/or shape chamber unit comprises at least one selected from: a bladder; a bellows; an accordion.

The device of any of embodiments 216 to 219, wherein in use the chamber is at least partly deformed by compression of the chamber in at least one direction, in response to fitting the cap to the tube.

An embodiment represented in a bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions joined by a frangible wall portion, the first and second cap portions and the frangible wall portion together defining at least partly the chamber and being integrally molded together, the cap configured such that, responsive to engagement of the cap on the tube, one of the cap portions is caused to move relative to the other cap portion to break the frangible wall portion and thereby open the chamber and permit fluid communication between the chamber and the sample collection space, whereby a reagent in the chamber is permitted to mix with the bodily fluid in the sample collection space.

An embodiment represented in a bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions joined by a weld or adhesive bond, the first and second cap portions together defining at least partly the chamber and being integrally molded together, the cap configured such that, responsive to engagement of the cap on the tube, one of the cap portions is caused to move relative to the other cap portion to break the weld or adhesive bond and thereby open the chamber and permit fluid communication between the chamber and the sample collection space, whereby a reagent in the chamber is permitted to mix with the bodily fluid in the sample collection space.

An embodiment represented in a bodily fluids sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; the device being configured to open the chamber responsive to engagement of cap on the tube, for allowing the reagent to enter the sample collection space; and wherein the device is configured to provide to the user a first signal indicative of the chamber having been opened, and a second signal indicative of the cap having reached a closed and/or locked position.

The device of embodiment 223, wherein the first signal comprises any one or a combination of two or more of: a visual signal, an audible signal, a tactile signal.

The device of embodiment 223 or 224, wherein the second signal comprises any one or a combination of two or more of: a visual signal, an audible signal, a tactile signal.

The device of embodiment 223, 224 or 225, wherein the cap comprises first and second cap portions together defining at least partly the chamber, wherein the second cap portion is configured to drop at least partly into the tube to open the chamber, and the second signal is provided by the dropping down of the second cap portion.

The device of any of embodiments 222 to 226, wherein the cap further comprises a lock device engageable upon the cap reaching a fully closed position of the tube, the lock device configured for locking the cap in the fully closed position, and wherein the second signal is generated by operation of the lock device.

An embodiment represented in a bodily fluid sample collection device for the collection of naturally expressed bodily fluids comprising a cap threadedly engageable with a tube to close a mouth of the tube, the cap comprising a chamber for containing a reagent, and the tube defining at least partly a sample collection space for receiving the naturally expressed bodily fluid; wherein the cap comprises first and second cap portions threadedly coupled together and configured such that, responsive to engagement of the cap on the tube, one of the cap portions is caused to move rotatably relative to the other cap portion to open the chamber and permit fluid communication between the chamber and the sample collection space, whereby a reagent in the chamber is permitted to mix with the bodily fluid in the sample collection space, wherein a first amount of rotation to fully secure the cap to the tube is not more than three turns, and wherein a second amount of rotation between the first and second cap portions to open the chamber is less than the first amount of rotation.

The device of embodiment 228, wherein the first amount of rotation is at least one selected from: not more than two and a half turns; not more than two turns; not more than one and a half turns; not more than one turn.

The device of embodiment 228 or 229, wherein the second amount of rotation is at least one selected from: mot more than one turn; not more than three-quarters of a turn; not more than half a turn; not more than a quarter of a turn.

The device of embodiments 228, 229 or 230, wherein the second amount of rotation comprises a first angular segment for an engager of the tube to cooperate with the second cap portion to restrain the second cap portion against rotation with respect to the tube, and a second angular segment for the threaded coupling between the first and second cap portions to unscrew.

The device of embodiment 231, wherein the first angular segment is selected from: not more than about a quarter of a turn, or not more than about half a turn; and the second angular segment is selected from: not more than about a quarter of a turn, or nor more than about half a turn.

An embodiment represented in a bodily fluid sample collection device for the collection of naturally expressed bodily fluids comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions configured such that, responsive to engagement of the cap on the tube, one of the cap portions is caused to move relative to the other cap portion to open the chamber and permit fluid communication between the chamber and the sample collection space, whereby a reagent in the chamber is permitted to mix with the bodily fluid in the sample collection space; wherein the second cap portion comprises at least a portion having a top-hat shape, comprising a cup portion defining a cavity, and a flange encircling the cup portion.

The device of embodiment 233, wherein the second cap portion carries a thread on a radially outwardly facing surface, for engaging a radially inwardly facing thread of the first cap portion.

The device of embodiment 233, wherein the cup portion is configured for entering the open end of the chamber for closing the chamber.

The device according to any preceding embodiment, wherein the second cap portion comprises or is provided with a feature for permitting retrieval of the second cap portion from a dropped down position in the tube.

The device according to embodiment 236, wherein feature is a magnetic element.

The device according to embodiment 236 or 237, wherein the feature is a blind hole.

An embodiment represented in an apparatus comprising a bodily fluid sample collection device for the collection of naturally expressed bodily fluids, the device comprising a cap engageable with a tube to close a mouth of the tube, the cap comprising a chamber for containing a reagent, and the tube defining at least partly a sample collection space for receiving the naturally expressed bodily fluid; wherein the cap comprises first and second cap portions configured such that, responsive to engagement of the cap on the tube, one of the cap portions is caused to drop down into the tube and thereby open the chamber and permit fluid communication between the chamber and the sample collection space, whereby a reagent in the chamber is permitted to mix with the bodily fluid in the sample collection space; and a retrieval tool for retrieving the second cap portion from the tube once the first cap portion has been subsequently removed to open the device to access the collected sample.

An embodiment represented in a retrieval tool for retrieving a second cap portion from a bodily fluid sample collection device of a type comprising a tube having a mouth closed by a first cap portion, the tube containing a second cap portion that has at least partly separated from the first cap portion, and the tube containing a preserved sample of bodily fluid, the retrieval tool comprising a magnetic and/or mechanical feature for engaging the second cap portion, for retrieving the second cap portion from the tube once the first cap portion has been removed, to permit access to the sample of bodily fluid.

The retrieval tool of embodiment 240, wherein the tool comprises a plurality of distensible fingers for mechanically engaging a blind hole of the second cap portion.

The retrieval tool of embodiment 241, wherein the toll comprises a tubular stem in which a gripper member is reciprocally movable, the gripper member comprising the distensible fingers.

An embodiment represented in a method comprising: providing at east one sample collection kit for collecting a naturally expressed sample of bodily fluid, the sample collection kit comprising a sample collection device and instructions for use, the sample collection device comprising a tube, a cap engageable with the tube to close a mouth of the tube, and a preservative for preserving cells of the donated bodily fluid sample, the preservative being contained in a chamber of the device that is configured to be opened automatically upon fitting the cap to the tube, to release the preservative into the tube; shipping the at least one sample collection kit; receiving at least one sample collection device contained a bodily fluid sample; extracting the bodily fluid sample from the collection device; processing the sample to isolate cells for epigenetic analysis or diagnostic purpose; and preparing the isolated cells for shipping.

The method of embodiment 243 wherein the collected bodily fluid is saliva.

The method of embodiment 243 or 244, wherein the step of preparing the isolated cells comprises freezing the cells.

An embodiment represented in a bodily fluid sample collection device for the collection of naturally expressed bodily fluids comprising a cap engageable with a tube to close a mouth of the tube, the tube defining at least partly a sample collection space for receiving the naturally expressed body fluid, the device (optionally the cap, or optionally the tube) further comprising a chamber for containing a reagent for mixing with a collected sample; wherein the cap comprises a first body by which a user manipulates the cap, a second body that is rotatably mateable with the tube for securing the cap to the tube and a coupling between the first and second bodies configured for (i) transmitting torque from the first body to the second body for permitting rotation of the second body to secure the second body to the tube, and (ii) permitting slippage between the bodies after the second body has reached a fully secured position; the device further comprising a mechanism operable to cause the chamber to be opened in response to manual rotation of the first body at least after the second body has reached the fully secured position.

The device of embodiment 246, wherein the mechanism is operable to begin to cause the chamber to be opened only after the second body has reached the fully secured position.

The device of embodiment 246, wherein the mechanism is operable partly before the second body has reached the fully secured position.

An embodiment represented in a bodily fluid sample collection device for the collection of naturally expressed bodily fluids comprising a cap engageable with a tube to close a mouth of the tube, the tube defining at least partly a sample collection space for receiving the naturally expressed body fluid, the device (optionally the cap, or optionally the tube) comprising a chamber for containing a reagent for mixing with a collected sample; wherein the device (optionally the cap, or optionally the tube) further comprises a manually operable actuator operable from outside the device at least once the cap has been secured to the tube, for causing the chamber to be opened in response to manual actuation of the actuator.

An embodiment represented in a apparatus comprising: a device according to embodiment 249; and packaging in which the device is intended to be placed, the packaging configured to accept the device only in a condition in which the actuator has been actuated to cause the chamber to be opened.

An embodiment represented in a bodily fluid sample collection device comprising a tube, and a cap securable to a mouth portion of the tube, the tube defining at least partly a sample collection space for receiving the naturally expressed body fluid, and the device (optionally the cap, or optionally the tube) comprising a chamber for containing a reagent for mixing with a collected sample; wherein the mouth portion is separable from a collection portion the tube, to facilitate opening of the device after the cap has been secured.

The device of embodiment 251, wherein the cap is a separate body from the mouth portion, and securable thereto to close the mouth portion.

An embodiment represented in a kit for collection of a bodily fluid sample from which cells and/or DNA may be isolated for analysis, the kit comprising apparatus or device as defined in any preceding embodiment.

The kit of embodiment 253, further comprising a reagent in the device, the reagent configured to preserve cells and/or cell components.

Use of a sample bodily fluid sample collection device as defined in any of embodiments 246 to 249, 250 or 251, for collecting of a bodily fluid sample for analysis of cells or cellular components, the analysis selected from: genetics; epigenetics; diagnostics; or other purposes.

An embodiment represented in a solution for preserving cells in bodily fluid for further separation into cell types and downstream epigenetic analysis that allows for storage of cells in bodily fluid to retain their antigenicity and cellular architecture, the solution comprising at least one chemical fixing agent and at least one protease inhibitor, buffered at a pH from about 6.4 to about 8.4, wherein the solution is effective to preserve cells for a duration of at least 1 week.

The solution of embodiment 256, wherein the solution is effective to preserve cells for a duration selected from: at least two weeks; or at least three weeks, or at least a month, or at least two months; or at least three months.

The solution of embodiment 256 or 257, wherein the solution is effective to preserve cells when kept at a temperature selected as at least one of the following temperatures or temperature ranges: between 4° C. and 40° C.; between 4° C. and 30° C.; about room temperature; about 4° C.; about 30° C.; about 40° C.

The solution of embodiment 256, 257 or 258, wherein the solution has a shelf-life selected from at least one of the following: at least 1 month; at least two months; at least three months; at least four months.

The solution of embodiment 259, wherein the shelf-life is shelf-life at room temperature.

The solution of any of embodiments 256 to 260, wherein the solution is effective to preserve at least a predetermined percentage of cells from an original sample of the body fluid, the predetermined percentage being selected from: at least 50%, at least 55%, at least 60%, at least 65%, at least 70%, at least 75%, at least 80%, at least 85%, at least 90%, at least 95%.

The solution of any of embodiments 256 to 261, wherein a number of preserved cells or a predetermined type, per nil is at least about 5000, or at least about 10000, or at least about 12000.

The solution of any of embodiments 256 to 262, wherein the cells are T-cells.

The solution according to any of embodiments 256 to 263, further comprising one or more of at least one antimicrobial agent and serum proteins from human and/or other animal species.

The solution according any of embodiments 256 to 264, wherein the chemical fixing agent is selected from the group consisting of aldehydes.

The solution according to embodiment 265, wherein the chemical fixing agent is paraformaldehyde.

The solution according to any of embodiments 256 to 266, wherein the chemical fixing agent is present at a concentration of about 1% (v/v).

The solution according to any of embodiments 256 to 267, wherein the antimicrobial agent is selected from the group consisting of antibacterial and antifungal antibiotics.

The solution according to any of embodiments 256 to 268, wherein the protease inhibitor is selected from the group consisting of: Aspartic protease inhibitors, Cysteine protease inhibitors, Metallo protease inhibitors, Serine protease inhibitors, Threonine protease inhibitors, Trypsin inhibitors, Kunitz STI protease inhibitor and a combination of any of the foregoing.

The solution according to any of embodiments 256 to 269, wherein the protease inhibitor is selected from the group consisting of sodium azide, PMSF, aprotinin, leupeptin, pepstatin, natural or synthetic proteinase inhibitors, mixtures of protease inhibitors both natural and synthetic, and any combination of the foregoing.

The solution according to any of embodiments 256 to 270, wherein the protease inhibitor is sodium azide.

The solution according to any of embodiments 256 to 271, wherein the solution is buffered at a pH of from about 7.2 to about 7.6.

The solution according to any of embodiments 256 to 272, wherein the buffer is selected from the group consisting of: barbital, trisphosphate, citrate, cacodylate, other non-phosphate buffers and any combination of the foregoing.

The solution according to any of embodiments 256 to 273, wherein the buffer is a phosphate buffer.

An embodiment represented in a method for preserving cells in a naturally expressed bodily fluid comprising contacting the bodily fluid with the preservation solution according to any of embodiments 256 to 274.

A sample collection device for collection of a naturally expressed bodily fluid, the sample collection device containing a preservation solution according to any of embodiments 256 to 274.

A sample collection kit including a solution as defined in any of embodiments 256 to 274.

Any and all references to publications or other documents, including but not limited to, patents, patent applications, articles, webpages, books, etc., presented anywhere in the present application, are herein incorporated by reference in their entirety.

Example embodiments of the devices, systems and methods have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with features and claims supported by the present disclosure and their equivalents. Moreover, embodiments of the subject disclosure may include methods, systems and devices which may further include any and all elements/features from any other disclosed methods, systems, and devices, including any and all features corresponding to user-experience functionality/systems/methods, including the manufacture and use thereof. In other words, features from one and/or another disclosed embodiment may be interchangeable with features from other disclosed embodiments, which, in turn, correspond to yet other embodiments. Moreover, embodiments, or features thereof, disclosed in the instant application may be combined with features and/or embodiments disclosed in the incorporated by reference information and yield yet other embodiments of the present disclosure.

One or more features/elements of embodiments supported by the present disclosure may be removed and still result in patentable subject matter (and thus, resulting in yet more embodiments of the subject disclosure). Furthermore, some embodiments of the present disclosure may be distinguishable from the prior art by specifically lacking one and/or another feature, functionality or structure which is included in the prior art (i.e., claims directed to such embodiments may include "negative limitations").

What is claimed is:

1. A sample collection device for the collection of a bodily fluid, comprising:
   a cap, and
   a tube having a mouth and an engager therein, the engager positioned lower inside on an inner wall of the mouth and spaced axially away from a center of the mouth, wherein:
   the cap is configured to threadedly couple to the tube so as to close the mouth of the tube and comprises:
      a first cap portion including an aperture, an inner wall inside the cap, and a radially inwardly facing thread, wherein the inner wall and the aperture defines at least a portion of a chamber for containing a reagent, and
      a second cap portion defining a closure for closing the aperture and including a radially outwardly facing thread and at least one abutment on the perimeter of the second cap portion;
   the radially outwardly facing thread of the second cap portion is configured to threadedly couple to the radially inwardly facing thread of the first cap portion;
   the threaded coupling between the first and second cap portions has a thread direction opposite to the threaded coupling between the cap and the tube, such that:
      when the cap is fitted onto the tube, the at least one abutment engages with the engager,
      the engager restrains the second cap portion against rotation with respect to the tube, and
      the second cap portion disengages from the first cap portion and descends fully into the tube, thereby providing a visual signal that the reagent descends into the tube;
   the tube defines at least a portion of a sample collection space for receiving the bodily fluid; and
   the engager extends from below an open end of the mouth towards the sample collection space for at least the length of distance traveled by the second cap portion from a closed position to an open position.

2. The device of claim 1, wherein the first and second cap portions are relatively movable with respect to each other, the first and second cap portions being configured such that, responsive to coupling of the cap to the tube, one of the cap portions is caused to move relative to the other cap portion to open the chamber and permit fluid communication between the chamber and the sample collection space, whereby a reagent in the chamber is permitted to mix with the bodily fluid in the sample collection space.

3. The device of claim 1, wherein the tube comprises a support for preventing the second cap portion from dropping into the sample collection space.

4. The device of claim 1, wherein the tube has a sample collection portion having a smaller interior cross-sectional area than at a mouth for receiving a cap for closing the device, and/or the cross-section area of the sample collection space is configured to not accommodate the second cap portion, whereby the second cap portion is obstructed from dropping down into the sample collection space.

5. The device of claim 4, wherein the sample collection portion bears at least one mark indicating sample volume and/or a fill level.

6. The device of claim 1, wherein the second cap portion comprises or is provided with a feature for permitting retrieval of the second cap portion from a dropped down position in the tube, the feature optionally being a magnetic element or a blind hole.

7. The device of claim 1, wherein the device is configured to provide to a user a second signal indicative of the cap having reached a closed and/or locked position.

8. The device of claim 7, wherein the second signal comprises any one or a combination of two or more of: a visual signal, an audible signal, a tactile signal.

9. The device of claim 7, wherein the cap further comprises a lock device engageable upon the cap reaching a fully closed position of the tube, the lock device configured for locking the cap in the fully closed position, and wherein the second signal is generated by operation of the lock device.

10. The device of claim 1, wherein the second cap portion comprises at least a portion having a top-hat shape including a cup portion defining a cavity, and a flange encircling the cup portion.

11. The device of claim 10, wherein the cup portion is configured for entering the open end of the chamber for closing the chamber.

12. The device of claim 1, wherein fitting the cap onto the tube is via at least a first amount of rotation.

13. The device of claim 12, wherein the first amount is not more than three turns, and wherein a second amount of rotation between the first and second cap portions to open the chamber is less than the first amount of rotation.

14. The device of claim 12, wherein the first amount of rotation is selected from: not more than two and a half turns; not more than two turns; not more than one and a half turns; or not more than one turn.

15. The device of claim 13, wherein the second amount of rotation is selected from: not more than one turn; not more than three-quarters of a turn; not more than half a turn; or not more than a quarter of a turn.

16. The device of claim 13, wherein the second amount of rotation comprises a first angular segment for the engager of the tube to cooperate with the second cap portion to restrain the second cap portion against rotation with respect to the tube, and a second angular segment for the threaded coupling between the first and second cap portions to unscrew; and optionally further wherein:
- the first angular segment is selected from: not more than about a quarter of a turn, or not more than about half a turn; and
- the second angular segment is selected from: not more than about a quarter of a turn, or not more than about half a turn.

17. The device of claim 1, wherein the second cap portion comprises two abutments on the perimeter of the second cap portion.

18. The device of claim 17, wherein the two abutments are diametrically opposed.

19. The device of claim 1, wherein the tube comprises at least one lock wedge on the outside of the mouth, and wherein the cap comprises at least one lock keep configured to engage the at least one lock wedge, thereby locking the cap in a fully closed position.

20. The device of claim 19, wherein the tube comprises two lock wedges, and wherein the cap comprises two lock keeps.

* * * * *